(12) United States Patent
Wu et al.

(10) Patent No.: US 8,835,476 B2
(45) Date of Patent: Sep. 16, 2014

(54) SYNTHESIS OF NOVEL ANTIMICROBIALS

(76) Inventors: Fan Wu, Halifax (CA); Donald Weaver, Halifax (CA); Chris Barden, Halifax (CA); Christopher McMaster, Halifax (CA); David Byers, Halifax (CA); Annette Henneberry, Halifax (CA); Fuqiang Ban, Halifax (CA)

(*) Notice: Subject to any disclaimer, the term of this patent is extended or adjusted under 35 U.S.C. 154(b) by 1449 days.

(21) Appl. No.: 11/909,636

(22) PCT Filed: Mar. 6, 2006

(86) PCT No.: PCT/CA2006/000314
§ 371 (c)(1),
(2), (4) Date: Sep. 25, 2007

(87) PCT Pub. No.: WO2006/092059
PCT Pub. Date: Sep. 8, 2006

(65) Prior Publication Data
US 2010/0076028 A1    Mar. 25, 2010

Related U.S. Application Data

(60) Provisional application No. 60/658,205, filed on Mar. 4, 2005.

(51) Int. Cl.
| | | |
|---|---|---|
| *A01N 43/64* | (2006.01) | |
| *A61K 31/41* | (2006.01) | |
| *A01N 43/06* | (2006.01) | |
| *A61K 31/38* | (2006.01) | |
| *C07D 257/04* | (2006.01) | |
| *C07D 257/10* | (2006.01) | |
| *C07D 403/00* | (2006.01) | |
| *C07D 487/00* | (2006.01) | |
| *C07D 333/02* | (2006.01) | |
| *C07D 409/00* | (2006.01) | |
| *C12Q 1/18* | (2006.01) | |
| *C07D 495/14* | (2006.01) | |
| *C07D 409/04* | (2006.01) | |
| *C07D 409/14* | (2006.01) | |

(52) U.S. Cl.
CPC ............. *C12Q 1/18* (2013.01); *C07D 495/14* (2013.01); *A61K 31/41* (2013.01); *C07D 409/04* (2013.01); *C07D 409/14* (2013.01)

USPC ........... 514/381; 514/382; 514/438; 514/444; 548/250; 549/29; 549/59

(58) Field of Classification Search
USPC ................. 514/381, 382, 438, 444; 548/250; 549/29, 59
See application file for complete search history.

(56) References Cited

U.S. PATENT DOCUMENTS

| | | |
|---|---|---|
| 3,991,067 A | 11/1976 | Gregory et al. |
| 4,302,461 A | 11/1981 | Cherkofsky |
| 4,421,758 A | 12/1983 | Kawamoto et al. |
| 4,590,205 A | 5/1986 | Haber |
| 4,749,712 A | 6/1988 | Haber |
| 5,210,193 A | 5/1993 | Sum et al. |
| 5,571,810 A | 11/1996 | Matsuo et al. |
| 2002/0098248 A1* | 7/2002 | Fujiwara et al. ............ 424/725 |

FOREIGN PATENT DOCUMENTS

| | | |
|---|---|---|
| GB | 1381860 | 1/1975 |
| WO | WO00/71120 | 11/2000 |
| WO | WO01/82930 | 11/2001 |

OTHER PUBLICATIONS

Perry et al. 2004, Cefdinir: A review of its use in the management of mild to moderate bacterial infections. Drugs, 64 (13) pp. 1433-1464.*
Wyckoff et al Trends in Microbiology, vol. 6 No. 4, Apr. 1998 p. 154-159.
Onishi et al Science, vol. 274, Nov. 8, 1996 p. 980-982.

* cited by examiner

*Primary Examiner* — Kara R McMillian
(74) *Attorney, Agent, or Firm* — Michael R. Williams; Ade & Company Inc

(57) ABSTRACT

The synthesis and activity of novel LpxA inhibitors is described, these inhibitors present antibacterial activity. The compounds were designed based on a receptor model developed using the crystal structure of LpxA and are arranged to have a favorable binding interaction at the active site of the enzyme. In particular, the compounds present the following formula (I) where V, W, X, Y and Z can be independently C, S, N or O and P1, P2 and P3 are ligands to bind to the three points of the proposed pharmacophore model. They can be chosen from a variety of groups.

10 Claims, 20 Drawing Sheets

A

B

Figure 1:
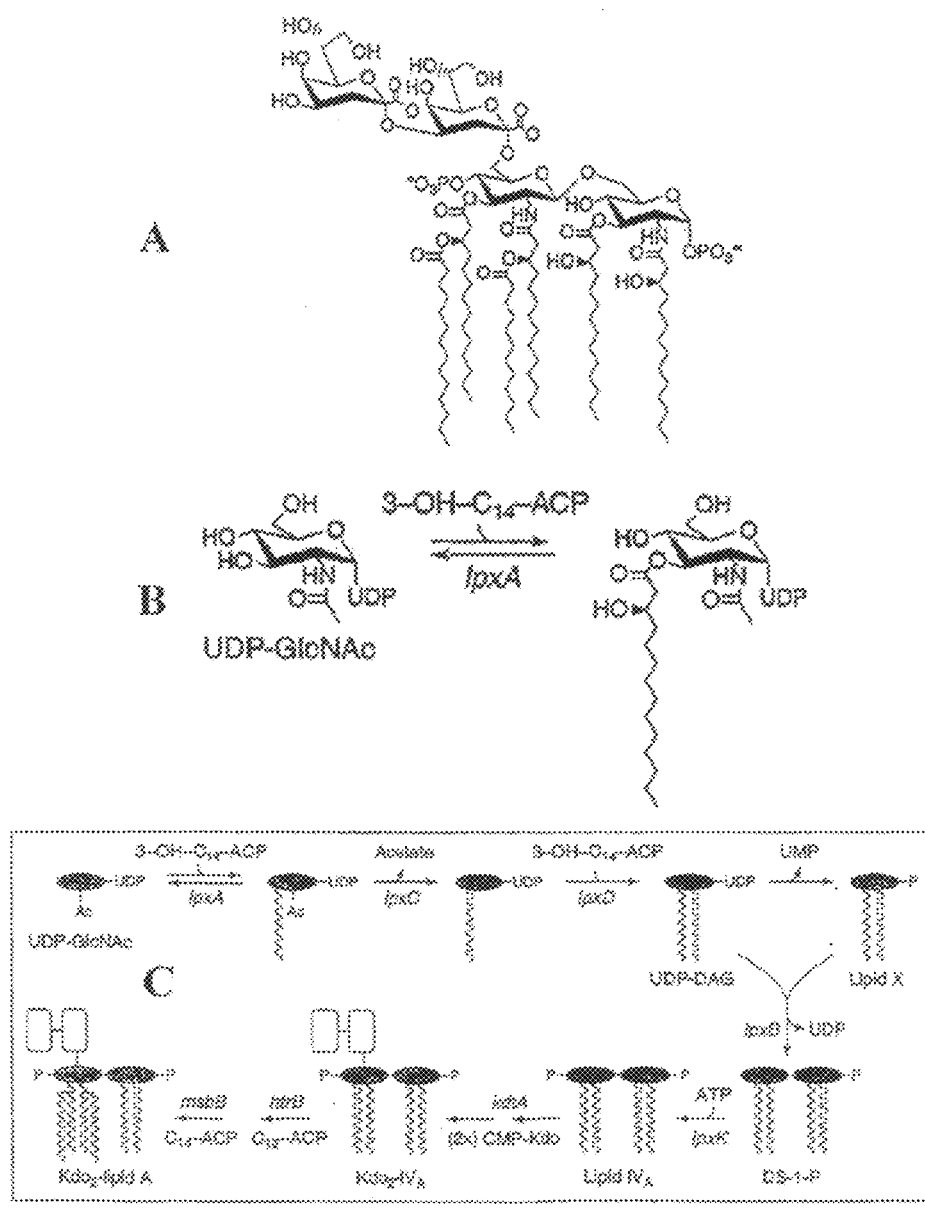

Fig. 12 (Method A)
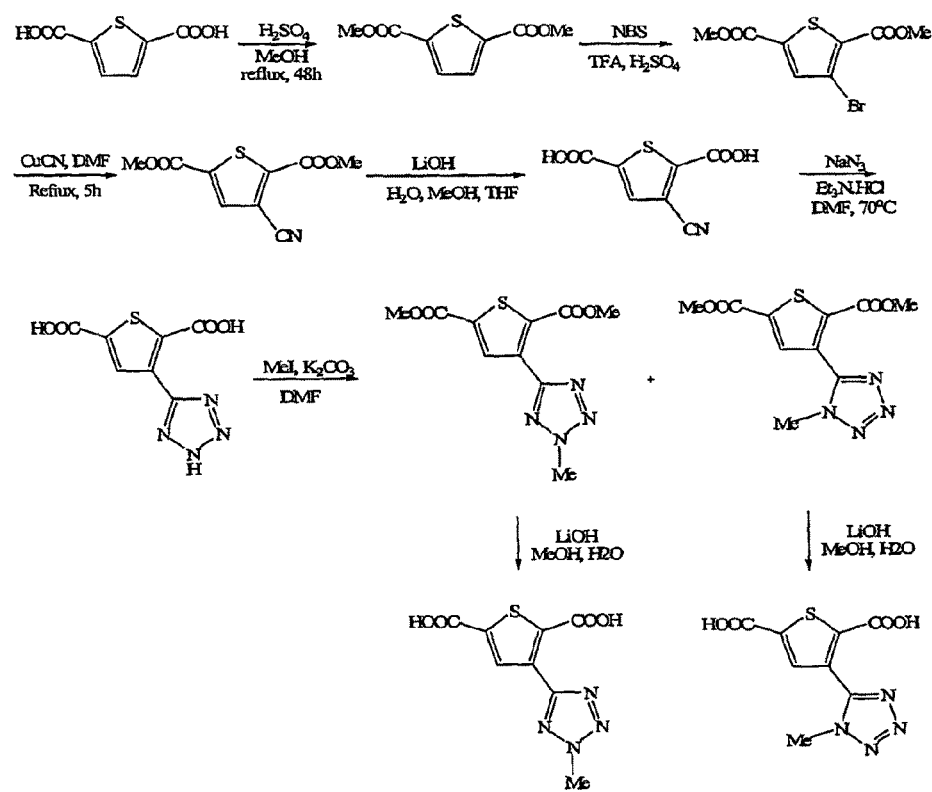

Fig. 13 (Method B)
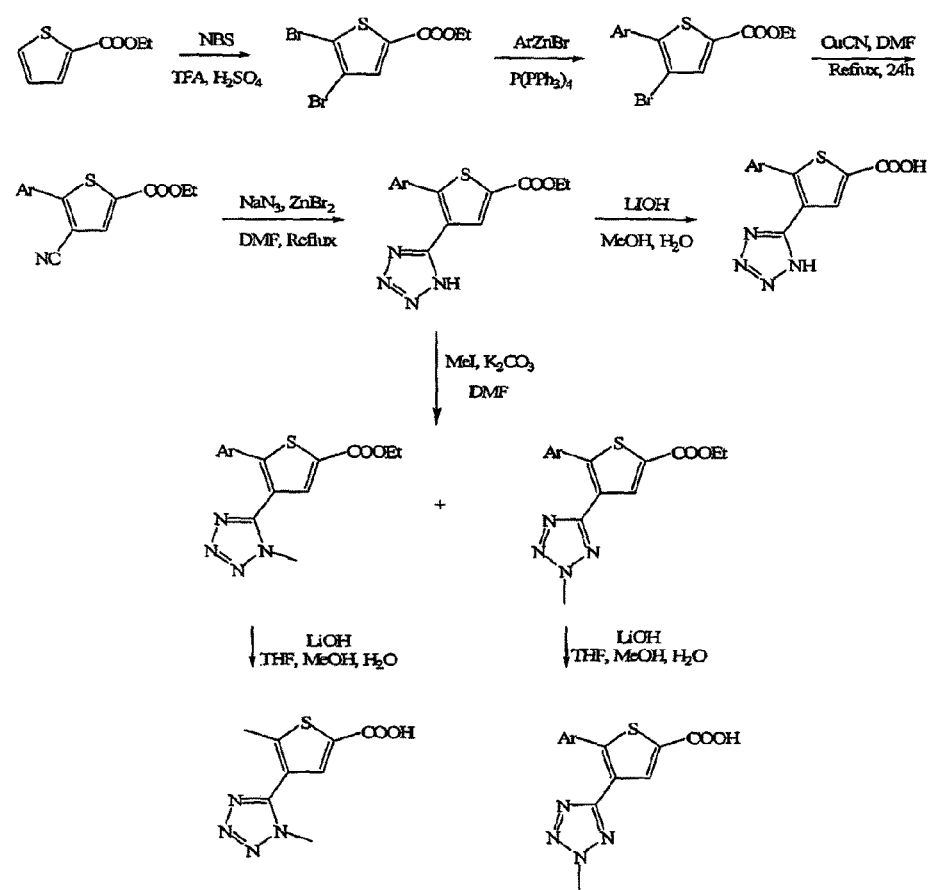

Fig. 14 (Method C)
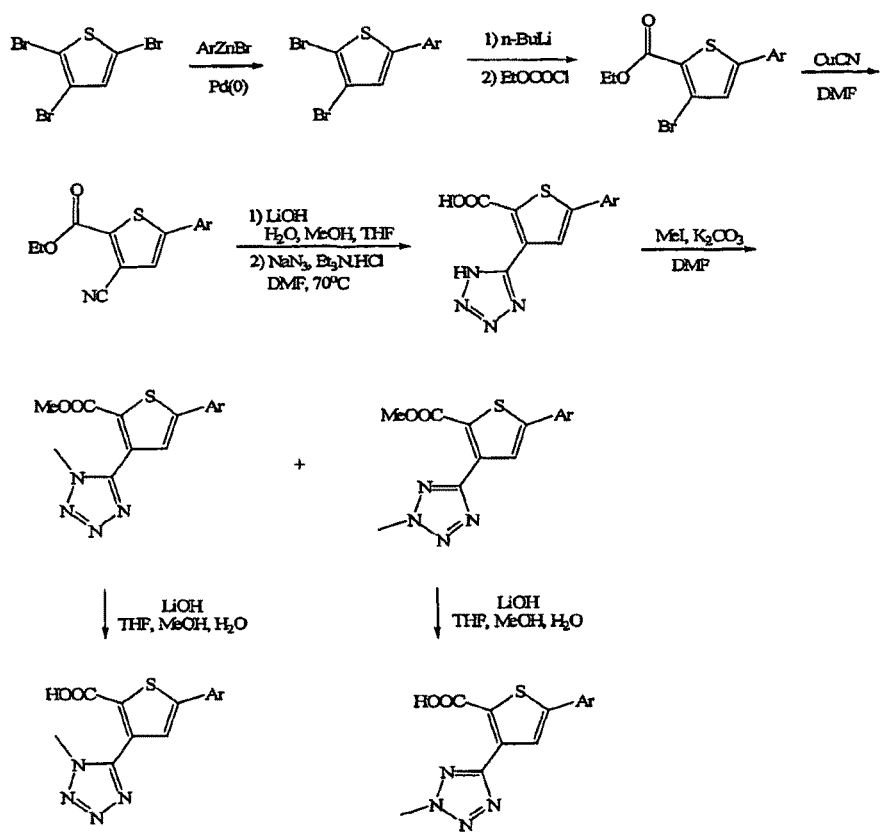

Fig. 15 (Method D)
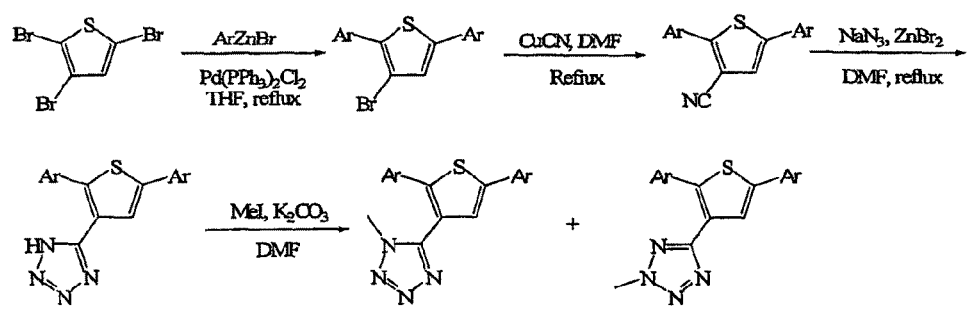

Fig. 16 (Method E)
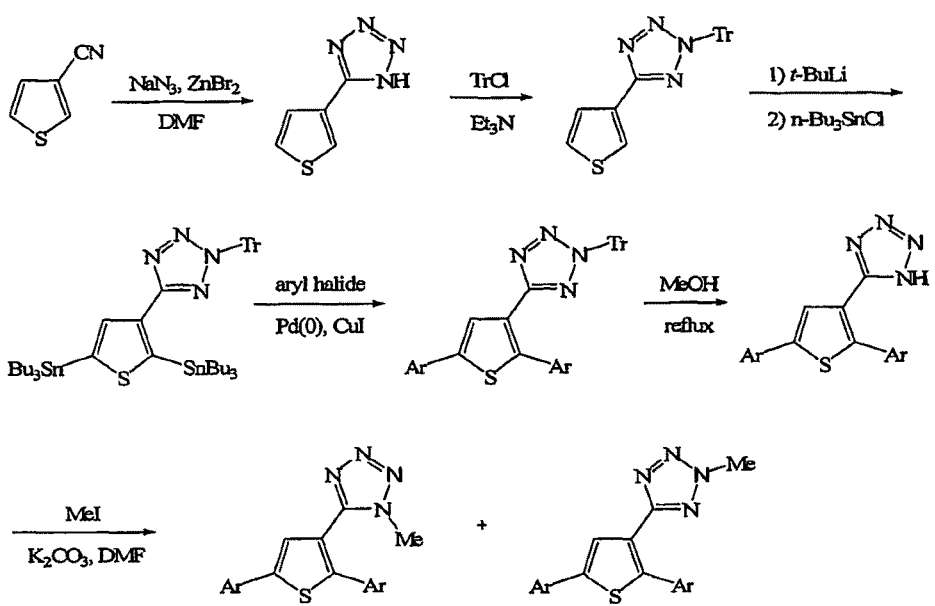

Fig. 17 (Method F)
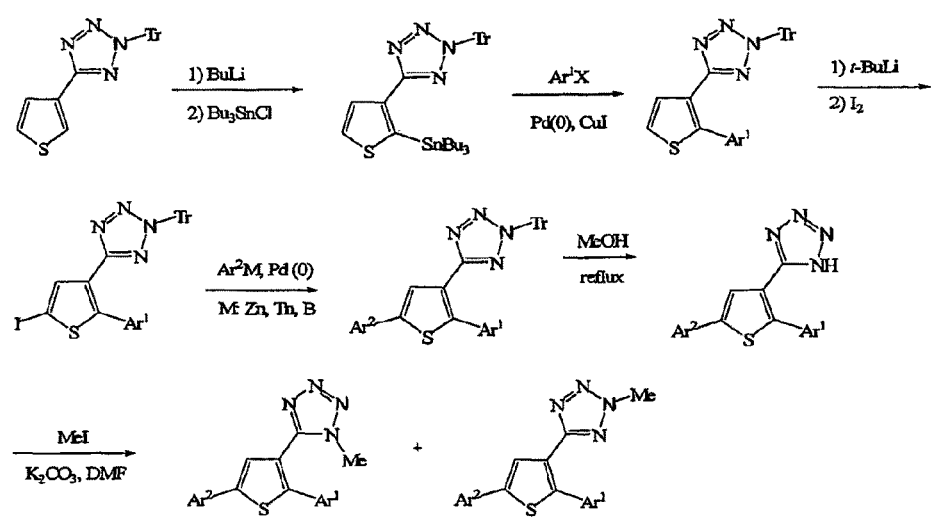

Fig. 18 (Method G)
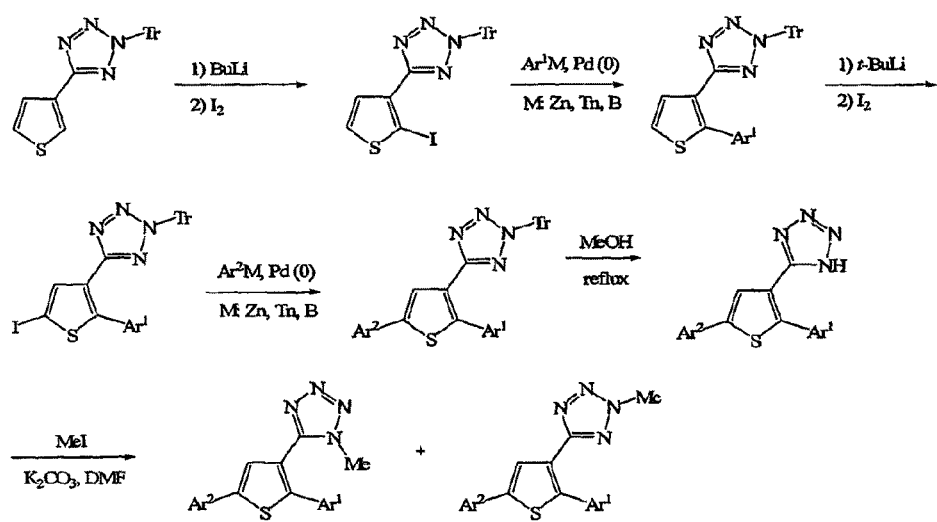

US 8,835,476 B2

SYNTHESIS OF NOVEL ANTIMICROBIALS

PRIOR APPLICATION INFORMATION

This application claims the benefit of U.S. Provisional Application 60/658,205, filed Mar. 4, 2005.

BACKGROUND OF THE INVENTION

Lipid A (endotoxin) is the hydrophobic anchor of lipopolysaccharide (LPS) in the outer membrane of gram-negative bacteria (FIG. 1), and is an attractive antimicrobial target for three principal reasons. First, lipid A is essential for growth of *E. coli* and many other gram-negative pathogens (Raetz and Whitfield, 2002, Annu Rev Biochem 71: 635-700; Wyckoff et al., 1998, Trends Microbiol 6: 154-159). Second, decreased synthesis of lipid A can disrupt the integrity of the outer membrane, rendering bacteria more susceptible to other antibiotics. Finally, lipid A is one of the most potent immunostimulatory agents known, and is recognized by the TLR4 receptor in the mammalian innate immune system (Kaisho and Akira, 2002, Biochim Biophys Acta. 1589: 1-13). Endotoxic (septic) shock is one of the leading causes of mortality in intensive care units, responsible for over 100,000 deaths annually in North America (Kaisho and Akira, 2002). Thus, inhibition of lipid A synthesis: (i) directly kills pathogenic bacteria, (ii) makes them more susceptible to existing antibiotics, and (iii) simultaneously decreases levels of circulating endotoxin to prevent septic shock in infected patients. A specific inhibitor (L-573,655) of another enzyme in lipid A biosynthesis that is not ACP dependent (LpxC—catalyzes the deactylation of UDP-3-acyl-GlcNAc) has been identified and shows bacteriocidal activity against a broad variety of gram-negative pathogens, including *E. coli* and *Pseudomonas aeruginosa* (Wyckoff et al., 1998; Onishi, 1996, Science 274: 980-982).

All enzymes involved in *E. coli* lipid A biosynthesis have now been identified, and their structural genes have been cloned. The first step in lipid A biosynthesis is catalyzed by UDP-N-acetylglucosamine (UDP-GlcNAc) acyltransferase (LpxA), which transfers a β-hydroxy-fatty acyl group (typically 10-14 carbons in length, depending on the bacterial species) from ACP to the 3-OH glucosamine of UDP-GlcNAc (FIG. 1B). The x-ray structure of the *E. coli* (Raetz and Roderick, 1995, Science 270: 997-1000) and *Helicobacter pylori* (Lee and Suh, 2003, Proteins: Structure, Function and Genetics 53: 772-774) enzymes have been determined and are trimers of identical 30 kDa subunits. Chemical modification studies (Wyckoff and Raetz, 1999, J Biol Chem 274: 27047-27055) have indicated that the active site of LpxA is in a cleft shared by two adjacent subunits (FIG. 2). At one end of this cleft is an essential histidine residue (His-125) that promotes acyl transfer by general base catalysis (Wyckoff and Raetz, 1999), while the opposite end contains a glycine residue (Gly-173) that appears to act as a "hydrocarbon ruler" to determine fatty acid chain length specificity (Wyckoff et al., 1998, J Biol Chem 273: 32369-32372). The acidic acyl-ACP substrate may fit into an electropositive groove formed at the C-terminal contact regions between adjacent LpxA subunits (Lee and Suh, 2003). The Km values for UDP-GlcNAc and R-3-hydroxymyristoyl-ACP are 1 mM and 1 μM, respectively, and although myristoyl-ACP binds LpxA with similar affinity, it is not active as a substrate (Wyckoff and Raetz, 1999). LpxA is a potentially attractive drug target *E. coli* conditional lpxA mutants that exhibit <10% wild type LpxA activity are non-viable (Wyckoff et al., 1998). Moreover, even modest reduction (<30% decrease) of lipid A content in these mutants permits growth but increases sensitivity to erythromycin and rifampicin by >100-fold (Wyckoff et al., 1998).

Figure 3:
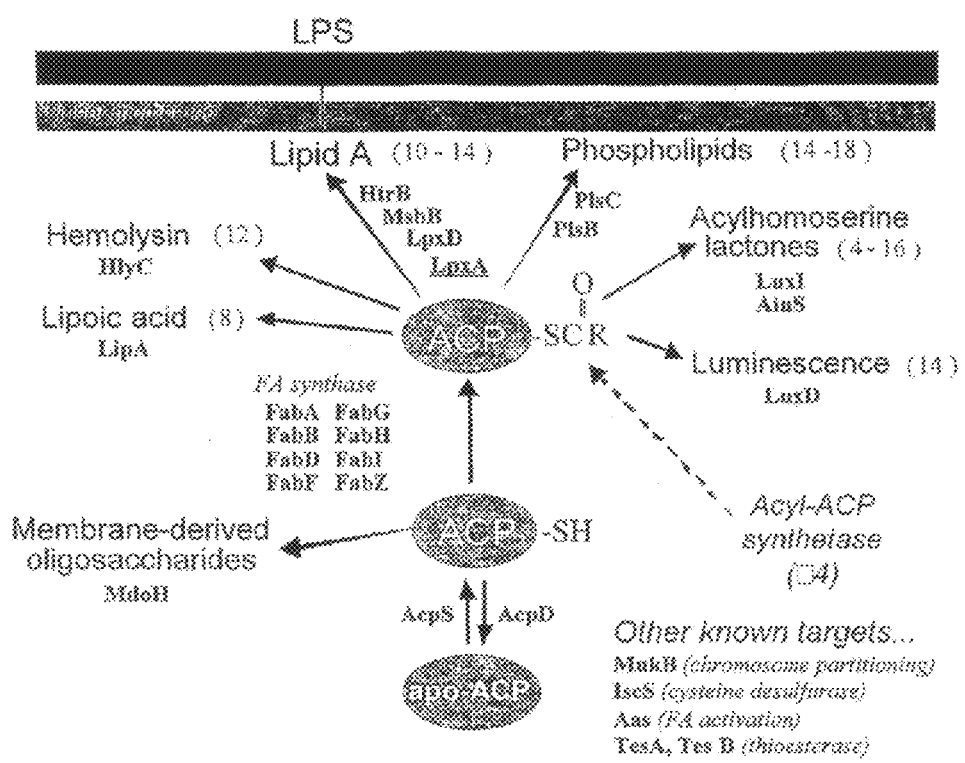

ACP is also required for many other lipid products essential for bacterial growth and pathogenesis, including phospholipids (Rock and Jackowski, 1982, J Biol Chem 257: 10759-10765), acylated protein toxins such as hemolysin (Issartel et al., 1991, Nature 351, 759-761), lipoic acid (Jordan and Cronan, 1997, J Biol Chem 272: 17903-17906), polyketides (Shen et al., 1992, J Bacteriol 174: 3818-3821), and the acyl homoserine lactones involved in bacterial quorum sensing, ie. regulation of the timed release of bacterial toxins and biofilm formation (Parsek and Greenberg, 2000, Proc Natl Acad Sci 97: 8789-8793). Bacterial ACP is a small (70-90 amino acid) protein to which fatty acyl groups are attached as thioesters during fatty acid synthesis, and acyl-ACPs interact directly with at, least two dozen enzymes in a typical bacterial cell (FIG. 3). The flexible yet highly conserved tertiary structure of bacterial ACP is dominated by three parallel α-helices; helix II appears to be the principal region involved in enzyme binding (Parris et al., 2000, Structure Fold Des 8: 883-895; Zhang et al., 2001, J Biol Chem 276: 8231-8238) although other ACP residues are also involved (Flaman et al., 2001, J Biol Chem 276: 35934-35939). The conserved structural features of bacterial ACPs, together with the fundamental architectural differences with mammalian fatty acid synthases (where ACP exists as a discrete domain within a large multifunctional protein), make ACP/acyl-ACP binding a potential target for the development of broad specificity antimicrobials. Indeed, several natural or synthetic compounds have been identified that inhibit specific fatty acid synthase subunits. The broad-spectrum compound triclosan and the anti-tuberculosis drug isoniazid both inhibit enoyl-ACP reductases (FabI), while thiolactomycin and 3-decynoyl-NAC inhibit condensing enzymes (FabB) and dehydratase/isomerase (FabA), respectively (Heath et al., 2002, Appl Microbiol Biotechnol 58: 695-703). The present investigators have developed specialized methods to engineer, overexpress, and purify large amounts of recombinant holo-ACP from the bacterium *Vibrio harveyi* (Flaman et al., 2001), and have isolated a novel enzyme (*V. harveyi* acyl-ACP synthetase), providing the capacity to produce wild type or mutant ACPs and the specific acylated derivatives that are substrates for key essential bacterial processes (Shen et al., 1992, Anal Biochem 204: 34-39; Fice et al., 1993, J Bacteriol 175: 1865-1870).

SUMMARY OF THE INVENTION

A good target for the development of broad specificity antimicrobials should satisfy several requirements. It should be essential for life, highly conserved in a range of prokaryotic species, and absent or very different in humans. Other major advantages include knowing the structure and function of the gene product, being able to efficiently manipulate the gene at a molecular level, and possessing the capacity to assay for protein function. For all these reasons, ACP/acyl-ACP is an excellent target for drug discovery. In addition, since acyl-ACP interacts with many bacterial enzymes presumably through different interaction sites it can be used as a platform for the development of several different antimicrobial drugs. Specifically, acyl-ACP is an essential donor of fatty acyl groups during fatty acid (FA) and phospholipid biosynthesis, acyl-ACP is required for the synthesis of the bioactive lipid A moiety of endotoxin in Gram-negative bacteria, for the acylation of protein toxins such as hemolysin, and for the synthesis of acylated homoserine lactones involved in bacterial quorum sensing, essential to the induction and timing of pathogenic processes in bacteria. Indeed, over a dozen enzymes involved in bacterial growth and pathogenesis are known to interact with ACP and its acylated derivatives and there are others yet to be discovered. Moreover, ACP is structurally distinct in prokaryotes and eukaryotes: it exists as a highly conserved protein subunit in the former, and as a discrete domain within the large multifunctional fatty acid synthases found in humans. Thus, it will be possible to identify or develop compounds that interfere with specific ACP-dependent processes in bacteria, while not affecting the restricted role of ACP in eukaryotic fatty acid synthesis.

Expression, mutagenesis, and structure/function analysis of bacterial ACP has been hampered by its toxicity in *E. coli*, due to an accumulation of the unmodified (apo) form of ACP. Recently, we have developed specialized methods to overexpress and purify large amounts of recombinant holo-ACP from the bacterium *Vibrio harveyi* produced in *E coli* for site-directed mutagenesis analysis. Our laboratory has also isolated a novel enzyme (*V. harveyi* acyl-ACP synthetase) such that we have the capacity to produce wild type or mutant ACPs and the specific acylated derivatives that are substrates for key essential bacterial processes. Our ability to prepare and isolate unique fatty acylated derivatives of ACP gives us a platform from which to potentially develop antibiotics based on interference of acyl-ACP binding with several of its protein partners. As a small (70-80 amino acid) protein with a defined structure, ACP is an excellent target for bioinformatic, genomic and proteomic approaches to drug discovery. At least 100 ACP sequences are presently known and several structures have been solved making it a good candidate for rational drug design and modelling studies, as well as comparative genomic approaches to match specific regions and residues with defined functions. Our initial platform target to which acyl-ACP interacts is the product of the LpxA gene for the synthesis of bacterial endotoxin. However, we recognize that ACP and acyl-ACP interact with many other proteins within a bacterial cell, some known and some unknown, and thus molecules that prevent acyl-ACP/LpxA interactions and/or catalysis may could also prevent the interactions or catalysis of other ACP/acyl-ACP interactions (both known and unknown) due to similar binding of these target proteins with ACP/acyl-ACP.

Lipid A (endotoxin) is essential for growth and pathogenesis of many gram-negative bacteria, and LpxA (β-hydroxymyristoyl-ACP UDP-GlcNAc acyltransferase) catalyzes the first step in lipid A biosynthesis. The present inventors have designed and synthesized a novel class of small molecules based on pharmacophore mapping of the known active site structure of *E. coli* LpxA and its predicted interaction site with acyl carrier protein (ACP). ACP and acyl-ACP also interact with many other prokaryotic proteins. Of 87 structurally related compounds synthesized to date, 35 inhibited *E. coli* LpxA activity in the 5 millimolar concentration range or below. Several other compounds of this class also exhibited growth inhibitory activity against a panel of bacteria implying that they may affect other ACP dependent processes either known or unknown.

According to a first aspect of the invention, there is provided an antimicrobial agent having a general structure as shown in FIG. 5A where:

a. V, W, X, Y, and Z are independently selected from the group consisting of C, S, N, or O.
b. P1, P2, and P3 individually may be selected from any one of the following:
—RH
—ROH
—RC(=O)OH
—RC(=O)NH$_2$
—RC(=NH)NH$_2$
—RSO$_3$H
—RPO$_3$H
—RC triply bonded to N
—R(Hal)
—RC(Hal)$_3$
—R(biph)
—R(naph)
—R(Ar)
—HC=CH(Ar) [E and Z isomers]
—C triply bonded to C(Ar)
tetrazole
1-methyltetrazole
2-methyltetrazole
where
"(biph)" is biphenyl, attached at any point;
"(naph)" is naphthylene, attached at any point;
"(Hal)" is any halogen;
"Ar" is any six-membered ring composed of C, S, N, and/or O, bearing any combination of no substitutions up to five substitutions, substitutions being selected from the group of halogens, methoxy, hydroxy, carboxy, amino, nitro, or amido groups, or their corresponding methyl or ethyl esters;
and "R" is any sequence created from the group of CH$_2$, C(=O), NH, or O, denoted "building blocks", such that the total number of building blocks is between zero and five.
c. Additionally, if P1 is tetrazole and P2 and/or P3 contains Ar, then a bond may exist between the nitrogen at the 1 position of tetrazole and the carbon at the position adjacent on the ring to P3's through-space point of contact with Y.

According to a second aspect of the invention, there is provided a method of developing and testing potential antimicrobials comprising providing a small molecule as described in the first aspect of the invention, and testing the small molecule for bacterial inhibition activity.

According to a third aspect of the invention, there is provided a method of treating or preventing a bacterial infection comprising administering to an individual in need of such treatment, an effective amount of one or more of the antimicrobial agent described above.

According to a fourth aspect of the invention, there is provided a method of treating a disease, disorder or condition caused by a bacterial infection comprising administering to an individual in need of such treatment, an effective amount of one or more of the antimicrobial agent described above.

BRIEF DESCRIPTION OF THE DRAWINGS AND TABLES

Figure 2:
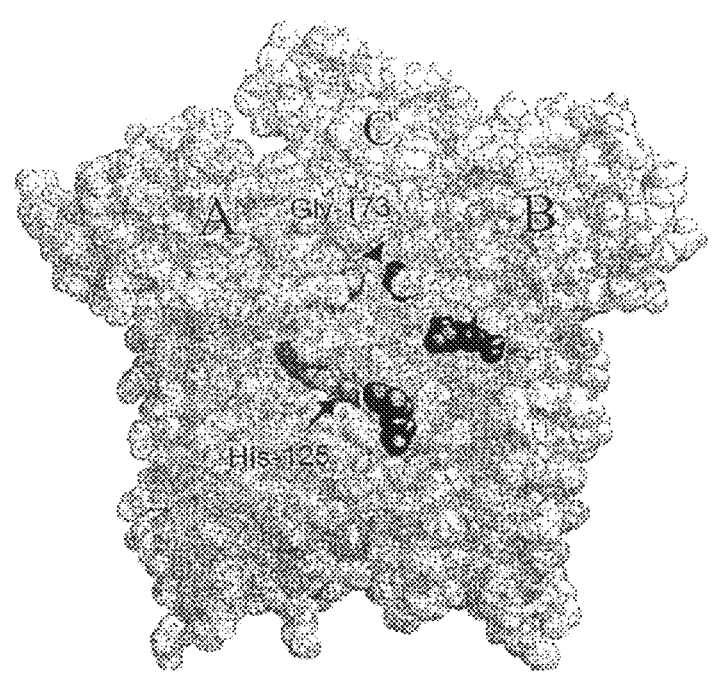

FIG. 1. Lipid A synthesis in *E. coli*. A: structure of Kdo2-lipid A product. B: LpxA-catalyzed reaction. C: the complete Lipid A biosynthetic pathway (Wyckoff et al., 1998).

FIG. 2. *E. coli* UDP-GlcNAc acyltransferase (LpxA) trimer showing the active site cleft and catalytic residues at the A/B subunit interface (Raetz and Roderick, 1995).

FIG. 3. Acyl-ACP-dependent products, enzymes, and pathways in gram-negative bacteria. *E. coli* nomenclature is used for all enzymes and acyl chain lengths typically found in the various products are indicated in parenthesis.

Figure 4:
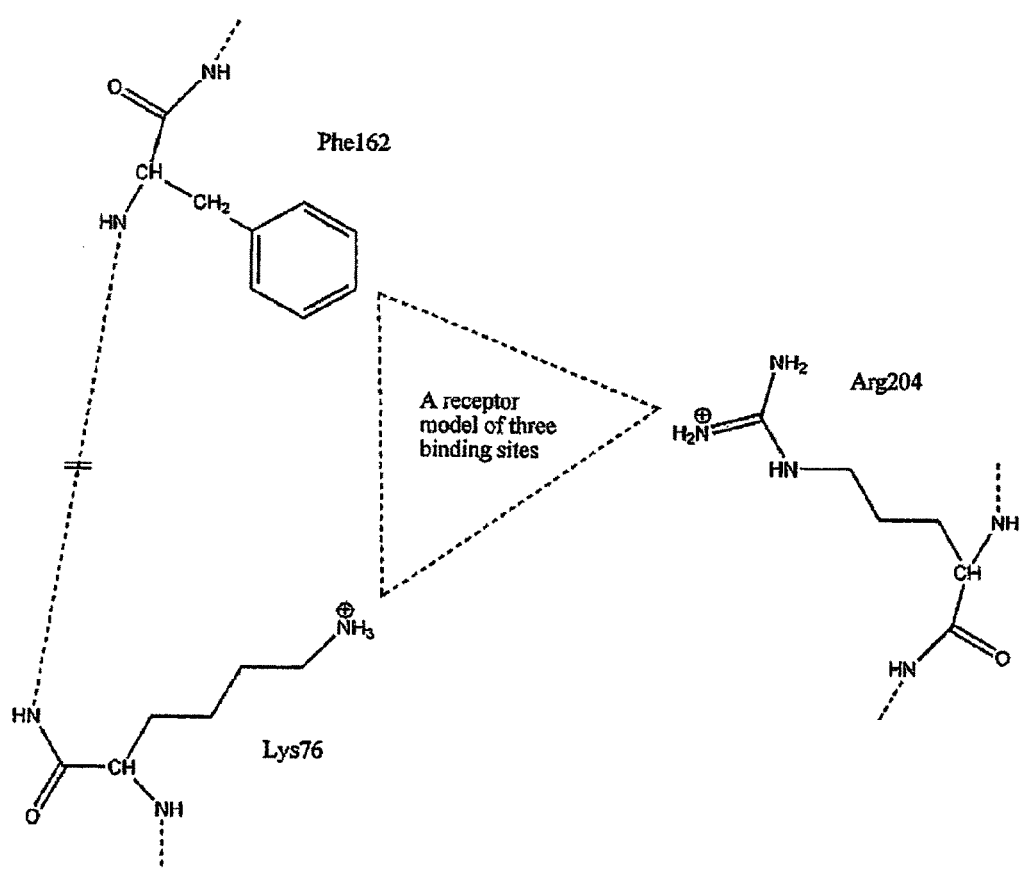

FIG. 4. The designed receptor model.

Figure 5:
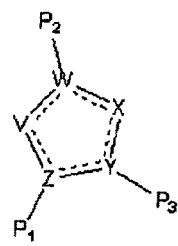
Figure 5:
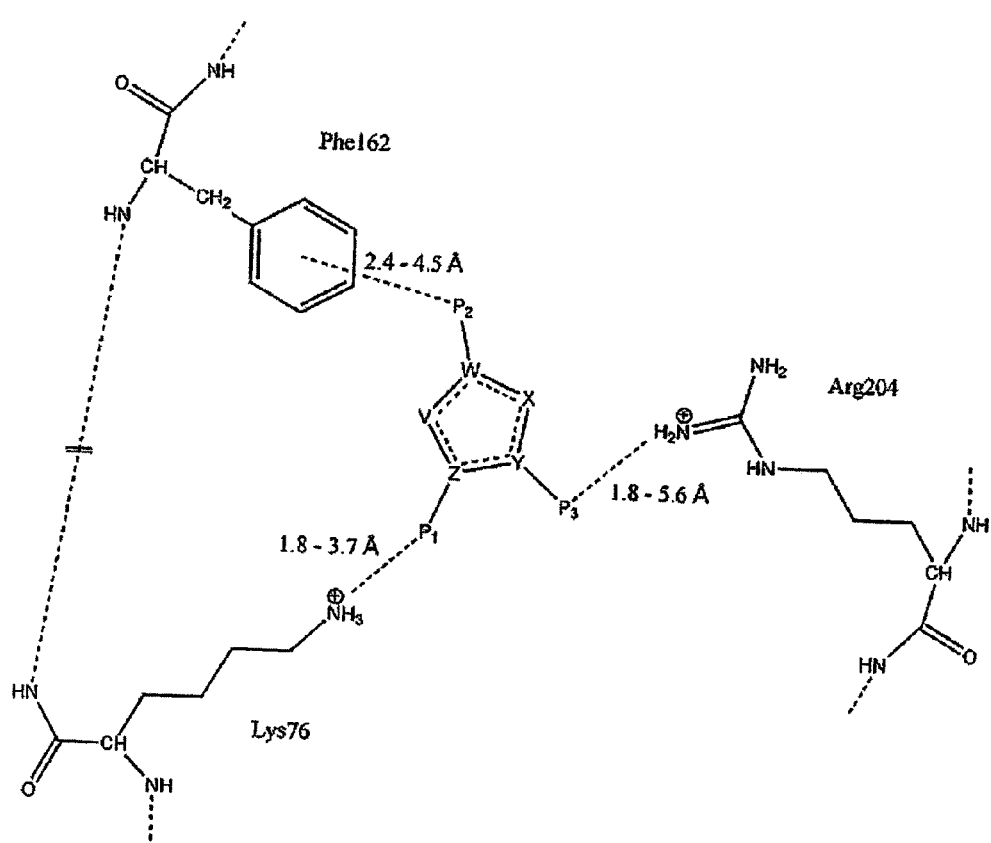

FIG. 5. Design of LpxA inhibitors. Panel A. General formula of inhibitors. Panel B. Potential ligands (P1, P2, P3) of the pharmacophore model, with distance ranges for the closest atom pairs of P1 to lysine, P2 to phenylalanine, and P3 to arginine. Panels C and D. Proposed binding of compound DNM-133 to the designed receptor model.

Figure 6:
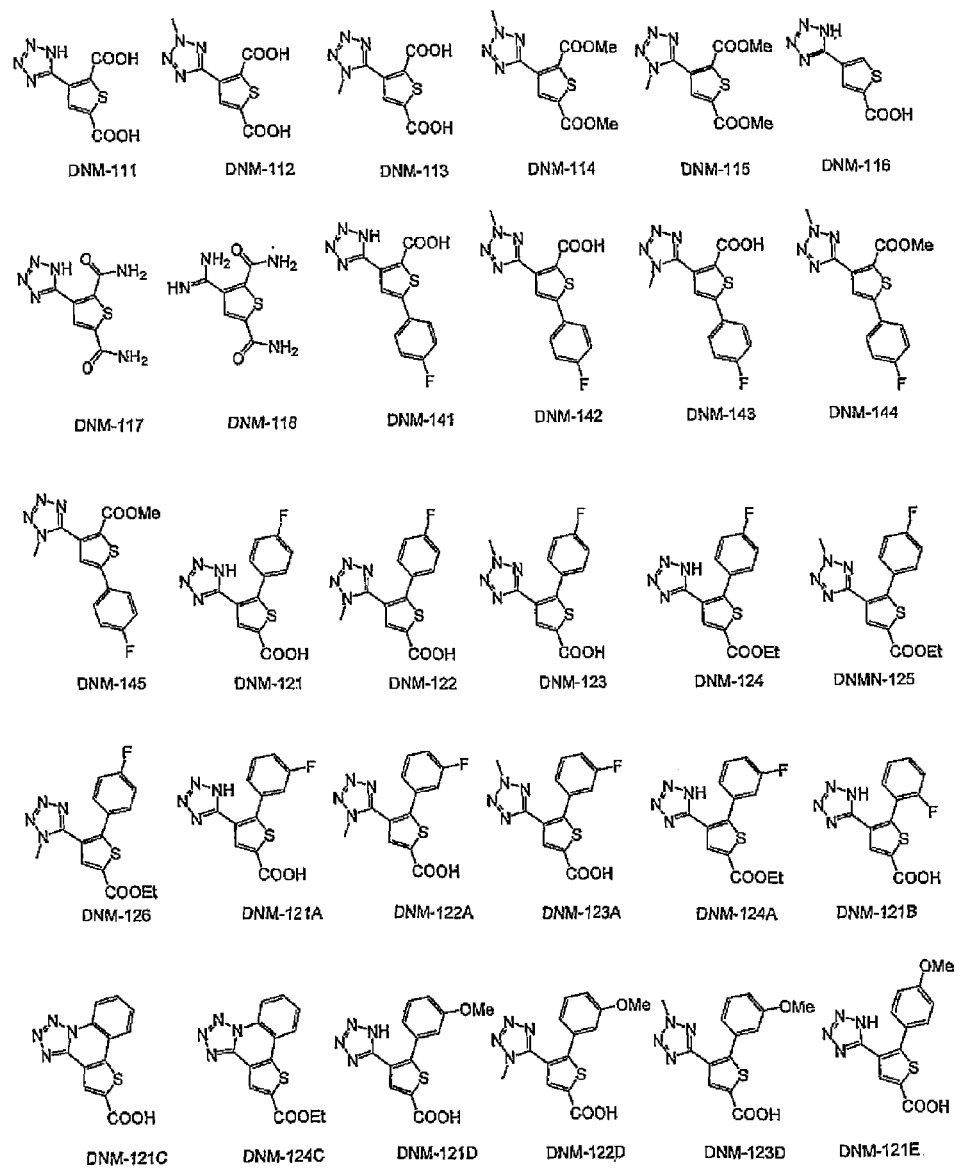
Figure 6A:
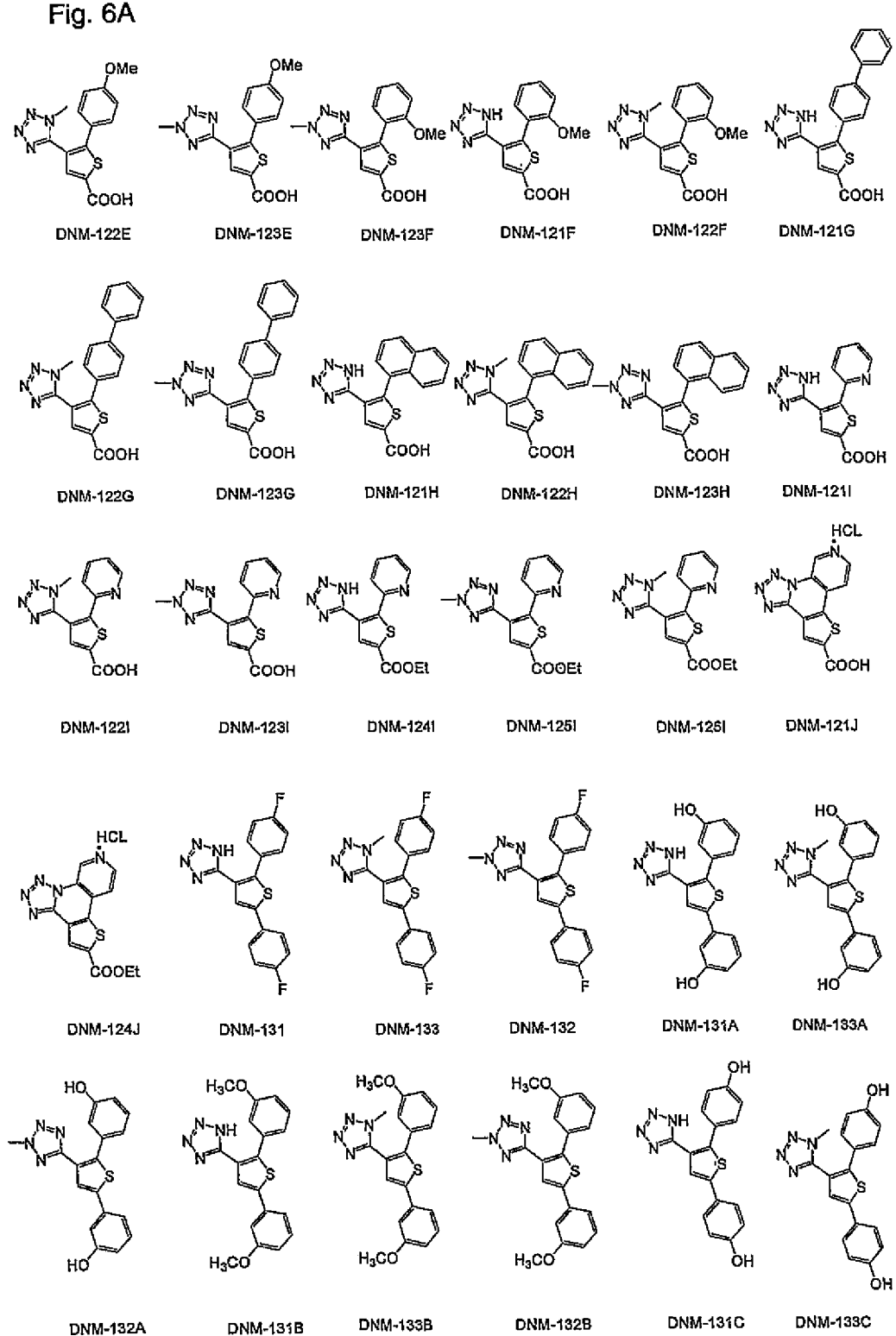
Figure 6B:
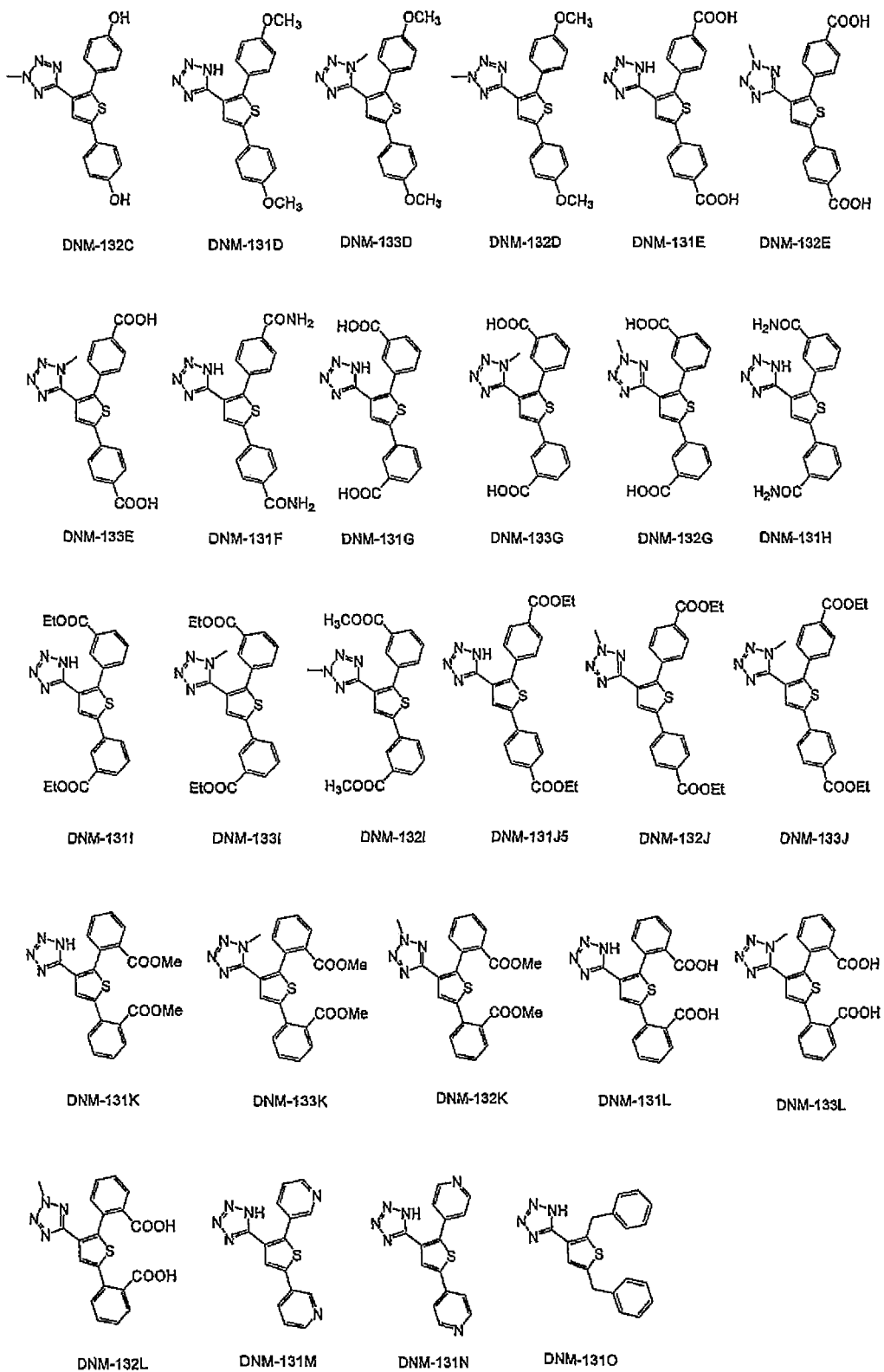

FIG. 6. Structures of the 87 compounds designed, synthesized, and tested for LpxA and growth inhibition.

Figure 7:
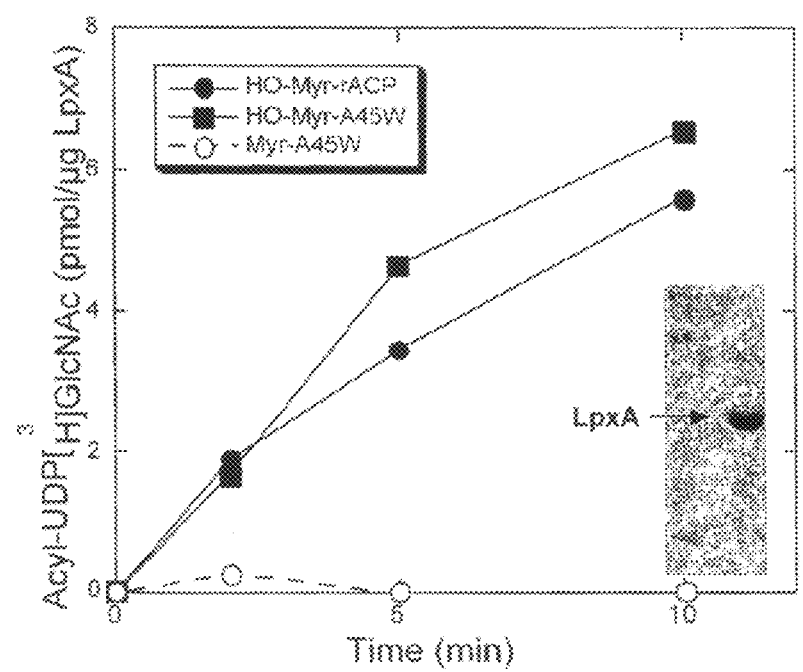

FIG. 7. Validation of LpxA assay. Formation of acyl-UDP-GlcNAc product from the indicated acyl-ACP donors as a function of time was measured as described in the text. Inset: recombinant His-tagged *E. coli* LpxA used in the assay.

Figure 8:
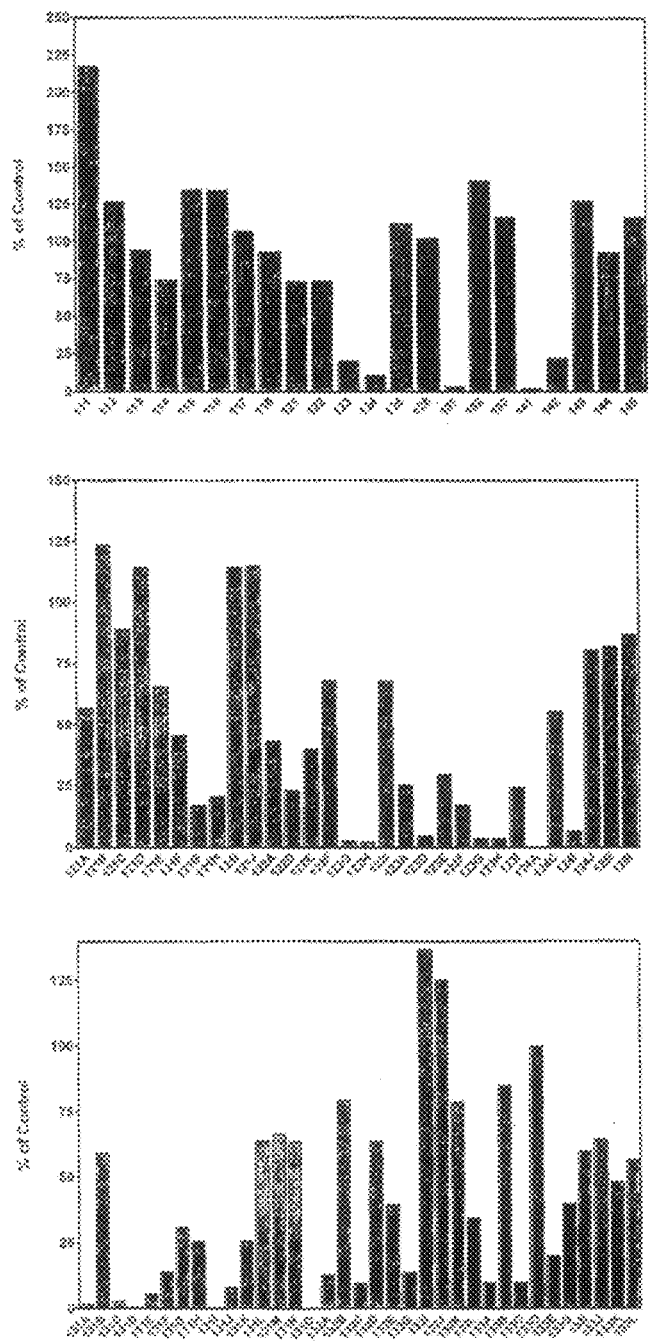

FIG. 8. Effect of test compounds on LpxA activity. Acyl-UDP-GlcNAc product formation in the presence of 5 mM of each compound was measured at 2, 5, and 10 min as described in the text to ensure linearity. Control reactions in the presence of an equivalent concentration of ethanol or DMSO (10% v/v) were also monitored for each set of assays. Data is shown as a percentage of the control reaction at 5 minutes.

Figure 9:
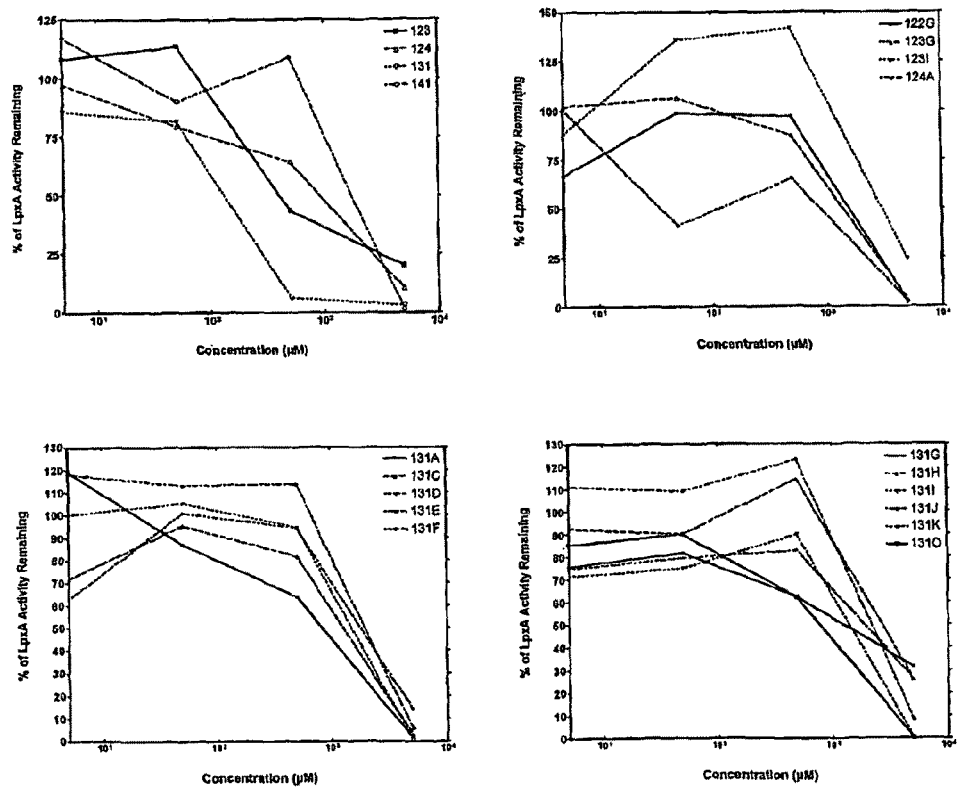

FIG. 9. Dose dependence of selected compounds on LpxA activity. Acyl-UDP-GlcNAc product formation in the presence of the indicated concentration of each compound was measured at 5 min as described in the text. Data is shown as a percentage of the control reaction at 5 minutes.

Figure 10:
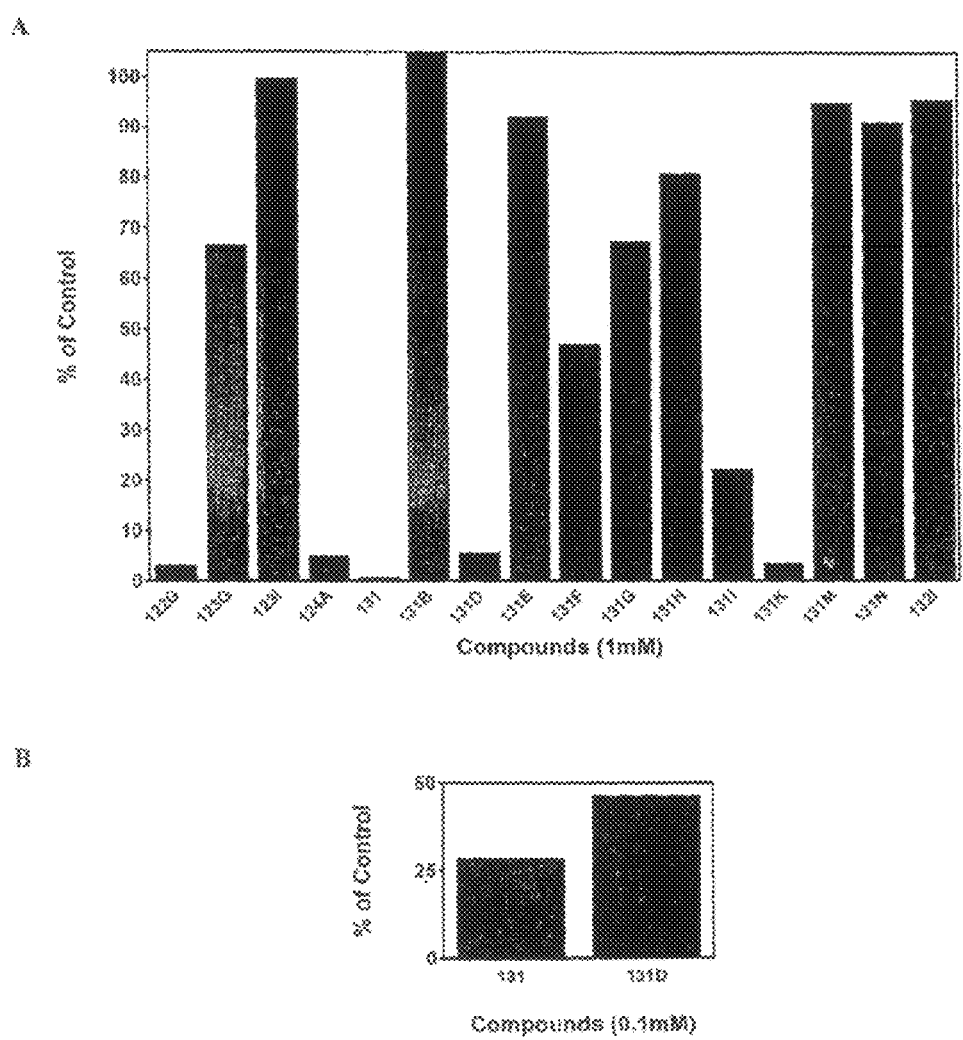

FIG. 10. Effect of test compounds on in vivo LPS synthesis. Early-log phase cultures were labelled with [$^3$H] galactose in the presence of selected compounds as described in the text. Control reactions in the presence of an equivalent concentration of DMSO (1%, v/v) were also monitored for each set of assays. Data is shown as a percentage of the control reaction at 5 minutes. A. Test compounds at 1 mM. B. Test compounds at 0.1 mM.

Figure 11:
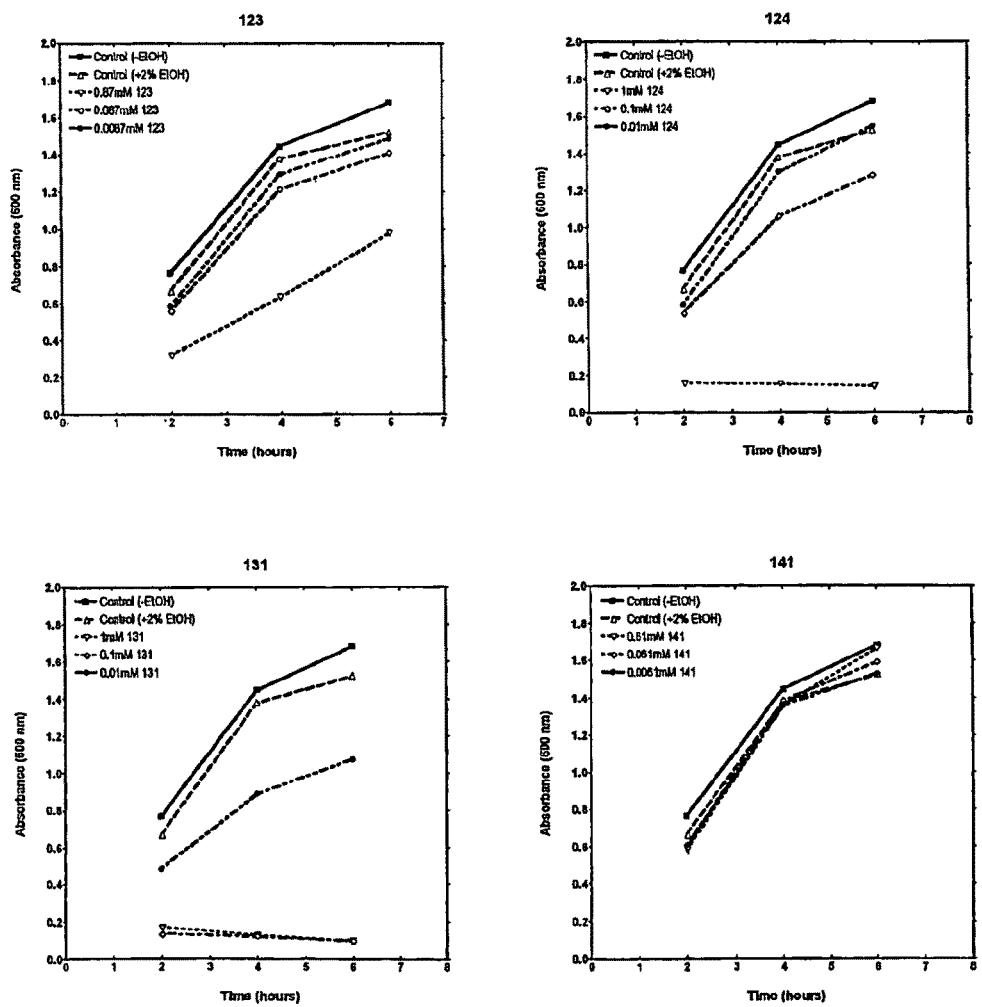

FIG. 11. Inhibition of *E. coli* growth in liquid culture. Culture tubes containing the indicated concentration of compounds 123, 124, 131, and 141 in LB medium were inoculated with *E. coli* BL21 cells and optical density at 600 nm was measured at the indicated times. Control cultures with and without 2% ethanol were also monitored.

FIG. 12. Synthetic Method A.
FIG. 13. Synthetic Method B.
FIG. 14. Synthetic Method C.
FIG. 15. Synthetic Method D.
FIG. 16. Synthetic Method E.
FIG. 17. Synthetic Method F.
FIG. 18. Synthetic Method G.

Table 1. List of organisms to which the panel of compounds was tested.

Table 2. Range (in μg/ml) for each compound tested versus the panel, of bacteria using the microdilution method.

Table 3A,B. Results of growth inhibition versus ATCC strains using the microdilution method.

Table 4A,B. Results of growth inhibition versus clinical isolate strains using the microdilution method.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As used herein, "effective amount" refers to the administration of an amount of a given compound that achieves the desired effect.

As used herein, "purified" does not require absolute purity but is instead intended as a relative definition. For example, purification of starting material or natural material to at least one order of magnitude, preferably two or three orders of magnitude is expressly contemplated as falling within the definition of "purified".

As used herein, the term "isolated" requires that the material be removed from its original environment.

As used herein, the term "treating" in its various grammatical forms refers to preventing, curing, reversing, attenuating, alleviating, minimizing, suppressing or halting the deleterious effects of a disease state, disease progression, disease causitive agent other abnormal condition.

As discussed above, lipid A is essential for growth of *E. coli* and many other gram negative pathogens, including but by no means limited to *Salmonella, Pseudomonas, Neisseria, Legionella, Haemophilus, Campylobacter, Helicobacter* and *Shigella*. Furthermore, decreased synthesis of lipid A can disrupt the integrity of the outer membrane, rendering bacteria more susceptible to other antibiotics. We have designed a series of LpxA inhibitors using various molecular modeling techniques via outside-in de novo approach.

Specifically, described herein are a class of novel antimicrobials having broad specificity. Thus, in one embodiment, the antimicrobials of the instant invention have formulae as given in FIG. 5A where V, W, X, Y, and Z can be independently either C, S, N, or O. Ligands P1, P2 and P3 constitute the three points of the proposed pharmacophore model, and may individually be selected from any one of the following:

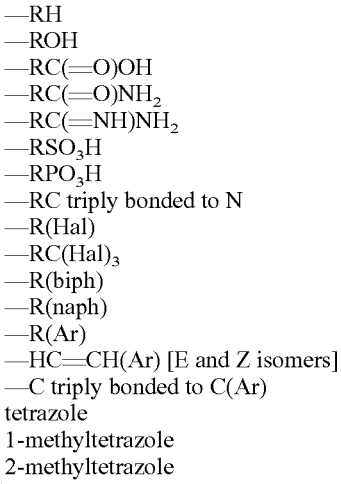

—RH
—ROH
—RC(=O)OH
—RC(=O)NH$_2$
—RC(=NH)NH$_2$
—RSO$_3$H
—RPO$_3$H
—RC triply bonded to N
—R(Hal)
—RC(Hal)$_3$
—R(biph)
—R(naph)
—R(Ar)
—HC=CH(Ar) [E and Z isomers]
—C triply bonded to C(Ar)
tetrazole
1-methyltetrazole
2-methyltetrazole where
"(biph)" is biphenyl, attached at any point;
"(naph)" is naphthylene, attached at any point;
"(Hal)" is any halogen, for example, but by no means limited to fluorine, chlorine, or bromine;
"Ar" is any six-membered ring composed of C, S, N, and/or O, bearing any combination of no substitutions up to five substitutions, said substitutions being selected from the group of halogens, methoxy, hydroxy, carboxy, amino, nitro, or amido groups, or their corresponding methyl or ethyl esters. For illustrative purposes, it is noted that synthesized examples of such rings include but are by no means limited to 4-fluorophenyl, 3-fluorophenyl, 4-methoxyphenyl, 4-pyridine, and 2-carboxyphenyl methyl ester;
and "R" is any sequence created from the group of CH$_2$, C(=O), NH, or O, denoted "building blocks", such that the total number of building blocks is between zero and five.

Additionally, if P1 is tetrazole and P2 and/or P3 contains Ar, then a bond may exist between the nitrogen at the 1 position of tetrazole and the carbon at the position adjacent on the ring to P3's through-space point of contact with Y.

Exemplary antimicrobial agents corresponding to the general formula as described above are shown in FIG. 6.

In one embodiment of the invention, there is provided a method of developing and testing potential antimicrobials comprising a small molecule having a structure as shown in FIG. 5A and described in the above embodiment, and testing the small molecule for bacterial inhibition activity. The bacterial inhibition activity may be tested in vitro, for example, inhibition of lpxA activity or in vivo, inhibition of bacterial growth, as discussed below. As will be appreciated by one of skill in the art, bacterial inhibition activity is a relative term and is determined by comparison with one or more controls, for example, a negative control wherein no compound or a known inactive compound is added to a similarly prepared test sample.

In another aspect of the invention, there is provided antimicrobials prepared according to the method described above.

In a yet preferred embodiment, the antimicrobial agent is selected from one or more of the compounds shown in FIG. 6. Specifically, in some embodiments, the antimicrobial agent or compound is selected from the group consisting of DNM-111, DNM-112, DNM-113, DNM-114, DNM-115, DNM-116, DNM-117, DNM-118, DNM-141, DNM-142, DNM-143, DNM-144, DNM-145, DNM-121, DNM-122, DNM-123, DNM-124, DNM-125, DNM-126, DNM-121A, DNM-122A, DNM-123A, DNM-124A, DNM-121B, DNM-121C, DNM-124C, DNM-121D, DNM-122D, DNM-123D, DNM-121E, DNM-122E, DNM-123E, DNM-123F, DNM-121F, DNM-122F, DNM-121G, DNM-122G, DNM-123G, DNM-121H, DNM-122H, DNM-123H, DNM-121I, DNM-122I, DNM-123I, DNM-124I, DNM-125I, DNM-126I, DNM-121J, DNM-124J, DNM-131, DNM-133, DNM-132, DNM-131A, DNM-133A, DNM-132A, DNM-131B, DNM133B, DNM-132B, DNM-131C, DNM-133C, DNM-132C, DNM-131D, DNM-133D, DNM-132D, DNM-131E, DNM-132E, DNM-133E, DNM-131F, DNM-131G, DNM133G, DNM132G, DNM-131H, DNM-131I, DNM-133I, DNM-132I, DNM-131J5, DNM-132J, DNM-133J, DNM-131K, DNM-133K, DNM-132K, DNM-131L, DNM-133L, DNM-132L, DNM-131M, DNM-131N and DNM-131O.

It is of note that the synthesis of the compounds shown in FIG. 6 and listed above are described below. Furthermore, it is noted that the names for these compounds are provided below along with their 'DNM' designation. It is further noted that the chemical names of these compounds would be obvious to one of skill in the art on reviewing FIG. 6. Accordingly, it is to be understood that the 'DNM' numbers used herein may be used interchangeably with the corresponding structure shown in FIG. 6 or the proper chemical name, which as discussed above is either provided below or may be deduced from the structure using standard nomenclature rules known in the art.

In a yet preferred embodiment, the antimicrobial agents have a general formula as given in FIG. 5A wherein:
V, W, X, Y, and Z are independently selected from the group consisting of C, S, N, or O; P1 is independently selected from the group of tetrazole, 1-methyltetrazole, or 2-methyltetrazole, or 1-imino-methylamine; and P2 and P3 are independently selected from the group consisting of: —H, —COOH, —CONH$_2$, benzyl, phenyl or heterocycles (benzyl, phenyl, and heterocycles may contain additional mono- or multiply substituted halogens, methoxy, hydroxy, carboxy, and amido groups, and their relevant methyl or ethyl esters, in any combination), biphenyl, or naphthyl; with the additional specification that if P1 is tetrazole and P3 is benzyl or a heterocycle that a bond may exist between the nitrogen at the 1 position of tetrazole and the carbon at the position adjacent on the ring to P3's point of contact with Y.

In a still further preferred embodiment, the antimicrobial agent has a general formula as given in FIG. 5A wherein:
W, X, Y and Z are C
V is S
P1 is tetrazole, 1-methyltetrazole, or 2-methyltetrazole
P2 and P3 are phenyl or benzyl or a heterocycle, substituted as described above;
P2 and P3 ligands may be identical but are not necessarily identical In a preferred embodiment of the invention, there antimicrobial is selected from the group consisting of DNM-131, 123, 124, 141, or 131D. In another embodiment of the invention, the antimicrobial is selected from the group consisting of DNM-131, 123, 124, 141, 131D, 142, 121H, 122D, 123A, 123E, 123I, 131H, 131K, and 133E. In yet another embodiment of the invention, the antimicrobial is selected from the group consisting of DNM-131, 123, 124, 141, 131D, 142, 121H, 122D, 123A, 123E, 123I, 131H, 131K, 133E, 121G, 122G, 122H, 123D, 123F, 123G, 123H, 124A, 124I, 131A, 131C, 131E, 131F, 131I, 131J, 131O, 132A, 132C, 132G, 133A, and 133C.

It is of note that the above-described antimicrobials may be prepared to be administered in a variety of ways, for example, topically, orally, intravenously, intramuscularly, subcutaneously, intraperitoneally, intranasally or by local or systemic intravascular infusion using means known in the art and as discussed below.

It is of note that as discussed herein, the antimicrobial agents may be arranged to be delivered at a concentration of about 1 µM to about 50 mM; or 10 µM to 50 mM or 100 µM to 50 mM. As will be appreciated by one of skill in the art, this may be the effective concentration, that is, a sufficient dosage is administered such that a concentration within one of the envisioned ranges is attained at the required site. As will be apparent to one knowledgeable in the art, the total dosage will vary according to many factors, including but by no means limited to the weight, age and condition of the individual or patient.

In some embodiments, one or more of the above-described antimicrobial agents may be co-administered with one or more known antibiotics.

In some embodiments, one or more of the above-described antimicrobials at concentrations or dosages discussed above may be combined with a pharmaceutically or pharmacologically acceptable carrier, excipient or diluent, either biodegradable or non-biodegradable. Exemplary examples of carriers include, but are by no means limited to, for example, poly(ethylene-vinyl acetate), copolymers of lactic acid and glycolic acid, polylactic acid), gelatin, collagen matrices, polysaccharides, poly(D,L lactide), poly(malic acid), poly (caprolactone), celluloses, albumin, starch, casein, dextran, polyesters, ethanol, mathacrylate, polyurethane, polyethylene, vinyl polymers, glycols, mixtures thereof and the like. Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, polyvinylpyrrolidone, sugars and starches. See, for example, Remington: The Science and Practice of Pharmacy, 1995, Gennaro ed.

As will be apparent to one knowledgeable in the art, specific carriers and carrier combinations known in the art may be selected based on their properties and release characteristics in view of the intended use. Specifically, the carrier may be pH-sensitive, thermo-sensitive, thermo-gelling, arranged for sustained release or a quick burst. In some embodiments, carriers of different classes may be used in combination for multiple effects, for example, a quick burst followed by sustained release.

In other embodiments, one or more of the above-described antimicrobials at concentrations or dosages described above may be encapsulated for delivery. Specifically, the compounds may be encapsulated in biodegradable microspheres, microcapsules, microparticles, or nanospheres. The delivery vehicles may be composed of, for example, hyaluronic acid, polyethylene glycol, poly(lactic acid), gelatin, poly(E-caprolactone), or a poly(lactic-glycolic) acid polymer. Combinations may also be used, as, for example, gelatin nanospheres may be coated with a polymer of polylactic-glycolic) acid. As will be apparent to one knowledgeable in the art, these and other suitable delivery vehicles may be prepared according to protocols known in the art and utilized for delivery of the compounds.

It is of note that the above described antimicrobials may be combined with permeation enhancers known in the art for improving delivery. Examples of permeation enhancers include, but are by no means limited to those compounds described in U.S. Pat. Nos. 3,472,931; 3,527,864; 3,896,238; 3,903,256; 3,952,099; 4,046,886; 4,130,643; 4,130,667; 4,299,826; 4,335,115; 4,343,798; 4,379,454; 4,405,616; 4,746,515; 4,788,062; 4,820,720; 4,863,738; 4,863,970; and 5,378,730; British Pat. No. 1,011,949; and Idson, 1975, J. Pharm. Sci. 64:901-924.

In a preferred embodiment, an effective amount of one or more of the above-described antimicrobials may be used in the preparation of a medicament as described above for the treatment of a disease, disorder or condition caused by a pathogenic bacteria selected from the group including but by no means limited to Escherichia, Salmonella, Pseudomonas, Neisseria, Legionella, Haemophilus, Campylobacter, Helicobacter and Shigella.

In a preferred embodiment, an effective amount of one or more of the above-described agents may be used in the preparation of a medicament as described above for the treatment of a disease, disorder or condition selected from the group consisting of but by no means limited to gasteroeteritis, meningitis, pneumonia, septicaemia, urinary tract infections, gonorrhea; peptic ulcers and nosocomialinfections. As will be appreciated by one of skill in the art, the above conditions are often caused by pathogenic bacteria, for example, those pathogenic bacteria listed above. As such, administering an effective amount of one or more of the above-described antimicrobial agents or antimicrobial compounds to an individual or a patient in need of such treatment will have at least one of the following effects: inhibition of bacterial replication; reduction of colony forming units; reduction in severity of symptoms; longer periods of remission as well as improvement in other symptoms associated with the above-listed diseases which are well-known to one of skill in the art.

In some embodiments, the described antimicrobial agents are used as medicinal compounds, for example, for treating humans, or as veterinary compounds, for example, for treating animals, poultry, livestock and the like, as well as in aquaculture and agricultural applications.

While the preferred embodiments of the invention have been described above, it will be recognized and understood that various modifications may be made therein, and the appended claims are intended to cover all such modifications which may fall within the spirit and scope of the invention.

The invention will now be further described by way of examples. However, the examples are intended for illustrative purposes and do not necessarily limit the invention.

Pharmacophore Mapping of the LpxA Active Site

An x-ray structure is available for the LpxA enzyme of the lipid A pathway which is a UDP-N-acetylglucosamine acyltransferase. The available crystal structure (PDB code: 1LXA) (Raetz and Roderick, 1995) of LpxA is the solid ground for our rational design of the LpxA inhibitors, which are likely a new generation of novel antibiotics. LpxA is a trimer of identical subunits. We have devised a receptor model (see FIG. 4) of three binding sites between two subunits using standard molecular mechanics force fields and modeling software. Two of the three binding sites are Phe162 and Lys76 from one subunit, and the third binding site is Arg204 from an adjacent subunit.

On the basis of this proposed receptor model, we have designed a series of LpxA inhibitors using various molecular modeling techniques via an outside-in de novo approach. The general schematic of our designed inhibitors is given in FIG. 5A where V, W, X, Y, and Z can be independently either C, S, N, or O. Ligands P1, P2 and P3 constitute the three points of the proposed pharmacophore model. The binding mode of the designed compounds to the receptor model can be seen in FIG. 5B. The conformational analysis of the designed molecules was performed at semi-empirical PM3 and B3LYP/6-31G* levels of theory. The binding study of the designed compounds to the receptor model within the LpxA crystal structure was performed using molecular mechanics force fields and charges within standard modeling software. Each optimization varied the atomic positions of the designed compounds and the atoms within 10 angstroms of the binding site, while the bulk of the LpxA crystal structure was constrained. Distance-dependent solvation was included. All compounds were computed to have a favorable binding interaction with the active site. An example of the binding of the designed inhibitors to the designed receptor model in the LpxA crystal is given in FIG. 5C and an enlarged view of the binding region is shown in FIG. 5D. (The structures of the 87 compounds synthesized based on the preceding design strategies and used for enzyme and microbiological testing are shown in FIG. 6.)

LpxA Inhibition Studies

Preparation of E. coli LpxA and acyl-ACP Substrates

The lpxA gene was amplified from an E. coli genomic library and inserted into a pET23b vector using standard recombinant DNA methodology. The 5' oligonucleotide for amplification of the LpxA open reading frame was 5'-GACGGATCCATGATTGATAAATCCGCCTTTGTG-3' (SEQ ID NO. 1) and contains a BamHI restriction enzyme site upstream of the LpxA ATG start codon and the 3' oligonucleotide was 5'-GTGCTCGAGACGAATCAGACCGCGCGTTGAGCG-3' (SEQ ID NO. 2) and contains a XhoI restriction enzyme site downstream of the final codon of the LpxA open reading frame. Primers were custom synthesized. The primers were designed such that digestion of the amplification product would result in addition of a C-terminal 6x-His tag in frame with the LpxA open reading frame. Specifically, E. coli genomic DNA was isolated and an amplification reaction was carried out as follows: 33 µl water, 5 µl 10x reaction buffer, 1.5 µl of 50 mM magnesium sulfate, 3 µl of 10 mM dNTPs, 3

μl of a 50 μM solution of the 5' LpxA primer, 3 μl of a 50 μM solution of the 3' LpxA primer, 0.5 μl of *E. coli* genomic DNA solution, and 1 μl of polymerase. The reaction conditions were as follows: 94° C. for 2 minutes; followed by 30 cycles of 94° C. for 30 seconds, 50° C. for 30 seconds, 68° C. for 1.5 minutes, followed by an extension at 68° C. for 7 minutes. The resulting LpxA product was separated from other DNA on a 0.8% agarose gel and isolated from the gel. The LpxA open reading frame was cloned into a topoisomerase I-activated vector and transformed into *E. coli*. The DNA sequence of the product inserted in the vector was sequenced and was found to be identical to the known *E. coli* LpxA open reading frame. The newly synthesized plasmid containing the BamHI- and XhoI-flanked LpxA open reading frame and plasmid pET23a were digested with BamHI and XhoI at 37° C. for 2 hours, DNA was separated by agarose gel electrophoresis, isolated from the gel, and ligated. Ligation reactions were transformed into chemically competent *E. coli* and plasmid DNA was isolated. Restriction mapping was performed to determine which plasmids contained the LpxA open reading frame. To remove the T7 epitope coding sequence from the 5'end of the LpxA open reading frame, the pET23a plasmid containing the LpxA open reading frame was digested with the restriction enzymes BamHI and XhoI and a pET23b plasmid was digested with BglII and XhoI, DNA was separated by agarose gel electrophoresis, isolated from the gel, and ligated. Ligation reactions were transformed into chemically competent *E. coli* and plasmid DNA was isolated. Restriction mapping was performed to assess plasmids containing the LpxA open reading frame.

A 5 ml culture of *E. Coli* BL21 cells expressing the LpxA-6×His plasmid was grown overnight at 37° C. in LB medium containing 50 μg/ml ampicillin and 34 μg/ml chloramphenicol, then subcultured into 500 ml of the same medium and grown at 37° C. until $A_{600}$=0.6. LpxA expression was induced by addition of 0.5 mM IPTG for three hours. The cells were centrifuged at 7 000×g for 10 minutes at 4° C. and lysed using a mild, nonionic detergent. The soluble fraction containing LpxA was added to 1 ml of nickel affinity resin in a 15 ml Falcon tube; the resin was washed extensively with extraction/wash buffer (50 mM Na-phosphate (pH 7.0) and 300 mM NaCl) prior to use. This mixture was incubated on a rotating platform at low speed for 20 minutes at room temperature. The resin was centrifuged at 1000 rpm in a bench top centrifuge for 2 min, washed twice (10 min each) with 10 ml of extraction/wash buffer, resuspended in 10 ml of extraction/wash buffer, and transferred to a 10 ml polypropylene disposable protein purification column. The column was eluted with 5 ml of 50 mM Na-phosphate (pH 7.0) containing 300 mM NaCl and 150 mM imidazole, collected in 1 ml fractions. The eluate was analysed by SDS-PAGE and was visualised using a protein stain (FIG. 7 inset).

Recombinant *Vibrio harveyi* acyl carrier protein was prepared from a GST fusion protein as described previously (Flaman et al., 2001). Acyl-ACP substrate was prepared by incubation of 55 μM ACP, 10 mM Mg-ATP, 2 mM DTT, 80 μM □-hydroxymyristic acid, and 50 mU of *V. harveyi* acyl-ACP synthetase in 0.1 M Tris-HCl (pH 7.8) in a total volume of 400 μl for 18 h at 37° C. (Shen et al., 1992). The acyl-ACP product was partially purified from fatty acid and other reagents by application to an anion-exchange spin column in 25 mM Tris-HCl (pH 7.8) and elution with 0.5 M NaCl in the same buffer.

LpxA Assay

Measurement of LpxA activity was based on increased mobility of radiolabelled UDP-N-acetyl-D-glucosamine on thin layer chromatography (TLC) plates upon acylation (Wyckoff and Raetz, 1999). Stock solutions (50 mM) of all test compounds were prepared in ethanol or DMSO and stored at 4° C. Briefly, 1 μl of test compound of appropriate dilution in ethanol or DMSO was mixed with 2.5 μM □-hydroxymyristoyl-ACP and 0.5 μM *E. coli* LpxA in 1% bovine serum albumin and 40 mM Na-HEPES (pH 8.0) at room temperature (total volume 8 μl). The reaction was initiated by adding 2 μl of UDP-[$^3$H]N-acetyl-D-glucosamine (final concentration 0.8 μM, 7.9 Ci/mmol) and 2 μl aliquots were removed at various time intervals and spotted directly on TLC plates. TLC plates were developed in $CHCl_3$:MeOH:acetic acid:$H_2O$ (25:15:2:4) and radioactivity associated with the acyl-UDP-GlcNAc product ($R_f$~0.4) was measured using a scanner. The LpxA assay was validated based on its specificity for β-hydroxymyristoyl-ACP, as myristoyl-ACP was inactive in the reaction (FIG. 7).

Effects of Inhibitors on LpxA Activity

All compounds were tested initially for inhibition of recombinant *E. coli* LpxA in vitro. As shown in FIG. 8, 26 compounds (123, 124, 131, 141, 121G, 122G, 122H, 123D, 123F, 123G, 123H, 124A, 124I, 131A, 131C, 131D, 131E, 131F, 131I, 131J, 131O, 132A, 132C, 132G, 133A, and 133C) produced >80% inhibition of LpxA activity at a concentration of 5 mM, while nine additional compounds (142, 121H, 122D, 123A, 123E, 123I, 131H, 131K, and 133E) also exhibited significant inhibitory activity, but to a lesser extent (>70% inhibition). Other compounds did not appear to significantly block LpxA activity under these conditions.

Based on the above results, the dose dependence of LpxA inhibition was investigated for compounds 123, 124, 131, 141, 122G, 123G, 123I, 124A, 131A, 131C, 131D, 131E, 131F, 131G, 131H, 131I, 131J, 131K, and 131O (FIG. 9). Compound 131 was the most potent, producing almost complete inhibition of LpxA activity at concentrations above 500 μM. Compound 123 exhibited approximately 60% inhibition at 500 μM, while all other compounds tested were only effective at the highest concentration tested. No compound appeared to be an effective LpxA inhibitor in the concentration range of 5-50 μM.

In Vivo Lipopolysaccharide (LPS) Synthesis

LpxA catalyzes the first step in the synthesis of lipid A (the hydrophobic anchor of LPS), which is essential for the growth and pathogenesis of many gram-negative bacteria. The inhibition of LpxA activity would therefore result in decreased synthesis of LPS. To measure the synthesis of LPS in vivo, the incorporation of radiolabelled galactose into acid-precipitable material was determined. The *E. coli* strain used for these studies was D22 (obtained from the *E. coli* Genetic Stock Center), which contains a mutation in the LpxC gene (lpxC101; Normark et al., 1969, J Bacteriol 97, 1334). Strains harbouring this mutation have an increased susceptibility to antibiotics, in addition to producing approximately 30% less LPS (Grundstrom et al., 1980, J Bacteriol 144, 884.). Bacteria were grown in Luria broth to early-log phase, at which point, 500 μl was transferred to a culture tube containing 1 μl of [$^3$H]galactose (final concentration, 0.2 mM, 20 μCi/μmol) and mixed. Cultures were incubated at 30° C. for 75 minutes with shaking at 220 rpm. Incorporation was terminated by adding 400 μl of labelled culture to 44.4 μl of 100% trichloroacetic acid (TCA, 10% final concentration) in a 1.5 ml microcentrifuge tube. Tubes were vortexed, incubated on ice for 30 minutes, then centrifuged at 14 000 rpm for 5 minutes at room temperature. The pellet was rinsed twice with 1 ml of ice-cold 10% TCA, resuspended in 50 μl of formic acid, and transferred to a scintillation vial for counting.

Effects of Inhibitors on In Vivo LPS Synthesis

Compounds that effectively inhibited in vitro LpxA activity were subsequently screened for their ability to block [$^3$H] galactose incorporation into acid-precipitable material in living cells. Compounds to be tested were dissolved in DMSO and added to the bacterial culture prior to labelling with galactose, and LPS synthesis was determined as described previously. The final concentration of DMSO (1%, v/v) had minimal effect on LPS synthesis. As shown in FIG. 10A, five compounds (122G, 124A, 131, 131D, and 131K) decreased LPS synthesis >90% at a concentration of 1 mM, while one other compound (131I) also decreased LPS synthesis, but to a lesser extent (~80%). Compounds 131 and 131D were further tested at a concentration of 0.1 mM, which resulted in decreases in LPS synthesis of approximately 70% and 50%, respectively (FIG. 10B).

Microbiological Testing

Inhibition of *E. coli* Growth

Compounds that showed significant inhibition of LpxA activity were further evaluated for their ability to inhibit growth of either *E. coli* strain BL21 or D22 in liquid culture (FIG. 11). Compounds to be tested were dissolved in ethanol or DMSO and subsequently diluted into of Luria broth. The final concentration of ethanol (2%, v/v) or DMSO (1%, v/v) had minimal effect on growth rate. Culture tubes were subsequently inoculated with *E. coli* BL21 or D22 cells to an optical density (at 600 nm) of 0.01 and incubated on a rotary shaker at 37° C. The optical density at 600 nm of 100 µl samples was measured at indicated time points.

Compound 131 exhibited greatest potency in this assay: no growth of *E. coli* was observed in the presence of 0.1 or 1 mM 131, and partial inhibition was observed even at 10 µM. Substantial growth inhibitory activity of compounds 123 and 124 were noted only at the highest concentration tested (1 mM), while no apparent effect of compound 141 was observed in this assay (FIG. 11). These results indicate that the potency of these compounds as growth inhibitors in vivo correlates with (and may even exceed) their in vitro activity on LpxA, likely due to the sensitivity of *E. coli* growth to even partial inhibition of lipid A biosynthesis (Wyckoff et al., 1998).

Inhibition of Growth Versus a Panel of Clinical Bacterial Isolates

All clinical isolates tested were from The North American Urinary Tract Infection Collaborative Alliance (NAUTICA) which is a UTI surveillance study involving 40 medical centres (30 from the US and 10 from Canada). Each centre submitted up to 50 consecutive outpatient midstream urine isolates. All isolates were deemed significant urinary tract pathogens by individual laboratory criteria and identified to the species level by each laboratory's existing protocol. Isolates were transported to the coordinating laboratory (Health Sciences Centre, Winnipeg, Canada) on charcoal swabs. Only one isolate per patient was accepted. Upon receipt, isolates were cultured by the coordinating laboratory, stocked in skim milk, and stored at −80° C. awaiting reference antibiotic susceptibility testing. Elementary demographic information was also compiled for each isolate. Isolates were selected randomly from the above pool to represent 18 different species of Enterobacteriaceae and non-Enterobacteriaceae. An average of 5 strains of each species were tested for a total of 93 organisms. In addition, 23 reference (ATCC) [both gram negative and gram positive] strains were tested.

Susceptibilities to the compounds were determined using the National Committee for Clinical Laboratory Standards (NCCLS) M7-A6 broth microdilution method. Cation-adjusted Mueller-Hinton broth ($Ca^{2+}$, 25 µg/ml; $Mg^{2+}$, 12.5 µg/ml) microdilution panels were prepared to contain antimicrobial doubling dilution concentrations ranging from 0.25 µg/ml-256 µg/ml depending on the solubility of the compound at the high concentrations. DMSO controls were incorporated into the panel to mimic the quantity of DMSO used in dissolving some of the compounds at the higher concentrations. Each final panel well volume was 100 µl with a bacterial inoculum of $5 \times 10^5$ colony forming units (CFU)/ml. Panels were read following 16 to 20 hours of incubation at 35° C. in ambient air. The minimum inhibitory concentration (MIC) was defined as the lowest concentration of antimicrobial inhibiting visible growth. Quality control (QC) was performed using four ATCC QC organisms that were run with every batch set up to insure reproducibility.

Synthetic Strategy of LpxA Inhibitors

The drug molecules are multiple substituted aromatic compounds. The introduction of various substitutents can be furnished by traditional methods. For example, aryl substitutents can be introduced by cross coupling reactions such as Stille, Suzuki, and Negishi. Tetrazolyl groups are furnished by reaction of cyano group and sodium azide. The synthetic strategies are illustrated by example in the methods denoted A-G (FIGS. 12-18). The structures of the 87 compounds synthesized based on the preceding design strategies and used for enzyme and microbiological testing are shown in FIG. 6.

EXAMPLE 1

Synthesis of 3-(1-H-tetrazol-5-yl)thiophene-2,5-dicarboxylic acid analogues

Method A (FIG. 12) was used to synthesize 3-(1-H-tetrazol-5-yl)thiophene-2,5-dicarboxylic acid analogues. The commercially available thiophene-2,5-dicarboxylic acid was converted into its dimethyl ester by refluxing in dry methanol with catalytic amount of sulfuric acid. The resulting dimethyl ester was brominated by NBS in TFA and sulfuric acid. The bromide was transferred to nitrile using the typical procedure, and further converted into tetrazole by sodium azide in the presence of triethylamine hydrochloride salt at 70° C. in DMF. The methylation of tetrazole nitrogen using the traditional method gave both 1- and 2-methylated products.

Dimethyl thiophene-2,5-dicarboxylate To a stirred suspension of thiophene-2,5-dicarboxylic acid (6.886 g, 40 mmol) in 40 mL of dry methanol was added 1 mL of sulfuric acid, and the reaction was refluxed for 48 hours. After cooled to room temperature, the reaction mixture was put in refrigerator overnight. The solid was collected by suction filtration, washed with methanol, and dried under vacuum. 7.737 g (96.6%) of product was obtained as a white solid, mp 146.0-148.0° C. [lit. mp: 148-149° C. (Nippon Kagaku Kaishi 1987, (7), 1424-9), 142-146° C. (Khimiya Geterotsiklicheskikh Soedinenii 1986, (6), 826-36)].

Dimethyl 3-cyanothiophene-2,5-dicarboxylate To a stirred solution of dimethyl thiophene-2,5-dicarboxylate (2.00 g, 10.0 mmol) in 5 mL of TFA and 2 mL of concentrated sulfuric acid was added 2.67 g (15.0 mmol) of NBS in portions during 1 hour. After being stirred overnight, the reaction mixture was poured into ice water, and extracted with dichloromethane. The organic phase was dried over anhydrous sodium sulfate and concentrated. After drying under vacuum, the solid was dissolved in 25 mL of DMF under argon. CuCN (1.79 g, 20 mmol) was added. The reaction mixture was refluxed for 5 hours, quenched with 1N HCl after cooling to room temperature, and extracted with ethyl acetate. The organic layer was washed with brine, dried over anhydrous sodium sulfate, and concentrated. The crude product was purified by flash chromatography (hexane:EtOAc=7:2). 1.757 g (78%) of product was obtained as a white solid, mp 111.0-112.0° C.; $^1$H NMR (CDCl$_3$, 500 MHz) δ 3.96 (s, 3H), 4.01 (s, 3H), 7.94 (s, 1H); $^{13}$C NMR (CDCl$_3$, 125 MHz) δ 53.22, 53.48, 112.75, 114.33, 135.54, 138.87, 144.23, 159.54, 160.41.

3-Cyanothiophene-2,5-dicarboxylic acid Dimethyl 3-cyanothiophene-2,5-dicarboxylate (638 mg, 2.84 mmol) was dissolved in 10 mL of methanol and 8 mL of THF. A solution of lithium hydroxide (340 mg, 14.2 mmol) in 3 mL of H$_2$O was added. The reaction was stirred at room temperature until all starting material was consumed. After removal of the solvent, the residue was redissolved in H$_2$O, acidified with 1N HCl, and extracted with ethyl acetate. The organic layer was dried over anhydrous sodium sulfate, and concentrated. 564 mg (100%) of product was obtained as a white solid. $^1$H NMR (DMSO, 500 MHz) δ 8.15 (s, 1H), 14.28 (2H, broad); $^{13}$C NMR (DMSO, 125 MHz) δ 113.76, 113.83, 136.35, 140.36, 146.53, 160.78, 161.85.

3-(1H-tetrazol-5-yl)thiophene-2,5-dicarboxylic acid (DNM-111) A reaction mixture of 3-cyanothiophene-2,5-dicarboxylic acid (398.7 mg, 2.02 mmol), NaN$_3$ (262.3 mg, 4.04 mmol) and Et$_3$N.HCl (555.5 mg, 4.04 mmol) in 7.5 mL of DMF was stirred at 70° C. for 20 hours. After being cooled to room temperature, the reaction was quenched with 1N HCl and extracted with ethyl acetate. The organic layer was dried over anhydrous sodium sulfate, concentrated, and the crude product was purified by recrystallization in methanol. 400 mg (82%) of product was obtained as a white powder, mp: slowly decomposed; $^1$H NMR (D$_2$O, 500 MHz) δ 7.89 (s, 1H); $^{13}$C NMR (D$_2$O, 125 MHz) δ 168.71, 168.02, 153.35, 144.02, 143.54, 131.36, 124.98.

3-(1-Methyl-1H-tetrazol-5-yl)-thiophene-2,5-dicarboxylic acid dimethyl ester (DNM-115), and 3-(2-methyl-2H-tetrazol-5-yl)-thiophene-2,5-dicarboxylic acid dimethyl ester (DNM-114) To a stirred suspension of 3-(2H-tetrazol-5-yl) thiophene-2,5-dicarboxylic acid (172 mg, 0.72 mmol) and potassium carbonate (846 mg, 6.13 mmol) in 7 mL of DMF was added methyl iodide (0.38 mL, 6.13 mmol) under argon. The reaction was stirred overnight at room temperature, diluted with ethyl acetate, and filtered. The filtrate was washed with H$_2$O, dried over anhydrous sodium sulfate, and concentrated. Purification by flash chromatography (hexane:ethyl acetate=1:1) afforded 115 mg (56.9%) of 3-(2-Methyl-2H-tetrazol-5-yl)-thiophene-2,5-dicarboxylic acid dimethyl ester [white solid, mp: 121.0-122.0° C.; $^1$H NMR (DMSO, 500 MHz) δ 8.00 (s, 1H), 4.45 (s, 3H), 3.90 (s, 3H), 3.81 (s, 3H); $^{13}$C NMR (DMSO, 125 MHz) δ 161.21, 160.91, 159.34, 137.00, 136.56, 135.05, 132.15, 53.52, 53.48, 40.19] and 73 mg (36.1%) of 3-(1-Methyl-1H-tetrazol-5-yl)-thiophene-2,5-dicarboxylic acid dimethyl ester [white solid, mp: 149.0-151.0° C.; $^1$H NMR (CDCl$_3$, 500 MHz) δ 7.85 (s, 1H), 3.96 (s, 3H), 3.95 (s, 3H), 3.86 (s, 3H); $^{13}$C NMR (CDCl$_3$, 125 MHz) δ 160.97, 160.38, 149.79, 138.80, 137.65, 135.04, 128.69, 53.21, 53.08, 34.38].

3-(2-Methyl-2H-tetrazol-5-yl)-thiophene-2,5-dicarboxylic acid (DNM-112) A solution of 3-(2-Methyl-2H-tetrazol-5-yl)-thiophene-2,5-dicarboxylic acid dimethyl ester (75 mg, 0.27 mmol) and lithium hydroxide (31.5 mg, 1.33 mmol) in 3 mL of methanol and 1 mL of H$_2$O was stirred overnight at room temperature. The solvent was removed, and the residue was dissolved in 5 mL of H$_2$O. After acidified with 1N HCl, the precipitate formed was collected by suction filtration, washed with H$_2$O, and dried under vacuum overnight. 55 mg (81%) of product was obtained as a white solid, mp: 248.0-250.0° C. (decomposed); $^1$H NMR (DMSO, 500 MHz) δ 13.54 (broad, 2H), 7.84 (s, 1H), 4.44 (s, 3H); $^{13}$C NMR (DMSO, 125 MHz) δ 162.37, 162.00, 159.75, 138.90, 138.55, 134.72, 131.47, 41.00.

3-(1-Methyl-1H-tetrazol-5-yl)-thiophene-2,5-dicarboxylic acid (DNM-113) A solution of 3-(1-methyl-1H-tetrazol-5-yl)-thiophene-2,5-dicarboxylic acid dimethyl ester (50 mg, 0.18 mmol) and lithium hydroxide (21.2 mg, 0.89 mmol) in 3 mL of methanol and 1 mL of H$_2$O was stirred overnight at room temperature. The solvent was removed, and the residue was dissolved in 5 mL of H$_2$O. After being acidified with 1N HCl, the precipitate formed was collected by suction filtration, washed with H$_2$O, and dried under vacuum overnight 31.5 mg (70%) of product was obtained as a white solid, mp: 256.0-258.0° C. (decomposed); $^1$H NMR (DMSO, 500 MHz) δ 7.88 (s, 1H), 3.91 (s, 3H); $^{13}$C NMR (DMSO, 125 MHz) δ 161.82, 161.14, 149.98, 139.68, 139.08, 134.96, 127.84.

4-(2H-Tetrazol-5-yl)-thiophene-2-carboxylic acid (DNM-116) A mixture of 3-cyanothiophene-2,5-dicarboxylic acid (49 mg, 0.25 mmol), NaN$_3$ (32.5 mg, 0.5 mmol) and zinc bromide (113 mg, 0.5 mmol) in 2 mL of dry DMF was stirred at 120° C. overnight. After cooling to room temperature, the reaction was quenched with 1N HCl, and extracted with ethyl acetate. The organic layer was dried over anhydrous sodium sulfate, concentrated, and the crude product was purified by flash chromatography (EtOAc:AcOH=20:1) 40 mg (82%) of product was obtained as a white powder, mp: 260.0-263.0° C. (decomposed); $^1$H NMR (DMSO, 500 MHz) δ 14.89 (broad, 1H), 8.56 (d, J=1.37 Hz, 1H), 8.21 (d, J=1.37 Hz, 1H); $^{13}$C NMR (DMSO, 125 MHz) δ 162.92, 151.82, 137.55, 134.00, 131.64, 126.37.

3-Cyanothiophene-2,5-dicarboxamide 3-Bromothiophene-2,5-dicarboxamide (354 mg, 1.42 mmol) and CuCN (255 mg, 2.85 mmol) was dissolved in 5 mL of DMF. The reaction mixture was heated to 120° C.; and the progress of the reaction was monitored by TLC until complete (~5 h). The solution was diluted with 1N HCl, and extracted with ethyl acetate. The organic layer was dried over anhydrous sodium sulfate, and concentrated. The residue was purified by flash chromatography (THF:hexane:MeOH=20:20:1) and 160 mg (58%) of product was obtained as a white solid, mp: 240-242° C. (decomposed) $^1$H NMR (DMSO, 500 MHz) δ 7.87 (1H, broad), 7.96 (1H, broad), 8.08 (s, 1H), 8.20 (1H, broad), 8.27 (1H, broad); $^{13}$C NMR (DMSO, 125 MHz) δ 111.05, 113.88, 130.48, 143.24, 148.05, 160.00, 160.97.

3-(1H-tetrazol-5-yl)thiophene-2,5-dicarboxamide (DNM-117) A reaction mixture of 3-cyanothiophene-2,5-dicarboxamide (99.7 mg, 0.51 mmol), NaN$_3$ (66.5 mg, 1.02 mmol) and Et$_3$N.HCl (140 mg, 1.02 mmol) in 5 mL of DMF was stirred at 70° C. for 20 hours. After being cooled to room temperature, the reaction was quenched with 1N HCl and extracted with ethyl acetate. The organic layer was dried over anhydrous sodium sulfate, concentrated, and the crude product was purified by recrystallization in methanol. 103 mg (85%) of product was obtained as a white powder, mp: slowly decomposed; $^1$H NMR (DMSO, 500 MHz) δ 7.72 (broad, 1H), 7.97 (broad, 1H), 8.19 (s, 1H), 8.28 (broad, 1H), 8.78 (broad, 1H); $^{13}$C NMR (DMSO, 125 MHz) δ 124.90, 130.55, 141.94, 142.57, 152.14, 162.11, 162.23.

EXAMPLE 2

Synthesis of 5-(4-fluorophenyl)-4-(1-H-tetrazol-5-yl) thiophene-2-carboxylic acid analogues Method B (FIG. 13) was used to synthesize 5-(4-fluorophenyl)-4-(1-H-tetrazol-5-yl)thiophene-2-carboxylic acid and analogues. The synthesis started from commercially available ethyl thiophene-2-carboxylate, which was dibrominated at C4 and C5 by NBS in a solvent mixture of TFA and sulfuric acid. The resulting ethyl 4,5-dibromothiophene-2-carboxylate was selectively cross-coupled at C5 with organozinc reagents. The left bromo at C4 was converted into tetrazolyl through nitrile. The methylation of tetrazole nitrogen using the traditional method gave both 1- and 2-methylated products.

Ethyl 4,5-dibromothiophene-2-carboxylate To a stirred solution of ethyl thiophene-2-caroxylate (12.62 g, 80.8 mmol) in 12 mL of sulfuric acid and 40 mL of TFA was added NBS (32.00 g, 177.8 mmol) in portions during 2-3 hours. After stirring overnight at room temperature, the reaction mixture was poured into ice water. The white precipitate formed was collected by suction filtration, and purified by recrystallization in methanol. 23.38 g (92%) of product was obtained as a white solid, mp: 47.0-48.0 (lit. mp 48.0-49.0° C., Bull. Chem. Soc. Jpn. 1991, 64 (8), 2566-8)

Ethyl 4-bromo-5-(4-fluorophenyl)thiophene-2-carboxylate To a stirred solution of ethyl 4,5-dibromothiophene-2-carboxylate (3.142 g, 10.0 mmol) and Pd(PPh$_3$)$_4$ (462 mg, 0.4 mmol) in 40 mL of THF was added a THF solution of 4-fluorophenylzinc bromide (30 mL of 0.5 M solution, 15.0 mmol) under argon. The reaction was stirred at 50° C. for 4 hours, cooled to room temperature, quenched with saturated ammonium chloride, and extracted with ethyl acetate (50 mL×2). The combined ethyl acetate phase was dried over anhydrous sodium sulfate, concentrated, and the residue was purified by flash chromatography (hexane:ethyl ether=100:4). 2.14 g (65%) of product was obtained as a white solid, mp: 70:0-71.0° C., $^1$H NMR (CDCl$_3$, 500 MHz) δ 7.72 (s, 1H), 7.63 (m, 2H), 7.15 (m, 2H), 4.37 (q, J=7.14, 2H) 1.38 (t, J=7.14, 314); $^{13}$C NMR (CDCl$_3$, 125 MHz) δ 164.19, 162.20, 161.15, 143.84, 136.88, 132.49, 131.03, 130.96, 128.19, 128.16, 115.94, 115.77, 108.12, 61.64, 14.29.

4-Cyano-5-(4-fluoro-phenyl)-thiophene-2-carboxylic acid ethyl ester The reaction mixture of ethyl 4-bromo-5-(4-fluorophenyl)thiophene-2-carboxylate (1.682 g, 5.14 mmol) and copper(I) cyanide (0.920 g, 10.58 mmol) in 20 mL of DMF was refluxed overnight. After being cooled to room temperature, the reaction mixture was diluted with ethyl acetate. The precipitate formed was removed by filtration. The filtrate was washed with 1N HCl and brine, and dried over anhydrous sodium sulfate. After concentration, the residue was purified by flash chromatography (hexane:dichloromethane=1:1). 1.19 g (85%) of product was obtained as a white solid, mp: 94.5-95.4° C.; $^1$H NMR (CDCl$_3$, 500 MHz) δ 7.91 (s, 1H), 7.78 (m, 2H), 7.21 (m, 2H), 4.40 (q, J=7.14, 2H), 1.40 (t, J=7.14, 3H); $^{13}$C NMR (CDCl$_3$, 125 MHz) δ 165.12, 163.11, 160.55, 157.42, 135.54, 133.52, 130.02, 129.95, 126.90, 126.87, 116.81, 116.63, 114.72, 106.72, 62.09, 14.26.

5-(4-Fluoro-phenyl)-4-(1H-tetrazol-5-yl)-thiophene-2-carboxylic acid ethyl ester (DNM-124) The reaction mixture of 4-cyano-5-(4-fluoro-phenyl)-thiophene-2-carboxylic acid ethyl ester (718 mg, 2.63 mmol), sodium azide (342 mg, 5.26 mmol) and zinc bromide (1.185 g, 5.26 mmol) in 10 mL of DMF was refluxed overnight. After being cooled to room temperature, the reaction mixture was quenched with 1N HCl and extracted with ethyl acetate. The organic layer was washed with brine and dried over anhydrous sodium sulfate. After removal of the solvent, the residue was purified by flash chromatography (hexane:ethyl acetate:methanol:acetic acid=100:50:15:3). 662 mg (77%) of product was obtained as a white solid, mp: 208.0-210.0° C.; $^1$H NMR (DMSO, 500 MHz) δ 8.18 (s, 1H), 7.55 (m, 2H), 7.30 (m, 2H), 4.36 (q, 2H), 1.34 (t, 3H); $^{13}$C NMR (DMSO, 125 MHz) δ 163.78, 161.81, 160.56, 151.31 (broad), 149.12, 134.48, 132.52, 131.60, 131.53, 127.70, 127.67, 121.82 (broad), 115.79, 115.61, 61.50, 14.05.

5-(4-Fluoro-phenyl)-4-(1H-tetrazol-5-yl)-thiophene-2-carboxylic acid (DNM-121) A solution of 5-(4-Fluoro-phenyl)-4-(1H-tetrazol-5-yl)-thiophene-2-carboxylic acid ethyl ester (250 mg, 0.79 mmol) and lithium hydroxide (95 mg, 3.97 mmol) in 10 mL of methanol and 3 mL of H$_2$O was stirred overnight at room temperature. The solvent was removed, and the residue was redissolved in 10 mL of H$_2$O. After being acidified with 1N HCl, the precipitate formed was collected by suction filtration and recrystallized in a mixture solvent of ethanol and ether. 218 mg (95%) of product was obtained as a white solid, mp: 266.0-267.0° C. (decomposed); $^1$H NMR (DMSO, 500 MHz) δ 8.10 (s, 1H), 7.54 (m, 2H), 7.30 (m, 2H); $^{13}$C NMR (DMSO, 125 MHz) δ 163.71, 162.02, 161.74, 151.12 (broad) 148.72, 134.26, 134.08, 131.55, 131.48, 127.91, 127.88, 121.64 (broad), 115.76, 115.58.

Ethyl 5-(4-fluorophenyl)-4-(1-methyl-1H-tetrazol-5-yl) thiophene-2-carboxylate (DNM-126) and ethyl 5-(4-fluorophenyl)-4-(2-methyl-2H-tetrazol-5-yl)thiophene-2-carboxylate (DNM-125) To a stirred suspension of 5-(4-fluorophenyl)-4-(1H-tetrazol-5-yl)-thiophene-2-carboxylic add ethyl ester (200 mg, 0.63 mmol) and potassium carbonate (175 mg, 1.27 mmol) in 5 mL of dry DMF was added methyl iodide (99 µL, 1.58 mmol). The reaction was stirred overnight, diluted with ethyl acetate, and filtered. The filtrate was washed with H$_2$O and brine, dried over anhydrous sodium sulfate, and concentrated. The flash chromatography purification afforded 145 mg (69.7%) of ethyl 5-(4-fluorophenyl)-4-(2-methyl-2H-tetrazol-5-yl)thiophene-2-carboxylate [white solid, mp: 108.0-110.0° C.; $^1$H NMR (DMSO, 500 MHz) δ 8.11 (s, 1H), 7.59 (m, 2H), 7.29 (m, 2H), 4.35 (m, 5H), 1.33 (t, J=7.11 Hz, 3H); $^{13}$C NMR (DMSO, 125 MHz) δ 163.66, 161.69, 160.62, 159.78, 147.98, 134.24, 132.43, 131.70, 131.63, 127.99, 127.96, 124.48, 115.62, 115.44, 61.42, 39.54, 14.03] and 60 mg (28.8%) of ethyl 5-(4-fluorophenyl)-4-(1-methyl-1H-tetrazol-5-yl)thiophene-2-carboxylate [white solid, mp: 132.0-133.0° C.; $^1$H NMR (DMSO, 500 MHz) δ 8.13 (s, 1H), 7.37 (m, 2H), 7.27 (m, 2H), 4.36 (t, J=7.09 Hz, 2H), 3.83 (s, 3H), 1.33 (t, J=7.09 Hz, 3H); $^{13}$C NMR (DMSO, 125 MHz) δ 163.75, 161.78, 160.54, 150.32, 149.73, 135.10, 132.64, 130.79, 130.72, 128.80, 128.27, 127.46, 127.43, 120.47, 116.32, 116.14, 61.51, 34.14, 14.05].

5-(4-fluorophenyl)-4-(2-methyl-2H-tetrazol-5-yl) thiophene-2-carboxylic acid (DNM-123) Ethyl 5-(4-fluorophenyl)-4-(4-methyl-2H-tetrazol-5-yl)thiophene-2-carboxylate (94 mg, 0.28 mmol) was dissolved in 3 mL of methanol and 3 mL of THF. A solution of lithium hydroxide (34 mg, 1.42 mmol) in 1 mL of H$_2$O was added. The reaction was stirred overnight at room temperature. The solvent was removed, and the residue was redissolved in 5 mL of H$_2$O. After being acidified with 1N HCl, the white precipitate formed was collected by suction filtration and dried under vacuum. 82 mg (95%) of product was obtained as a white solid, mp: 219.0-221.0° C. (decomposed); $^1$H NMR (DMSO, 500 MHz) δ 13.52 (s, 1H), 8.05 (s, 1H), 7.58 (m, 2H), 7.28 (m, 2H); $^{13}$C NMR (DMSO, 125 MHz) δ 163.58, 162.09, 161.62, 159.91, 147.56, 134.11, 133.76, 131.67, 131.60, 128.23, 128.20, 124.40, 115.58, 115.40, 39.53.

5-(4-fluorophenyl)-4-(1-methyl-1H-tetrazol-5-yl) thiophene-2-carboxylic acid (DNM-122) Ethyl 5-(4-fluorophenyl)-4-(1-methyl-1H-tetrazol-5-yl)thiophene-2-carboxylate (42 mg, 0.13 mmol) was dissolved in 3 mL of methanol. A solution of lithium hydroxide (15 mg, 0.63 mmol) in 1 mL of H₂O was added. The reaction was stirred overnight at room temperature. The solvent was removed, and the residue was redissolved in 5 mL of H₂O. After being acidified with 1N HCl, the white precipitate formed was collected by suction filtration and dried under vacuum. 35 mg (91%) of product was obtained as a white solid, mp: slowly at decomposed 150° C.; $^1$H NMR (DMSO, 500 MHz) δ 13.60 (s, 1H), 8.04 (s, 1H), 7.36 (m, 2H), 7.27 (m, 2H); $^{13}$C NMR (DMSO, 125 MHz) δ 164.25, 162.56, 162.27, 150.45, 150.41, 135.18, 135.00, 131.33, 131.26, 128.25, 128.22, 120.91, 116.84, 116.67, 34.71.

The following compounds were prepared using the same method above:

5-(3-Fluorophenyl)-4-(1H-tetrazol-5-yl)thiophene-2-carboxylic acid (DNM-121A) $^1$H NMR (500 MHz, DMSO) δ 6.53-6.61 (m, 2H), 6.64 (d, J=9.16 Hz, 1H), 6.74 dd, J₁=6.87, J₂=12.97, 1H), 7.30 (s, 1H), 12.40 (broad, 1H); $^{13}$C NMR (125 MHz, DMSO) δ 116.13, 116.29, 116.31, 116.46, 125.48, 125.50, 127.76, 130.78, 130.85, 133.62, 133.68, 134.17, 134.80, 148.02, 160.88, 162.06, 162.82.

5-(3-Fluorophenyl)-4-(1-methyl-1H-tetrazol-5-yl) thiophene-2-carboxylic acid (DNM-122A) $^1$H NMR (500 MHz, DMSO) δ 3.47 (s, 3H), 6.41 (d, J=6.90 Hz, 1H), 6.44 (d, J=8.74 Hz, 1H), 6.56 (dt, J=2.03, J₂=7.61, 1H), 6.71 (dd, J=7.25, J₂=12.69, 1H), 7.26 (s, 1H), 12.30 (broad, 1H); $^{13}$C NMR (125 MHz, DMSO) δ 34.31, 115.31, 115.50, 116.47, 116.64, 120.87, 124.77, 131.29, 131.35, 133.33, 133.40, 134.67, 135.06, 149.37, 149.81, 161.06, 162.05, 163.00.

5-(3-Fluorophenyl)-4-(2-methyl-2H-tetrazol-5-yl) thiophene-2-carboxylic acid (DNM-123A) $^1$H NMR (500 MHz, DMSO) δ 4.35 (s, 3H), 7.28-7.37 (m, 2H), 7.41 (d, J=9.59 Hz, 1H), 7.49 (dd, J₁=7.89, J₂=14.18, 1H), 8.05 (s, 1H), 12.55 (broad, 1H); $^{13}$C NMR (125 MHz, DMSO) δ 39.63, 116.14, 116.22, 116.30, 116.40, 124.80, 125.63, 125.65, 130.62, 130.69, 133.82, 133.94, 134.00, 134.66, 146.94, 159.86, 160.80, 162.11, 162.75.

Ethyl 5-(3-fluorophenyl)-4-(1H-tetrazol-5-yl)thiophene-2-carboxylate (DNM-124A) $^1$H NMR (500 MHz, DMSO) δ 1.20 (t, J=6.38 Hz, 3H), 3.93 (q, J=6.38 Hz, 2H), 6.55-6.62 (m, 2H), 6.66 (dd, J₁=1.50, J₂=8.92, 1H), 6.75 (dd, J₁=7.16, J₂=12.74, 1H), 7.37 (s, 1H); $^{13}$C NMR (125 MHz, DMSO) δ 14.12, 61.65, 116.17, 116.35, 116.44, 116.60, 122.34, 125.53, 130.81, 130.88, 133.05, 133.39, 133.46, 134.57, 148.44, 160.60, 160.87, 162.82.

5-(2-Fluorophenyl)-4-(1H-tetrazol-5-yl)thiophene-2-carboxylic acid (DNM-121B) $^1$H NMR (500 MHz, DMSO) δ 7.26-7.34 (m, 2H), 7.49-7.57 (m, 2H), 8.16 (s, 1H); $^{13}$C NMR (125 MHz, DMSO) δ 115.88, 116.05, 119.97, 120.09, 124.66, 124.69, 125.29, 131.69, 131.76, 131.90, 133.21, 135.69, 141.13, 152.38, 158.10, 160.07, 162.19.

DNM-124C $^1$H NMR (500 MHz, CDCl₃) δ 1.47 (t, J=6.97 Hz, 3H), 4.48 (q, J=6.95 Hz, 2H), 7.75 (t, J=7.48 Hz, 1H), 7.87 (t, J=7.56 Hz, 1H), 8.15 (d, J=7.85 Hz, 1H), 8.65 (s, 1H), 8.73 (d, J=8.22 Hz, 1H); $^{13}$C NMR (125 MHz, CDCl₃) δ 14.31, 62.35, 118.05, 120.10, 122.32, 124.84, 128.67, 128.88, 129.10, 131.21, 136.60, 144.16, 144.96, 161.23.

5-(3-Methoxyphenyl)-4-(1H-tetrazol-5-yl)thiophene-2-carboxylic acid (DNM-121D) $^1$H NMR (500 MHz, DMSO) δ 3.74 (s, 3H), 6.98-7.07 (m, 3H), 7.36 (t, J=8.14 Hz, 1H), 8.07 (s, 1H), 13.60 (broad, 1H); $^{13}$C NMR (125 MHz, DMSO) δ 55.16, 114.47, 115.18, 121.25, 121.57, 129.96, 132.61, 134.16, 134.34, 149.74, 159.17, 162.10.

5-(3-Methoxyphenyl)-4-(1-methyl-1H-tetrazol-5-yl) thiophene-2-carboxylic acid (DNM-122D) $^1$H NMR (500 MHz, DMSO) δ 3.69 (s, 3H), 3.75 (s, 3H), 6.79 (s, 1H), 6.82 (d, J=7.64 Hz, 1H), 7.02 (dd, J₁=2.14, J₂=8:28, 1H), 7.33 (t, J=7.98 Hz, 1H), 8.00 (s, 1H), 13.60 (broad, 1H); $^{13}$C NMR (125 MHz, DMSO) δ 34.09, 55.17, 113.51, 115.43, 120.33, 120.45, 130.53, 132.46, 134.60, 134.75, 150.14, 150.71, 159.50, 162.12.

5-(3-Methoxyphenyl)-4-(2-methyl-2H-tetrazol-5-yl) thiophene-2-carboxylic acid (DNM-123D) $^1$H NMR (500 MHz, DMSO) δ 3.76 (s, 3H), 4.35 (s, 3H), 7.00-7.07 (m, 2H), 7.09 (s, 1H), 7.35 (t, J=7.92, 1H), 8.03 (s, 1H), 13.50 (broad, 1H); $^{13}$C NMR (125 MHz, DMSO) δ 39.60, 55.22, 114.63, 115.22, 121.52, 124.27, 129.76, 133.03, 134.02, 134.07, 148.71, 159.08, 160.06, 162.20.

5-(4-Methoxyphenyl)-4-(1H-tetrazol-5-yl)thiophene-2-carboxylic acid (DNM-121E) $^1$H NMR (500 MHz, DMSO) δ 3.81 (s, 3H), 7.00 (d, J=8.71 Hz, 2H), 7.40 (d, J=8.66 Hz, 2H), 8.05 (s, 1H), 13.50 (broad, 1H); $^{13}$C NMR (125 MHz, DMSO) δ 55.33, 114.25, 120.67, 123.72, 130.52, 133.36, 134.45, 150.36, 160.31, 162.19.

5-(4-Methoxyphenyl)-4-(1-methyl-1H-tetrazol-5-yl) thiophene-2-carboxylic acid (DNM-122E) $^1$H NMR (500 MHz, DMSO) δ 3.75 (s, 3H), 3.78 (s, 3H), 6.97 (d, J=8.75 Hz, 2H), 7.02 (d, J=8.73, 2H), 7.97 (s, 1H), 13.52 (broad, 1H); $^{13}$C NMR (125 MHz, DMSO) δ 34.09, 55.35, 114.77, 119.38, 123.52, 129.67, 133.54, 134.90, 150.25, 151.25, 160.38, 162.18.

5-(4-Methoxyphenyl)-4-(2-methyl-2H-tetrazol-5-yl) thiophene-2-carboxylic acid (DNM-123E) $^1$H NMR (500 MHz, DMSO) δ 3.81 (s, 3H), 4.35 (s, 3H), 6.99 (d, J=7.69 Hz, 2H), 7.45 (d, J=7.71 Hz, 2H), 8.01 (s, 1H), 13.42 (broad, 1H); $^{13}$C NMR (125 MHz, DMSO) δ 39.59, 55.28, 114.03, 123.56, 124.08, 130.68, 133.24, 134.16, 149.22, 160.12, 160.22, 162.27.

5-(2-Methoxyphenyl)-4-(1H-tetrazol-5-yl)thiophene-2-carboxylic acid (DNM-121F) $^1$H NMR (500 MHz, DMSO) δ 3.47 (s, 3H), 7.03 (t, J=7.45 Hz, 1H), 7.07 (d, J=8.31 Hz, 1H), 7.34 (d, J=7.47 Hz, 1H), 7.45 (t, J=7.85 Hz, 1H), 8.08 (s, 1H), 13.80 (broad, 1H); $^{13}$C NMR (125 MHz, DMSO) δ 55.65, 112.35, 120.82, 121.08, 123.79, 131.66, 131.71, 133.73, 134.77, 146.61, 156.65, 162.72.

5-(2-Methoxyphenyl)-4-(1-methyl-1H-tetrazol-5-yl) thiophene-2-carboxylic acid (DNM-122F) $^1$H NMR (500 MHz, DMSO) δ 3.44 (s, 3H), 3.84 (s, 3H), 6.99-7.06 (m, 2H), 7.31 (d, J=6.74, 1H), 7.43 (t, J=7.86 Hz, 1H), 8.05 (s, 1H), 13.53 (broad, 1H); $^{13}$C NMR (125 MHz, DMSO) δ 33.99, 55.31, 111.92, 119.88, 121.03, 122.15, 130.91, 131.50, 134.57, 147.29, 150.85, 155.42, 162.21.

5-(2-Methoxyphenyl)-4-(2-Methyl-2H-tetrazol-5-yl) thiophene-2-carboxylic acid (DNM-123F) $^1$H NMR (500 MHz, DMSO) δ 3.53 (s, 3H), 4.30 (s, 3H), 7.01 (t, J=7.38 Hz, 1H), 7.08 (d, J=8.27 Hz, 1H), 7.34 (d, J=7.43 Hz, 1H), 7.45 (t, J=7.84, 1H), 8.05 (s, 1H), 13.41 (broad, 1H); $^{13}$C NMR (125 MHz, DMSO) δ 39.43, 55.19, 111.76, 120.39, 120.82, 126.05, 131.05, 131.20, 132.83, 134.07, 144.91, 156.55, 160.57, 162.30.

5-(4-biphenyl)-4-(1H-tetrazol-5-yl)thiophene-2-carboxylic acid (DNM-121G) $^1$H NMR (500 MHz, DMSO) δ 7.40 (t, J=7.25 Hz, 1H), 7.49 (t, J=7.57 Hz, 2H), 7.58 (d, J=8.16 Hz, 2H), 7.69-7.78 (m, 4H), 8.08 (s, 1H); $^{13}$C NMR (125 MHz, DMSO) δ 122.92, 126.70, 126.86, 127.91, 129.04, 129.67, 130.92, 134.08, 134.66, 139.14, 140.90, 148.72, 152.16, 162.27.

5-(4-biphenylyl)-4-(1-methyl-1H-tetrazol-5-yl) thiophene-2-carboxylic acid (DNM-122G) $^1$H NMR (500 MHz, DMSO) δ 3.83 (s, 3H), 7.5-7.43 (m, 3H), 7.48 (t, J=7.61, 2H), 7.68-7.75 (m, 4H), 8.05 (s, 1H), 13.62 (broad, 1H); $^{13}$C NMR (125 MHz, DMSO) δ 34.22, 120.19, 126.70, 127.37, 128.06, 128.84, 129.03, 130.30, 134.50, 134.93, 138.78, 141.21, 150.14, 150.71, 162.13.

5-(4-biphenylyl)-4-(2-methyl-2H-tetrazol-5-yl) thiophene-2-carboxylic acid (DNM-123G) $^1$H NMR (500 MHz, DMSO) δ 4.36 (s, 3H), 7.41 (t, J=7.17 Hz, 1H), 7.50 (t, J=7.46, 2H), 7.60 (d, J=7.8.02 Hz, 2H), 7.70-7.78 (m, 4H), 8.03 (s, 1H); $^{13}$C NMR (125 MHz, DMSO) δ 39.62, 124.14, 126.70, 126.77, 127.90, 129.03, 129.82, 131.07, 133.77, 135.19, 139.17, 140.83, 148.17, 160.20, 162.33.

5-(Naphthalen-1-yl)-4-(1H-tetrazol-5-yl)thiophene-2-carboxylic acid (DNM-121H) $^1$H NMR (500 MHz, DMSO) δ 7.39 (t, J=7.21 Hz, 1H), 7.47-7.56 (m, 2H), 7.58-7.64 (m, 2H), 8.02 (d, J=8.17 Hz, 1H), 8.05-8.11 (m, 1H), 8.32 (s, 1H); $^{13}$C NMR (125 MHz, DMSO) δ 124.92, 125.14, 125.77, 126.72, 127.41, 128.90, 129.37, 129.68, 130.39, 131.74, 133.43, 133.59, 135.77, 147.90, 162.68.

5-(Naphthalen-1-yl)-4-(1-methyl-1H-tetrazol-5-yl) thiophene-2-carboxylic acid (DNM-122H) $^1$H NMR (500 MHz, DMSO) δ 3.80 (s, 3H), 7.45 (t, J=7.29, 1H), 7.49-7.65 (m, 4H), 7.99 (d, J=8.16, 1H), 8.05 (d, J=7.24, 1H), 8.21 (s, 1H), 13.67 (s, 1H); $^{13}$C NMR (125 MHz, DMSO) δ 34.26, 123.18, 124.16, 125.36, 126.48, 127.19, 128.40, 128.51, 129.18, 130.17, 130.59, 133.06, 133.89, 135.57, 148.96, 149.84, 162.17.

5-(Naphthalen-1-yl)-4-(2-methyl-2H-tetrazol-5-yl) thiophene-2-carboxylic acid (DNM-123H) $^1$H NMR (500 MHz, DMSO) δ 4.15 (s, 3H), 7.42 (t, J=6.73, 1H), 7.49-7.56 (m, 2H), 7.57-7.64 (m, 2H), 8.02 (d, J=8.13, 1H), 8.07 (d, J=7.55, 1H), 8.23 (s, 1H), 13.57 (s, 1H); $^{13}$C NMR (125 MHz, DMSO) δ 39.41, 124.75, 125.24, 126.20, 126.83, 126.87, 126.88, 127.58, 127.95, 128.38, 128.77, 129.53, 129.76, 131.39, 132.56, 133.04, 135.17, 146.20, 159.96, 162.24.

5-(Pyridin-2-yl)-4-(1H-tetrazol-5-yl)thiophene-2-carboxylic acid (DNM-121I) $^1$H NMR (500 MHz, DMSO) δ 7.48 (dd, $J_1$=4.92 Hz, $J_2$=7.08, 1H), 7.67 (d, J=7.97 Hz, 1H), 7.89 (t, J=7.78 Hz, 1H), 8.07 (s, 1H), 8.69 (d, J=4.34 Hz, 1H), 13.77 (broad, 1H); $^{13}$C NMR (125 MHz, DMSO) δ 122.28, 123.05, 124.79, 135.51, 135.95, 137.90, 150.07, 150.09, 150.27, 162.72.

5-(Pyridin-2-yl)-4-(1-methyl-1H-tetrazol-5-yl)thiophene-2-carboxylic acid (DNM-122I) $^1$H NMR (500 MHz, DMSO) δ 3.91 (s, 3H), 7.32 (d, J=7.98 Hz, 1H), 7.48 (dd, $J_1$=5.02 Hz, $J_2$=7.27, 1H), 7.86 (t, J=7.79 Hz, 1H), 8.01 (s, 1H); 8.58 (d, J=4.37 Hz, 1H), 13.67 (broad, 1H); $^{13}$C NMR (125 MHz, DMSO) δ 34.15, 120.83, 121.65, 124.31, 135.34, 135.50, 137.74, 149.30, 149.98, 150.24, 150.52, 162.21.

5-(Pyridin-2-yl)-4-(2-methyl-2H-tetrazol-5-yl)thiophene-2-carboxylic acid (DNM-123I) $^1$H NMR (500 MHz, DMSO) δ 4.46 (s, 3H), 7.46 (dd, $J_1$=4.86 Hz, $J_2$=7.35, 1H), 7.77 (d, J=8.00 Hz, 1H), 7.85 (t, J=7.77 Hz, 1H), 8.01 (s, 1H), 8.68 (d, J=4.48 Hz, 1H), 13.54 (broad, 1H); $^{13}$C NMR (125 MHz, DMSO) δ 122.79, 124.10, 124.41, 134.73, 135.44, 137.03, 149.08, 149.66, 149.96, 160.08, 162.35.

Ethyl 5-(pyridin-2-yl)-4-(1H-tetrazol-5-yl)thiophene-2-carboxylate (DNM-124I) $^1$H NMR (500 MHz, DMSO) δ 1.38 (t, J=6.73, 3H), 4.40 (q, J=6.73 Hz, 2H), 7.48 (dd, $J_1$=5.18 Hz, $J_2$=7.16, 1H), 7.72 (d, J=8.00 Hz, 1H), 7.90 (t, J=7.80 Hz, 1H), 8.15 (s, 1H), 8.69 (d, J=4.70 Hz, 1H).

Ethyl 5-(pyridin-2-yl)-4-(2-methyl-2H-tetrazol-5-yl) thiophene-2-carboxylate (DNM-125I) $^1$H NMR (500 MHz, CDCl$_3$) δ 1.39 (t, J=7.12, 3H), 4.30-4.45 (m, 5H), 7.24-7.29 (m, 1H), 7.69 (dd, $J_1$=1.54 Hz, $J_2$=7.76 Hz, 1H), 7.82 (d, J=7.96 Hz, 1H), 8.20 (s, 1H), 8.64 (d, J=4.64 Hz, 1H); $^{13}$C NMR (125 MHz, CDCl$_3$) δ 14.27, 39.55, 61.46, 123.29, 123.53, 124.45, 134.40, 135.54, 136.37, 149.60, 149.93, 150.95, 161.32, 161.73.

Ethyl 5-(pyridin-2-yl)-4-(1-methyl-1H-tetrazol-5-yl) thiophene-2-carboxylate (DNM-126I) $^1$H NMR (500 MHz, CDCl$_3$) δ 1.41 (t, J=7.13, 3H), 3.78 (s, 3H), 4.41 (q, J=7.13 Hz, 2H), 7.22-7.29 (m, 2H), 7.66 (dd, $J_1$=1.79 Hz, $J_2$=7.79 Hz, 1H), 7.85 (s, 1H), 8.51 (d, J=4.40 Hz, 1H); $^{13}$C NMR (125 MHz, CDCl$_3$) δ 14.28, 34.11, 61.90, 120.76, 121.55, 123.96, 135.09, 135.14, 137.35, 149.99, 150.20, 150.74, 151.10, 161.21.

(121J) $^1$H NMR (500 MHz, DMSO) δ 7.63 (d, J=4.88 Hz, 1H), 8.28 (s, 1H), 8.65) (d, J=4.89 Hz, 1H), 8.79 (s, 1H); $^{13}$C NMR (125 MHz, DMSO) δ 126.35, 130.61, 132.42, 132.46, 136.76, 138.85, 148.19, 148.25, 149.29, 149.35, 161.85.

(124J) $^{13}$C NMR (125 MHz, DMSO) δ 19.32, 67.06, 130.25, 131.56, 135.84, 138.05, 138.09, 140.23, 143.89, 147.29, 153.45, 153.50, 154.55, 154.60, 165.53.

EXAMPLE 3

Synthesis of 5-(4-fluorophenyl)-3-(1H-tetrazol-5-yl) thiophene-2-carboxylic acid analogues Method C (FIG. 14) was applied to the synthesis of 5-(4-fluorophenyl)-3-(1H-tetrazol-5-yl)thiophene-2-carboxylic acid analogues. The regioselective cross-coupling at C5 of 2,3,5-tribromothiophene with organozinc reagent afforded 5-aryl-2,3-dibromothiophene, in which Br at C2 was selectively transferred to carboxylate by transmetallation followed by the treatment with ethyl chloroformate. Br at C3 was converted to tetrazolyl group using the same method as method B.

2,3-Dibromo-5-(4-fluorophenyl)thiophene 2,3,5-Tribromothiophene (1.604 g, 5.0 mmol) and Pd(PPh$_3$)$_4$ (231 mg, 0.20 mmol) were dissolved in 20 mL of dry THF under argon. A solution of 4-fluorophenylzinc halide (15 mL of a 0.5 M solution in THF, 7.5 mmol) was added by syringe. The reaction was stirred at room temperature for 36 hours, quenched with a saturated aqueous ammonium chloride, and extracted with ethyl acetate. The organic layer was washed with brine and dried over anhydrous sodium sulfate. After removal of the solvent, the residue was purified by flash chromatography (hexane). 1.09 g (65%) of product was obtained as a white solid, mp: 90.0-92.0° C.; $^1$H NMR (CDCl$_3$, 500 MHz) δ 7.45 (m, 2H), 7.09 (m, 2H), 7.03 (s, 1H); $^{13}$C NMR (CDCl$_3$, 125 MHz) δ 163.87, 161.89, 144.27, 129.05, 129.02, 127.39, 127.32, 125.64, 116.31, 116.14, 114.64, 116.06.

Ethyl 3-bromo-5-(4-fluorophenyl)thiophene-2-carboxylate To a stirred solution of 2,3-dibromo-5-(4-fluorophenyl) thiophene (504 mg, 1.5 mmol) in 5 mL of dry THF was added n-BuLi (1.1 mL, 1.6 M in hexane, 1.8 mmol) at −78° C. After being stirred for half an hour at the same temperature, ethyl chloroformate (216 μL, 2.25 mmol) was added. The reaction was stirred for another hour at −78° C., quenched with saturated ammonium chloride, and extracted with ethyl acetate. The organic layer was dried over anhydrous sodium sulfate, and concentrated. The residue was purified by flash chromatography (hexane:ethyl acetate=25:1). 469 mg (95%) of product was obtained as a white solid, mp: 92.0-93.0° C.; $^1$H NMR (CDCl$_3$, 500 MHz) δ 7.56 (m, 2H), 7.20 (s, 1H), 7.11 (m, 2H), 4.38 (q, J=7.13 Hz, 2H), 1.40 (t, J=7.13 Hz, 3H); $^{13}$C NMR (CDCl$_3$, 125 MHz) δ 164.37, 162.39, 160.71, 148.08, 128.62, 128.59, 128.50, 127.93, 127.86, 126.22, 117.41, 116.41, 116.24, 61.49, 14.29.

Ethyl 3-cyano-5-(4-fluorophenyl)thiophene-2-carboxylate A suspension of ethyl. 3-bromo-5-(4-fluorophenyl) thiophene-2-carboxylate (400 mg, 1.22 mmol) and copper(I) cyanide (218 mg, 2.44 mmol) in 10 mL of dry DMF was refluxed for 5 hours. After cooling to room temperature, the reaction was diluted with ethyl acetate and filtered. The filtrate was washed with H$_2$O and brine, dried over anhydrous sodium sulfate, and concentrated. The residue was purified by flash chromatography (hexane:ethyl acetate=5:1). 295 mg (88%) of product was obtained as a white solid, mp: 141.0-143.0° C.; $^1$H NMR (CDCl$_3$, 500 MHz) δ 7.59 (m, 2H), 7.43 (s, 1H), 7.16 (m, 2H), 4.46 (q, J=7.14 Hz, 2H), 1.44 (t, J=7.14 Hz, 3H); $^{13}$C NMR (CDCl$_3$, 125 MHz) δ 164.67, 162.67, 159.64, 149.66, 138.72, 128.32, 128.26, 127.91, 127.77, 126.32, 116.72, 116.54, 114.88, 113.58, 62.54, 14.13.

5-(4-Fluoro-phenyl)-3-(1H-tetrazol-5-yl)-thiophene-2-carboxylic acid (DNM-141) Ethyl 3-cyano-5-(4-fluorophenyl)thiophene-2-carboxylate (220 mg, 0.8 mmol) was dissolved in 3 mL of methanol and 8 mL of THF. A solution of lithium hydroxide (120 mg, 5.0 mmol) in 3 mL of H$_2$O was added. After stirring at room temperature overnight, the solvent was removed. The residue was redissolved in H$_2$O, and acidified with 1N HCl. The white precipitate formed was collected by suction filtration, dried under vacuum, and dissolved in 5 mL of dry DMF under argon. Sodium azide (104 mg, 1.6 mmol) and Et$_3$N.HCl (220 mg, 1.6 mmol) was added. The reaction was stirred 24 hours at 70° C., quenched with 1N HCl after cooling to room temperature. The white precipitate formed was collected by suction filtration, washed with H$_2$O and chloroform, and dried under vacuum overnight. 165 mg (71%) of product was obtained as a white solid, mp: 281.0-283.0° C. (decomposed); $^1$H NMR (DMSO, 500 MHz) δ 7.91 (m, 2H), 7.35 (m, 2H); $^{13}$C NMR (DMSO, 125 MHz) δ 163.70, 161.81, 161.73, 150.05, 147.35, 131.85, 129.53, 128.47, 128.44, 128.41, 128.34, 126.63, 116.48, 116.31.

5-(4-Fluoro-phenyl)-3-(1-methyl-1H-tetrazol-5-yl)-thiophene-2-carboxylic acid methyl ester (DNM-145) and 5-(4-fluoro-phenyl)-3-(2-methyl-2H-tetrazol-5-yl)-thiophene-2-carboxylic acid methyl ester (DNM-144) To a stirred suspension of 5-(4-fluoro-phenyl)-3-(1H-tetrazol-5-yl)-thiophene-2-carboxylic acid (138 mg, 0.48 mmol) and potassium carbonate (328 mg, 2.38 mmol) in 5 mL of dry DMF was added methyl iodide (148 µl, 2.38 mmol). The reaction was stirred overnight at room temperature under argon, diluted with ethyl acetate, and filtered. The filtrate was washed with H$_2$O, dried over anhydrous sodium sulfate, and concentrated. Flash chromatography (chloroform:hexane:THF=50:25:3) purification afforded 78 mg (51.5%) of 5-(4-fluoro-phenyl)-3-(2-methyl-2H-tetrazol-5-yl)-thiophene-2-carboxylic acid methyl ester [white solid, mp: 131.5-132.5° C.; $^1$H NMR (DMSO, 500 MHz) δ 7.89 (m, 2H), 7.83 (s, 1H), 7.34 (m, 2H), 4.46 (s, 3H), 3.77 (s, 3H); $^{13}$C NMR (DMSO, 125 MHz) δ 163.62, 161.65, 160.66, 159.51, 147.23, 133.09, 129.37, 128.37, 128.35, 128.34, 128.29, 126.63, 116.38, 116.20, 52.36, 39.55] and 51 mg (33.7%) of 5-(4-fluoro-phenyl)-3-(1-methyl-1H-tetrazol-5-yl)-thiophene-2-carboxylic acid methyl ester [white solid, mp: 192.5-193.5° C.; $^1$H NMR (CDCl$_3$, 500 MHz) δ 7.63 (m, 2H), 7.37 (s, 1H), 7.16 (m, 2H), 3.99 (s, 3H), 3.84 (s, 3H); $^{13}$C NMR (CDCl$_3$, 125 MHz) δ 164.62, 162.62, 160.86, 150.48, 149.93, 131.02, 129.70, 128.38, 128.35, 128.30, 128.23, 126.32, 116.68, 116.50, 52.79, 34.41].

5-(4-Fluoro-phenyl)-3-(2-methyl-2H-tetrazol-5-yl)-thiophene-2-carboxylic acid (DNM-142) A solution of 5-(4-fluoro-phenyl)-3-(2-methyl-2H-tetrazol-5-yl)-thiophene-2-carboxylic acid methyl ester (45 mg, 0.14 mmol) and lithium hydroxide (17 mg, 0.71 mmol) in 3 mL of methanol, 4.5 mL of THF and 2 mL of H$_2$O was stirred overnight at room temperature. The solvent was removed, and the residue was redissolved in 5 mL of H$_2$O. After being acidified with 1N HCl, the precipitate formed was collected by suction filtration, washed with H$_2$O, and dried under vacuum overnight. 40 mg (93%) of product was obtained as a white solid, mp: slowly decomposed at 200° C.; $^1$H NMR (DMSO, 500 MHz) δ 13.36 (s, 1H), 7.86 (m, 2H), 7.75 (s, 1H), 7.32 (m, 2H), 4.45 (s, 3H); $^{13}$C NMR (DMSO, 125 MHz) δ 163.48, 161.63, 161.51, 159.75, 146.53, 132.30, 128.62, 128.60, 128.23, 128.16, 126.67, 116.33, 116.16, 39.59.

5-(4-Fluoro-phenyl)-3-(1-methyl-1H-tetrazol-5-yl)-thiophene-2-carboxylic acid (DNM-143) A solution of 5-(4-fluoro-phenyl)-3-(1-methyl-1H-tetrazol-5-yl)-thiophene-2-carboxylic acid methyl ester (28 mg, 0.088 mmol) and lithium hydroxide (10.5 mg, 0.44 mmol) in 3 mL of methanol, 4.5 mL of THF and 2 mL of H$_2$O was stirred overnight at room temperature. The solvent was removed, and the residue was redissolved in 5 mL of H$_2$O. After being acidified with 1N HCl, the precipitate formed was collected by suction filtration, washed with H$_2$O, and dried under vacuum overnight. 24 mg (90%) of product was obtained as a white solid, mp: 270.0-272.0° C. (decomposed); $^1$H NMR (DMSO, 500 MHz) δ 7.89 (m, 2H), 7.77 (s, 1H), 7.36 (m, 2H); $^{13}$C NMR (DMSO, 125 MHz) δ 163.76, 161.79, 161.46, 150.48, 147.83, 132.96, 128.94, 128.49, 128.45, 128.39, 127.03, 116.56, 116.39, 34.12.

EXAMPLE 4

Synthesis of 5-(2,5-Bis(4-fluorophenyl)thiophen-3-yl)-1H-tetrazole analogues

Method D (FIG. 15) was chosen to synthesize 5-(2,5-Bis(4-fluorophenyl)thiophen-3-yl)-1H-tetrazole analogues. The synthesis started with commercially available 2,3,5-tribromothiophene. To the best of our knowledge, the regioselectivity of cross-coupling between organometallic reagents and tribromo-substituted thiophene, furan, or pyrrole has not yet been reported. We found that the regioselectivity of cross-coupling between organometallic zinc and 2,3,5-tribromothiophene can be controlled by changing the reaction temperature. C5 is most active and least stereo-hindered, and can be selectively cross-coupled with organozinc reagents at room temperature. At refluxing temperature in THF, both C5 and C2 can be cross-coupled to afford di-aryl substituted thiophene. The bromo at C3 was converted into tetrazolyl group using the same method as method B.

3-Bromo-2,5-bis(4-fluorophenyl)thiophene 2,3,5-tribromothiophene (3.20 g, 10.0 mmol), Pd(PPh$_3$)$_2$Cl$_2$ (351 mg, 0.50 mmol) and triphenylphosphine (393 mg, 1.5 mmol) were dissolved in 30 mL of THF at room temperature. A solution of 4-fluorophenylzinc halide, prepared by transmetalation of 4-fluorophenylmagnesium bromide (20 mL of a 2 M solution in THF, 40.0 mmol) and zinc chloride (60 mL of 1 M solution in ether) in 80 mL of THF was added by cannula. The reaction was heated to 50° C. overnight, quenched with a saturated aqueous ammonium chloride after being cooled to room temperature and extracted with ethyl acetate. The organic layer was washed with brine and dried over anhydrous sodium sulfate. After removal of the solvent, the residue was purified by flash chromatography (hexane). 2.17 g (62%) of product was obtained as a white solid, mp: 100.0-102.0° C.; $^1$H NMR (CDCl$_3$, 500 MHz) δ 7.65 (m, 2H), 7.53 (m, 2H), 7.18 (s, 1H), 7.11 (m, 4H); $^{13}$C NMR (CDCl$_3$, 125 MHz) δ 163.75, 163.70, 161.77, 161.73, 142.16, 136.23, 130.77, 130.70, 129.36, 129.33, 128.79, 128.76, 127.34, 127.32, 127.28, 116.21, 116.04, 115.75, 115.58, 108.15.

2,5-Bis(4-fluorophenyl)thiophene-3-carbonitrile A suspension of 3-bromo-2,5-bis(4-fluorophenyl)thiophene (1.00 g, 2.85 mmol) and copper(I) cyanide in 15 mL of dry DMF was refluxed, and the progress of the reaction was monitored by TLC. After all starting material was consumed, the reaction was cooled to room temperature, quenched with 1N HCl, and extracted with ethyl acetate. The organic layer was washed with brine and dried over anhydrous sodium sulfate. After removal of the solvent, the residue was purified by flesh chromatography (hexane:dichloromethane=1:1). 0.793 g (94%) of product was obtained as a white solid, mp: 112.0-123.0° C.; $^1$H NMR (CDCl$_3$, 500 MHz) δ 7.76 (m, 2H), 7.55 (m, 2H), 7.35 (s, 1H), 7.18 (m, 2H), 7.13 (m, 2H); $^{13}$C NMR (CDCl$_3$, 125 MHz) δ 164.57, 164.07, 162.57, 162.08, 151.31, 143.06, 129.60, 129.54, 128.52, 128.50, 127.81, 127.74, 127.48, 127.45, 125.42, 116.58, 116.47, 116.41, 116.30, 115.56, 106.79.

5-(2,5-Bis(4-fluorophenyl)thiophen-3-yl)-1H-tetrazole (DNM-131) The reaction mixture of 2,5-bis(4-fluorophenyl)thiophene-3-carbonitrile (586 mg, 2.00 mmol), sodium azide (260 mg, 4.00 mmol) and zinc bromide (901 mg, 4.00 mmol) in 8 mL of dry DMF was refluxed overnight. After cooling to room temperature, the reaction mixture was quenched with 1N HCl and extracted with ethyl acetate. The organic layer was washed with brine, dried over anhydrous sodium sulfate. After removal of the solvent, the residue was purified by flash chromatography (hexane:ethyl acetate=100:7.5). 528 mg (91%) of product was obtained as a white solid, mp: 215.0 217.0° C. (decomposed); $^1$H NMR (DMSO, 500 MHz) δ 7.86 (s, 1H), 7.78 (m, 2H), 7.50 (m, 2H), 7.33 (m, 2H), 7.28 (m, 2H); $^{13}$C NMR (DMSO, 125 MHz) δ 163.32, 163.05, 161.36, 161.09, 151.43 (broad), 142.04, 131.16, 131.09, 128.98, 128.96, 128.32, 127.53, 127.46, 125.44, 121.82 (broad), 116.34, 116.16, 115.75, 115.58.

5-(2,5-Bis(4-fluorophenyl)thiophen-3-yl)-1-methyl-1H-tetrazole (DNM-133) and 5-(2,5-bis(4-fluorophenyl)thiophen-3-yl)-2-methyl-2H-tetrazole (DNM-132) To a stirred suspension of 5-(2,5-bis(4-fluorophenyl)thiophen-3-yl)-1H-tetrazole (200 mg, 0.59 mmol) and potassium carbonate (164 mg, 1.19 mmol) in 5 mL of dry DMF was added methyl iodide (93 µL, 1.49 mmol). The reaction was stirred for 4 hours at room temperature, diluted with ethyl acetate, and filtered. The filtrate was washed with H$_2$O and brine, dried over anhydrous sodium sulfate, and concentrated. The flash chromatography purification (dichloromethane as solvent) afforded 115 mg (55%) of 5-(2,5-bis(4-fluorophenyl)thiophen-3-yl)-2-methyl-2H-tetrazole [white solid, mp: 150.0-152.0° C. $^1$H NMR (DMSO, 500 MHz) δ 7.73 (s, 1H), 7.60 (m, 2H), 7.51 (m, 2H), 7.09 (m, 4H), 4.31 (s, 3H); $^{13}$C NMR (DMSO, 125 MHz) δ 163.94, 163.63, 161.96, 161.68, 161.66, 142.59, 142.02, 131.62, 131.55, 129.77, 129.74, 129.11, 129.09, 127.50, 127.43, 124.89, 124.69, 116.14, 115.97, 115.42, 115.24, 39.43] and 86 mg (41%) of 5-(2,5-bis(4-fluorophenyl)thiophen-3-yl)-1-methyl-1H-tetrazole [white solid, mp: 175.0-176.0° C.; $^1$H NMR (DMSO, 500 MHz) δ 7.60 (m, 2H), 7.39 (s; 1H), 7.22 (m, 2H), 7.12 (m, 2H), 7.07 (m, 2H), 3.52 (s, 3H); $^{13}$C NMR (DMSO, 125 MHz) δ 164.22, 164.09, 162.22, 162.11, 151.27, 144.12, 143.47, 130.03, 129.96, 129.25, 129.22, 128.58, 128.55, 127.84, 127.78, 125.59, 120.64, 116.94, 116.77, 117.55, 116.37, 34.14].

EXAMPLE 5

Synthesis of 5-(2,5-Bis(3-hydroxyphenyl)thiophen-3-yl)-1H-tetrazole analogues

Method E (FIG. 16) was chosen to synthesize 5-(2,5-Bis(hydroxyphenyl)thiophen-3-yl)-1H-tetrazole analogues. The commercially available thiophene-3-carbonitrile was converted to 5-(thiophen-3-yl)-1H-tetrazole by refluxing in DMF with sodium azide and ZnBr$_2$. The trityl-protected 5-(thiophen-3-yl)-1H-tetrazole was treated with t-BuLi and tributyltin chloride to give the di-stannyl compound. The Stille coupling of the di-stannous species and aryl halide gave 2,5-diaryl-4-(1-H-tetrazol-5-yl)thiophene. The trityl group was removed by simply refluxing in methanol.

5-(Thiophen-3-yl)-1H-tetrazole A mixture of thiophene-3-carbonitrile (5.72 g, 52.4 mmol), sodium azide (6.83 g, 105.1 mmol) and zinc bromide (23.65 g, 105.0 mmol) in 50 mL of dry DMF was heated to reflux and monitored by TLC until the reaction was complete (~5 h). After being cooled to room temperature, 150 mL of 1N aqueous HCl was added to precipitate the crude product. The white solid product was collected, washed with water and ether, and dried together with phosphorous pentaoxide under vacuum. 7.80 g (98%) of product was obtained as a white solid, mp: 203.0-205.0° C. [lit. mp: 244.8-255.3° C., Elpern, B.; Nachod, F. C. J. Am. Chem. Soc. 1950, 72, 3379-3382].

5-(Thiophen-3-yl)-2-trityl-2H-tetrazole 5-(Thiophen-3-yl)-1H-tetrazole (3.04 g, 20.0 mmol) was suspended in 40 mL of THF. Triethylamine (3.1 mL, 22 mmol) was added. After stirring for 10 minutes at room temperature, the reaction became a clear solution. Trityl chloride (6.13 g, 22.0 mmol) was added. The reaction was monitored with TLC until complete (~1 h). The solution was diluted with 100 mL of ethyl acetate and filtered. The filtrate was washed with H$_2$O and brine, dried over anhydrous sodium sulfate, and concentrated. The residue was suspended in 50 mL of ether, well stirred for 1 h, and filtered. The white solid was collected and dried under vacuum. 7.65 g (97%) of product was obtained.

5-(2,5-Bis(tributylstannyl)thiophen-3-yl)-2-trityl-2H-tetrazole A solution of 5-(thiophen-3-yl)-2-trityl-2H-tetrazole (3.94 g, 10.0 mmol) and TMEDA (4.9 mL, 32.7 mmol) in 40 mL of THF was cooled to −78° C. in a dry ice—acetone bath. t-BuLi (1.7 M, 19.0 mL, 32.3 mmol) was added dropwise to the solution. Upon complete addition, the dry ice—acetone bath was switched to dry ice—acetonitrile bath, and the reaction was held for 3 hours at this temperature. The solution was re-cooled to −78° C., and tributylstannyl chloride (8.8 mL, 32.4 mmol) was added. After stirring for 30 minutes at −78° C., the reaction was quenched with brine and extracted with ether. The organic layer was dried over anhydrous sodium sulfate and concentrated. The residue was purified by flash chromatography (4 inch-long column, a 3% of ether solution in hexane as solvent) to afford 8.45 g (87%) of product as a viscous liquid.

5-(2,5-Bis(3-hydroxyphenyl)thiophen-3-yl)-2-trityl-2H-tetrazole 5-(2,5-Bis(tributylstannyl)thiophen-3-yl)-2-trityl-2H-tetrazole (2.92 g, 3.0 mmol), ethyl 4-iodobenzonate (2.49 g, 9.0 mmol), Pd(PPh$_3$)$_4$ (173 mg, 0.15 mmol) and CuI (57 mg, 0.30 mmol) was dissolved in 10 mL of DMF. After degassing, the solution was heated to 50° C. and held at this temperature until the reaction was complete (~5 h). The solution was cooled to room temperature, quenched with brine, and extracted with ethyl acetate. The organic layer was dried over anhydrous sodium sulfate, and concentrated. The residue was purified with flash chromatography (hexane: EtOAc=5:1) to afford 1.35 g (65%) of product, obtained as a white solid, $^1$H NMR (CDCl$_3$, 500 MHz) δ; $^{13}$C NMR (CDCl$_3$, 125 MHz) δ.

5-(2,5-Bis(4-(ethoxylcarbonyl)phenyl)thiophen-3-yl)-1H-tetrazole (DNM-131J) A suspension of 5-(2,5-Bis(4-(ethoxylcarbonyl)phenyl)thiophen-3-yl)-2-trityl-2H-tetrazole (1.04 g, 1.5 mmol) in 20 mL of methanol was heated to reflux, and the progress of the reaction was monitored by TLC until the reaction was complete. After removing methanol, the residue solid was recrystallized to give 0.60 g (89%) of product as a white solid, $^1$H NMR (500 MHz, DMSO) δ 1.20-1.40 (m, 6H), 4.33 (q, J=7.05 Hz, 4H), 7.57 (d, J=8.26 Hz, 2H), 7.89 (d, J=8.29 Hz, 2H), 7.98 (d, J=8.28 Hz, 2H), 8.04 (d, J=8.31 Hz, 2H), 8.08 (s, 1H); $^{13}$C NMR (125 MHz, DMSO) δ 14.09, 14.10, 60.83, 60.87, 125.45, 127.32, 129.14, 129.42, 129.45, 129.96, 130.14, 136.30, 136.42, 142.63, 142.95, 165.12, 165.16.

5-(2,5-Bis(4-(ethoxylcarbonyl)phenyl)thiophen-3-yl)-2-methyl-2H-tetrazole (DNM-132J) and 5-(2,5-Bis(4-(ethoxylcarbonyl)phenyl)thiophen-3-yl)-1-methyl-1H-tetrazole (DNM-133J) To a stirred suspension of 5-(2,5-Bis(4-(ethoxylcarbonyl)phenyl)thiophen-3-yl)-1H-tetrazole (448 mg, 1.0 mmol) and potassium carbonate (166 mg, 1.2 mmol) in 5 mL of dry DMF was added methyl iodide (0.1 mL, 1.6 mmol). The reaction was stirred at room temperature and monitored by TLC. When the reaction was complete, the solution was diluted with ethyl acetate and filtered. The filtrate was washed with water, dried over anhydrous sodium sulfate, and concentrated. The residue was purified by flash chromatography (hexane:dichloromethane:ethyl acetate=10:10:1) to give 259 mg (60%) of 5-(2,5-Bis(4-(ethoxylcarbonyl)phenyl)thiophen-3-yl)-2-methyl-2H-tetrazole as a white solid [$^1$H NMR (500 MHz, DMSO) δ 1.33 (t, J=7.10 Hz, 6H), 4.25-4.40 (m, 7H), 7.62 (d, J=8.37 Hz, 2H), 7.89 (d, J=8.42 Hz, 2H), 7.96 (d, J=8.37 Hz, 2H), 7.99 (d, J=8.41 Hz, 2H), 8.06 (s, 1H); $^{13}$C NMR (125 MHz, DMSO) δ 14.58, 40.05, 61.27, 61.34, 125.93, 126.04, 127.51, 129.67, 129.75, 129.87, 130.25, 130.50, 137.04, 137.27, 142.37, 142.90, 160.70, 165.62, 165.69] and 128 mg (30%) of 5-(2,5-Bis(4-(ethoxylcarbonyl)phenyl)thiophen-3-yl)-1-methyl-1H-tetrazole as a white solid [$^1$H NMR (500 MHz, DMSO) δ 1.32 (t, J=7.08 Hz, 3H), 1.34 (t, J=7.13 Hz, 3H), 3.86 (s, 3H), 4.31 (q, J=7.13 Hz, 2H), 4.34 (q, J=7.06 Hz, 2H), 7.41 (d, J=8.38 Hz, 2H), 7.92 (d, J=8.48 Hz, 2H), 7.95 (d, J=8.43 Hz, 2H), 8.04 (d, J=8.42 Hz, 2H), 8.07 (s, 1H); $^{13}$C NMR (125 MHz, DMSO) δ 14.05, 14.10, 34.27, 60.84, 60.91, 121.63, 125.59, 127.77, 128.31, 129.52, 129.83, 130.04, 130.08, 135.97, 136.41, 143.00, 144.13, 150.25, 165.00, 165.11].

The following compounds were prepared using the same method above:

5-(2,5-Bis(3-hydroxyphenyl)thiophen-3-yl)-1H-tetrazole (DNM-131A) $^1$H NMR (500 MHz, DMSO) δ 6.73-6.84 (m, 4H), 7.09 (s, 1H), 7.16 (d, J=7.63 Hz, 1H), 7.21 (t, J=7.85 Hz, 1H), 7.28 (t, J=7.87 Hz, 1H), 7.73 (s, 1H), 9.63 (s, 1H), 9.71 (s, 1H); $^{13}$C NMR (125 MHz, DMSO) δ 112.04, 115.34, 115.62, 115.89, 116.23, 119.31, 125.41, 129.93, 130.45, 133.04, 133.62, 143.09, 143.30, 157.50, 158.00.

5-(2,5-Bis(3-hydroxyphenyl)thiophen-3-yl)-2-methyl-2H-tetrazole (DNM-132A) $^1$H NMR (500 MHz, DMSO) δ 4.41 (s, 3H), 6.80-6.85 (m, 2H), 6.84 (s, 1H), 6.88 (d, J=7.73 Hz, 1H), 6.92 (s, 1H), 7.19-7.26 (m, 2H), 7.30 (t, J=7.88 Hz, 1H), 7.76 (s, 1H), 9.61 (s, 1H), 9.70 (s, 1H); $^{13}$C NMR (125 MHz, DMSO) δ 34.03, 112.15, 114.37, 115.67, 116.09, 116.33, 118.45, 120.07, 125.74, 130.41, 130.43, 132.96, 133.58, 143.46, 144.05, 150.80, 157.84, 157.99.

5-(2,5-Bis(3-hydroxyphenyl)thiophen-3-yl)-1-methyl-1H-tetrazole (DNM-133A) $^1$H NMR (500 MHz, DMSO) δ 3.76 (s, 3H), 6.65 (s, 1H), 6.68 (d, J=7.96 Hz, 1H), 6.80-6.86 (m, 2H), 7.14 (s, 1H), 7.20-7.26 (m, 2H), 7.31 (t, J=7.87 Hz, 1H), 7.74 (s, 1H), 9.74 (s, 2H); $^{13}$C NMR (125 MHz, DMSO) δ 34.03, 112.15, 114.36, 115.67, 116.09, 116.33, 118.45, 120.07, 125.74, 130.41, 130.43, 132.96, 133.58, 143.46, 144.05, 150.80, 157.84, 157.99.

5-(2,5-Bis(3-methoxyphenyl)thiophen-3-yl)-1H-tetrazole (DNM-131B) $^1$H NMR (500 MHz, DMSO) δ 3.57 (s, 3H), 3.80 (s, ±3H), 6.88-6.98 (m, 4H), 7.20-7.40 (m, 4H); $^{13}$C NMR (125 MHz, DMSO) δ 54.92, 55.25, 110.60, 114.19, 114.22, 114.45, 117.84, 121.28, 124.44, 125.35, 129.62, 130.36, 113.52, 133.85, 142.56, 142.83, 159.02, 159.80, 159.82.

5-(2,5-Bis(3-methoxyphenyl)thiophen-3-yl)-2-methyl-2H-tetrazole (DNM-132B) $^1$H NMR (500 MHz, DMSO) δ 3.80 (s, 3H), 3.88. (s, 3H), 4.41 (s, 3H), 6.97-7.04 (m, 2H), 7.07-7.13 (m, 2H), 7.31-7.39 (m, 3H), 7.42 (t, J=7.86 Hz, 1H), 7.94 (s, 1H); $^{13}$C NMR (125 MHz, DMSO) δ 39.55, 55.16, 55.28, 110.54, 114.28, 114.46, 114.51, 117.85, 121.40, 124.46, 125.66, 129.63, 130.40, 133.68, 133.92, 142.13, 142.74, 159.07, 159.87, 160.66.

5-(2,5-Bis(3-methoxyphenyl)thiophen-3-yl)-1-methyl-1H-tetrazole (DNM-133B) $^1$H NMR (500 MHz, DMSO) δ 3.74 (s, 3H), 3.80 (s, 3H), 3.88 (s, 1H), 6.81 (s, 1H), 6.83 (d, J=7.66 Hz, 1H), 7.20 (d, J=8.27 Hz, 2H), 7.33-7.39 (m, 3H), 7.44 (t, J=7.89 Hz, 1H), 7.91 (s, 1H); $^{13}$C NMR (125 MHz, DMSO) δ 34.11, 55.13, 55.31, 110.79, 113.20, 114.37, 114.71, 117.92, 120.15, 120.39, 126.22, 130.48, 130.49, 133.02, 133.70, 143.40, 144.00, 150.77, 159.53, 159.88.

5-(2,5-Bis(4-hydroxyphenyl)thiophen-3-yl)-1H-tetrazole (DNM-131C) $^1$H NMR (500 MHz, DMSO) δ 6.82 (d, J=8.54 Hz, 2H), 6.89 (d, J=8.54 Hz, 2H), 7.25 (d, J=8.51 Hz, 2H), 7.56 (d, J=8.53 Hz, 2H), 7.62 (s, 1H), 9.81 (s, 2H); $^{13}$C NMR (125 MHz, DMSO) δ 115.53, 116.01, 122.78, 123.49, 123.71, 126.73, 130.04, 142.57, 142.62, 157.78, 158.01.

5-(2,5-Bis(4-hydroxyphenyl)thiophen-3-yl)-2-methyl-2H-tetrazole (DNM-132C) $^1$H NMR (500 MHz, DMSO) δ 4.39 (s, 3H), 6.82 (d, J=8.44 Hz, 2H), 6.87 (d, J=8.46 Hz, 2H), 7.33 (d, J=8.44 Hz, 2H), 7.57 (d, J=8.45 Hz, 2H), 7.64 (s, 1H), 9.75 (s, 1H), 9.76 (s, 1H); $^{13}$C NMR (125 MHz, DMSO) δ 39.48, 115.23; 115.96, 123.21, 123.27, 123.32, 123.93, 126.73, 130.42, 141.47, 142.37, 157.65, 157.78, 161.01.

5-(2,5-Bis(4-hydroxyphenyl)thiophen-3-yl)-1-methyl-1H-tetrazole (DNM-133C) $^1$H NMR (500 MHz, DMSO) δ 3.74 (s, 3H), 6.80 (d, J=8.55. Hz, 2H), 6.89 (d, J=8.56 Hz, 2H), 7.07 (d, J=8.56 Hz, 2H), 7.57 (s, 1H), 7.58 (d, J=8.55 Hz, 2H), 9.80 (s, 1H), 9.87 (s, 1H); $^{13}$C NMR (125 MHz, DMSO) δ 34.50, 116.48, 116.51, 119.39, 123.21, 124.19, 124.30, 127.39, 129.68, 143.45, 143.73, 151.56, 158.32, 158.61.

5-(2,5-Bis(4-methoxyphenyl)thiophen-3-yl)-1H-tetrazole (DNM-131D) $^1$H NMR (500 MHz, DMSO) δ 3.80 (s, 3H), 3.82 (s, 3H), 6.99 (d, J=8.74 Hz, 2H), 7.05 (d, J=8.74 Hz, 2H), 7.36 (d, J=8.69 Hz, 2H), 7.66 (d, J=8.70 Hz, 2H), 7.70 (s, 1H); $^{13}$C NMR (125 MHz, DMSO) δ 55.26, 55.29, 114.20, 114.73, 124.17, 124.35, 125.20, 126.70, 130.09, 142.47, 159.44, 159.66.

5-(2,5-Bis(4-methoxyphenyl)thiophen-3-yl)-2-methyl-2H-tetrazole (DNM-132D) $^1$H NMR (500 MHz, DMSO) δ 3.84 (2s, 6H), 4.39 (s, 3H), 7.01 (d, J=8.71 Hz, 2H), 7.06 (d, J=8.72 Hz, 2H), 7.45 (d, J=8.67 Hz; 2H), 7.70 (d, J=8.67 Hz, 2H), 7.75 (s, 1H); $^{13}$C NMR (125 MHz, DMSO) δ 39.50, 55.21, 55.26, 113.89, 114.65, 123.68, 123.92, 124.86, 125.39, 126.71, 130.44, 141.32, 142.22, 159.32, 159.46, 160.87.

5-(2,5-Bis(4-methoxyphenyl)thiophen-3-yl)-1-methyl-1H-tetrazole (DNM-133D) $^1$H NMR (500 MHz, DMSO) δ 3.79 (s, 3H), 3.81 (s, 3H), 3.85 (s, 3H), 7.00 (d, J=8.76 Hz, 2H), 7.08 (d, J=8.77 Hz, 2H), 7.21 (d, J=8.73 Hz, 2H), 7.69 (s, 1H), 7.72 (d, J=8.73 Hz, 2H); $^{13}$C NMR (125 MHz, DMSO) δ 34.08, 55.28, 55.30, 114.68, 114.69, 119.41, 124.23, 124.50, 125.18, 126.82, 129.23, 142.78, 143.21, 150.92, 159.48, 159.71.

5-(2,5-Bis(4-carboxyphenyl)thiophen-3-yl)-1H-tetrazole (DNM-131E) $^1$H NMR (500 MHz, DMSO) δ 7.60 (d, J=8.06 Hz, 2H), 7.93 (d, J=8.10 Hz, 2H), 8.02 (d, J=8.08 Hz, 2H), 8.08 (d, J=8.11 Hz, 2H), 8.12 (p, 1H), 13.10 (broad, 2H); $^{13}$C NMR (125 MHz, DMSO) δ 125.42, 127.25, 129.05, 129.68, 130.38, 130.46, 130.94, 136.03, 136.19, 142.76, 143.10, 166.73, 166.77.

5-(2,5-Bis(4-carboxyphenyl)thiophen-3-yl)-2-methyl-2H-tetrazole (DNM-132E) $^1$H NMR (500 MHz, DMSO) δ 4.41 (s, 3H), 7.66 (d, J=8.39 Hz, 2H), 7.94 (d, J=8.37 Hz, 2H), 8.01 (d, J=8.39 Hz, 2H), 8.05 (d, J=8.42 Hz, 2H), 8.11 (s, 1H), 13.10 (s, 2H); $^{13}$C NMR (125 MHz, DMSO) δ 39.63, 125.46, 125.56, 126.94, 129.33, 129.47, 130.30, 130.32, 130.78, 136.36, 136.54, 142.06, 142.58, 160.32, 166.77, 166.84.

5-(2,5-Bis(4-carboxyphenyl)thiophen-3-yl)-1-methyl-1H-tetrazole (DNM-133E) $^1$H NMR (500 MHz, DMSO) δ 3.91 (s, 3H), 7.44 (d, J=8.35 Hz, 2H), 7.95 (d, J=8.39 Hz, 2H), 7.98 (d, J=8.35 Hz, 2H), 8.08 (d, J=8.42 Hz, 2H), 8.09 (s, 1H), 13.14 (s, 2H); $^{13}$C NMR (125 MHz, DMSO) δ 34.34, 121.52, 125.57, 127.61, 128.29, 130.08, 130.34, 130.55, 131.05, 135.74, 136.18, 143.15, 144.28, 150.36, 166.64, 166.75.

5-(2,5-Bis(4-carbamoylphenyl)thiophen-3-yl)-1H-tetrazole (DNM-131F) $^1$H NMR (500 MHz, DMSO) δ 7.40-7.48 (broad, 2H), 7.51 (d, J=8.30 Hz, 2H), 7.85 (d, J=8.35 Hz, 2H), 7.91 (d, J=8.32 Hz, 2H), 7.99 (d, J=8.36 Hz, 2H), 8.03 (s, 1H), 8.05 (broad, 2H); $^{13}$C NMR (125 MHz, DMSO) δ 122.60, 125.12, 126.79, 127.91, 128.59, 128.65, 133.96, 134.42, 134.56, 134.82, 142.77, 143.02, 167.14, 167.20.

5-(2,5-Bis(3-carboxyphenyl)thiophen-3-yl)-1H-tetrazole (DNM-131G) $^1$H NMR (500 MHz, DMSO) δ 7.62 (t, J=7.95 Hz, 1H), 7.67 (t, J=7.77 Hz, 1H), 7.76 (d, J=7.79 Hz, 1H), 8.00 (d, J=7.79 Hz, 1H), 8.02-8.07 (m, 3H), 8.08 (s, 1H), 8.32 (s, 1H), 13.22 (broad, 2H); $^{13}$C NMR (125 MHz, DMSO) δ 125.84, 126.24, 129.20, 129.22, 129.62, 129.65, 129.88, 131.29, 131.93, 132.26, 132.68, 133.29, 142.56, 166.73, 166.81.

5-(2,5-Bis(3-carboxyphenyl)thiophen-3-yl)-2-methyl-2H-tetrazole (DNM-132G) $^1$H NMR (500 MHz, DMSO) δ 4.37 (s, 3H), 7.57 (t, J=7.72 Hz, 1H), 7.62 (t, J=7.74 Hz, 1H), 7.78 (d, J=8.62 Hz, 1H), 7.95 (d, J=7.67 Hz, 1H), 8.00 (d, J=7.75 Hz, 1H), 8.02 (s, 1H), 8.04-8.10 (m, 2H), 8.24 (s, 1H), 13.17 (broad, 2H); $^{13}$C NMR (125 MHz, DMSO) δ 39.59, 125.11, 125.85, 125.94, 128.94, 129.07, 129.46, 129.65, 129.77, 129.84, 131.10, 131.85, 132.66, 132.81, 133.56, 141.46, 142.34, 160.41, 166.77, 166.81.

5-(2,5-Bis(3-carboxyphenyl)thiophen-3-yl)-1-methyl-1H-tetrazole (DNM-133G) $^1$H NMR (500 MHz, DMSO) δ 3.89 (s, 3H), 7.50-7.59 (m, 2H), 7.64 (t, J=7.71 Hz, 1H), 7.85 (s, 1H), 7.94-8.00 (m, 2H), 8.02 (s, 1H), 8.06 (d, J=7.57 Hz, 1H), 8.29 (s, 1H), 13.21 (s, 2H); $^{13}$C NMR (125 MHz, DMSO) δ 34.76, 121.50, 126.44, 127.16, 129.10, 129.72, 130.06, 130.15, 130.20, 130.24, 132.12, 132.38, 132.47, 132.80, 133.13, 143.29, 144.18, 150.84, 166.96, 167.25.

5-(2,5-Bis(3-carbamoylphenyl)thiophen-3-yl)-1H-tetrazole (DNM-131H) $^1$H NMR (500 MHz, DMSO) δ 7.44 (s, 1H), 7.48-7.54 (m, 2H), 7.54-7.61 (m, 2H), 7.87-7.95 (m, 3H), 7.99 (s, 1H), 8.02 (s, 1H), 8.05 (s, 1H), 8.15 (s, 1H), 8.25 (s, 1H); $^{13}$C NMR (125 MHz, DMSO) δ 122.59, 124.31, 126.14, 127.45, 127.79, 127.94, 128.06, 128.71, 129.44, 131.57, 132.12, 132.48, 134.73, 135.24, 142.64, 142.77, 151.90, 167.18, 167.22.

5-(2,5-Bis(3-(ethoxylcarbonyl)phenyl)thiophen-3-yl)-1H-tetrazole (DNM-131I) $^1$H NMR (500 MHz, DMSO) δ 1.31 (t, J=7.08 Hz, 3H), 1.36 (t, J=7.07 Hz, 3H), 4.33 (q, J=7.07 Hz, 2H), 4.37 (q, J=7.06 Hz, 2H), 7.60 (t, J=7.69 Hz, 1H), 7.65 (t, J=7.72 Hz, 1H), 7.75 (d, J=7.63 Hz, 1H), 7.94-8.07 (m, 5H), 8.26 (s, 1H); $^{13}$C NMR (125 MHz, DMSO) δ 14.08, 14.15, 61.00, 61.10, 125.53, 126.35, 129.01, 129.34, 129.42, 129.98, 130.01, 130.35, 131.02, 132.36, 132.79, 142.39, 165.13, 165.24.

5-(2,5-Bis(3-(methoxylcarbonyl)phenyl)thiophen-3-yl)-2-methyl-2H-tetrazole (DNM-132I) $^1$H NMR (500 MHz, DMSO) δ 3.90 (s, 3H), 3.93 (s, 3H), 4.35 (s, 3H), 7.53 (t, J=7.76 Hz, 1H), 7.58 (t, J=7.76 Hz, 1H), 7.77 (d, J=7.64 Hz, 1H), 7.91-7.99 (m, 3H), 8.02 (d, J=7.79 Hz, 1H), 8.15 (s, 1H), 8.26 (s, 1H); $^{13}$C NMR (125 MHz, DMSO) δ 39.16, 51.81, 51.86, 124.90, 125.38, 125.67, 128.28, 128.54, 128.98, 129.20, 129.47, 129.73, 129.84, 130.52, 132.70, 132.87, 133.64, 141.23, 142.07, 160.37, 165.50, 165.52.

5-(2,5-Bis(3-(ethoxylcarbonyl)phenyl)thiophen-3-yl)-1-methyl-1H-tetrazole (DNM-133I) $^1$H NMR (500 MHz, DMSO) δ 1.31 (t, J=7.10 Hz, 3H), 1.35 (t, J=7.10 Hz, 3H), 3.88 (s, 3H), 4.30 (q, J=7.10 Hz, 2H), 4.36 (q, J=7.10 Hz, 2H), 7:53-7.59 (m, 2H), 7.65 (t, J=7.79 Hz, 1H), 7.83 (s, 1H), 7.94-7.99 (m, 2H), 8.02 (s, 1H), 8.07 (d, J=7.35 Hz, 1H), 8.27 (s, 1H); $^3$C NMR (125 MHz, DMSO) δ 14.03, 14.13, 61.04, 61.08, 121.19, 125.71, 126.89, 128.34, 129.07, 129.46, 129.77, 129.92, 130.10, 130.72, 131.02, 132.08, 132.66, 132.78, 142.67, 143.53, 150.36, 164.91, 165.23.

5-(2,5-Bis(2-(methoxylcarbonyl)phenyl)thiophen-3-yl)-1H-tetrazole (DNM-131K) $^1$H NMR (500 MHz, CDCl$_3$) δ 3.75 (s, 3H), 3.81 (s, 3H), 7.40-4.49 (m, 2H), 7.49-7.50 (s, 1H), 7.52-7.59 (m, 4H), 7.83 (d, J=7.57 Hz, 1H), 7.91-7.95 (m, 1H); $^{13}$C NMR (125 MHz, CDCl$_3$) δ 52.56, 52.93, 122.53, 126.64, 128.78; 129.97, 130.19, 130.35, 131.48, 131.52, 131.68, 131.99, 132.21, 132.34, 132.65, 133.00, 142.94, 143.28, 151.45, 168.41, 168.59.

5-(2,5-Bis(2-(methoxylcarbonyl)phenyl)thiophen-3-yl)-1-methyl-1H-tetrazole (DNM-133K) $^1$H NMR (500 MHz, CDCl$_3$) δ 3.68 (s, 3H), 3.77 (s, 3H), 3.84 (s, 3H), 7.23 (s, 1H), 7.33 (d, J=7.42 Hz, 1H), 7.43-7.53 (m, 3H), 7.57 (d, J=4.06 Hz, 2H), 7.85 (d, J=7.26 Hz, 2H); $^3$C NMR (125 MHz, CDCl$_3$) δ 34.08, 52.37, 52.41, 121.09, 127.41, 128.66, 129.24, 130.05, 130.52, 131.35, 131.40, 131.42, 131.47, 131.99, 132.02, 132.04, 132.81, 143.57, 144.54, 150.85, 167.24, 168.23.

5-(2,5-Bis(2-carboxyphenyl)thiophen-3-yl)-1H-tetrazole (DNM-131L) $^1$H NMR (500 MHz, DMSO) δ 7.41 (d, J=6.96 Hz, 1H), 7.47-7.66 (m, 6H), 7.71 (d, J=7.58 Hz, 1H), 7.87 (d, J=7.23 Hz, 1H); $^{13}$C NMR (125 MHz, DMSO) δ 123.43, 126.24, 128.46, 128.97, 129.03, 129.75, 130.35, 130.94, 131.10, 131.98, 132.14, 132.89, 133.48, 141.21, 142.74, 152.74, 167.86, 169.61.

5-(2,5-Bis(2-carboxyphenyl)thiophen-3-yl)-2-methyl-2H-tetrazole (DNM-132L) $^1$H NMR (500 MHz, DMSO) δ 4.26 (s, 3H), 7.45-7.53 (m, 2H), 7.53-7.65 (m, 5H), 7.68 (d, J=7.61 Hz, 1H), 7.91 (d, J=7.51 Hz, 1H), 12.91 (broad, 2H); $^{13}$C NMR (125 MHz, DMSO) δ 39.34, 124.88, 125.98, 128.26, 128.73, 128.88, 129.95, 130.08, 130.78, 130.79, 131.23, 132.11, 132.57, 132.69, 132.80, 140.77, 142.27, 160.71, 167.54, 169.77.

5-(2,5-Bis(2-carboxyphenyl)thiophen-3-yl)-1-methyl-1H-tetrazole (DNM-133L) $^1$H NMR (500 MHz, DMSO) δ 3.91 (s, 3H), 7.43 (d, J=7.44 Hz, 1H), 7.49-7.55 (m, 3H), 7.58-7.66 (m, 3H), 7.75 (t, J=6.54 Hz, 2H), 12.93 (broad, 2H).

3-(5-(pyridin-3-yl)-4-(1H-tetrazol-5-yl)thiophen-2-yl)pyridine (DNM-131M) $^{13}$C NMR (125 MHz, DMSO) δ 123.93, 124.73, 126.28, 127.61, 129.16, 129.24, 133.30, 137.11, 139.10, 140.46, 146.66, 149.66, 149.76, 149.85, 153.79.

4-(5-(pyridin-4-yl)-4-(1H-tetrazol-5-yl)thiophen-2-yl)pyridine (DNM-131N) $^1$H NMR (500 MHz, DMSO) δ 7.46 (d, J=5.98 Hz, 2H), 7.76 (d, J=6.00 Hz, 2H), 8.24 (s, 1H), 8.64 (d, J=5.71 Hz, 2H), 8.68 (d, J=5.60 Hz, 2H); $^{13}$C NMR (125 MHz, DMSO) δ 119.55, 123.14, 124.22, 128.62, 139.13, 139.30, 141.54, 141.59, 150.00, 150.52, 151.94.

5-(2,5-Dibenzylthiophen-3-yl)-1H-tetrazole (DNM-131O) $^1$H NMR (500 MHz, CDCl$_3$) δ 4.02 (s, 2H), 4.50 (s, 2H), 7.10-7.30 (m, 11H); $^{13}$C NMR (125 MHz, CDCl$_3$) δ

35.22, 36.17, 120.01, 124.98, 126.93, 127.13, 128.78, 128.82, 128.83, 128.96, 139.34, 139.36, 143.92, 146.37.

EXAMPLE 6

Synthesis of 5-(2-benzyl-5-(4-fluorophenyl) thiophen-3-yl)-1H-tetrazole

Method F (FIG. 17) was used to synthesize 5-(2-benzyl-5-(4-fluorophenyl)thiophen-3-yl)-1H-tetrazole (DNM-151A). Method F is used to prepare asymmetrically 2,5-di-aryl-substituted molecules. Trityl-protected tetrazole can be used as an ortho lithiation direction group (Rhonnstad, P.; Wensbo, D. Tetrahedron Lett. 2002, 43, 3137). When 1-Trityl-5-(thiophen-3-yl)-1H-tetrazole was treated with 1 equivalent of BuLi, lithiation was selectively directed to C2 position of the thiophene ring to form C2 lithium species, which gave C2 stannyl substituted thiophene while treated with tributylstannyl chloride. The resulting stannyl thiophene was cross-coupled with aryl halide to introduce the first aromatic substitutent. While C2 position of the thiophene in 1-trityl-5-(thiophen-3-yl)-1H-tetrazole was substituted, C5 could be further lithiated, and then iodinated when the lithium species was treated with iodine. The cross-coupling of the resulting iodide with arylzinc, stannyl reagents, or boron reagents furnished the second aromatic substitutent. Method G, a modified procedure of method F in term of the introduction of first aryl substitutent, was also applied for the preparation of asymmetrically 2,5-di-aryl-substituted molecules.

5-(2-(Tributylstannyl)thiophen-3-yl)-2-trityl-2H-tetrazole A solution of 5-(thiophen-3-yl)-2-trityl-2H-tetrazole (3.94 g, 10.0 mmol) in 40 mL of THF was cooled to −78° C. BuLi (2.5 M, 5.0 mL, 12.5 mmol) was added dropwise. Upon complete addition, the reaction was stirred for 2 hours at −78° C. Tributylstannyl chloride (3.4 mL, 12.5 mmol) was added. The reaction was hold at −78° C. until complete, quenched with brine, and extracted with ether. The organic layer was dried over anhydrous Sodium sulfate, and concentrated. The residue was purified with flash chromatography (hexane:ether=20:1) to afford 6.24 g (91%) of product as a viscous liquid, $^1$H NMR (500 MHz, CDCl$_3$) δ 0.81 (t, J=7.31 Hz, 9H), 1.03 (t, J=8.19 Hz, 6H), 1.18-1.28 (m, 6H), 1.33-1.51 (m, 6H), 7.12-7.19 (m, 6H), 7.29-7.38 (m, 9H), 7.64 (d, J=4.81 Hz, 1H), 7.84 (d, J=4.78 Hz, 1H); $^{13}$C NMR (125 MHz, CDCl$_3$) δ 11.69, 13.81, 27.30, 29.04, 82.97, 127.93, 128.38, 129.09, 130.41, 131.49, 135.67, 140.42, 141.66, 162.65.

5-(2-Benzylthiophen-3-yl)-2-trityl-2H-tetrazole 5-(2-(tributylstannyl)thiophen-3-yl)-2-trityl-2H-tetrazole (5.55 g, 8.1 mmol), benzyl bromide (1.5 mL, 12.6 mmol), Pd(PPh$_3$)$_4$ (282 mg, 0.24 mmol) and CuI (93 mg, 0.49 mmol) was dissolved in 50 mL of THF. After degassing, the solution was heated to reflux and the progress of the reaction was monitored with TLC (~5 h). When the reaction was complete, the solution was cooled to room temperature, quenched with brine, and extracted with ethyl acetate. The organic layer was dried over anhydrous sodium sulfate and concentrated. The residue was purified with flash chromatography (dichloromethane:hexane=3:2) to afford 2.36 g (60%) of product, obtained as a white solid, $^1$H NMR (CDCl$_3$, 500 MHz) δ 4.46 (s, 2H), 7.05-7.10 (m, 2H), 7.10-7.14 (m, 6H), 7.14-7.20 (m, 4H), 7.27-7.37 (m, 9H), 7.65 (d, J=5.33 Hz, 1H); $^{13}$C NMR (CDCl$_3$, 125 MHz) δ 34.98, 83.23, 123.74, 124.71, 126.47, 127.89, 128.12, 128.44, 128.50, 128.85, 130.45, 140.04, 141.54, 145.15, 160.86.

5-(2-Benzyl-5-iodothiophen-3-yl)-2-trityl-2H-tetrazole A solution of 5-(2-benzylthiophen-3-yl)-2-trityl-2H-tetrazole (1.88 g, 3.88 mmol) and TMEDA (0.73 mL, 4.87 mmol) in 40 mL of THF was cooled to −78° C. t-BuLi (1.7 M, 2.9 mL, 4.9 mmol) was dropwise added to the solution. When the addition was complete, the reaction was stirred for 2 hours at −78° C. Iodine (1.27 g, 5.0 mmol) was added. After 30 minutes, the reaction was worked up with a solution of sodium carbonate and sodium sulfite, extracted with ethyl acetate. The organic layer was dried over anhydrous sodium sulfate and concentrated. The residue was purified by flash chromatography (dichloromethane:hexane=5:4) to give 2.0 g (85%) product as a white solid, $^1$H NMR (acetone, 500 MHz) δ 7.10-7.30 (m, 11H), 7.35-7.45 (m, 9H), 7.78 (s, 1H); $^{13}$C NMR (acetone, 125 MHz) δ 34.45, 71.69, 83.17, 126.48, 126.57, 127.85, 128.39, 128.49, 128.60, 130.13, 136.70, 139.45, 141.49, 151.26, 159.24.

5-(2-Benzyl-5-(4-fluorophenyl)thiophen-3-yl)-1H-tetrazole (DNM-151A) To a solution of 5-(2-benzyl-5-iodothiophen-3-yl)-2-trityl-2H-tetrazole (915 mg, 1.5 mmol) and Pd(PPh$_3$)$_4$ (69 mg, 0.06) in 15 mL of THF was slowly added a solution of 4-fluorophenylzinc bromide (3.0 mmol, made from 3.0 mmol of 4-fluorophenylmagnesium bromide and 4.5 mmol of zinc chloride). When the addition was complete, the reaction was stirred at room temperature until the reaction was complete (~2 h). Brine was added to the solution, and extracted with ethyl acetate. The organic layer was dried over anhydrous sodium sulfate and concentrated. The residue was purified by flash chromatography (dichloromethane:hexane=3:2) to give 0.60 g (69%) product as a white solid. The solid was suspended in 20 mL of methanol and heated to reflux. The progress of the reaction was monitored by TLC until the reaction was complete. After removing methanol, the residue solid was recrystallized to give 0.314 g (90%) of product as a white solid, $^1$H NMR (500 MHz, DMSO) δ 4.64 (s, 2H), 7.21-7.35 (m, 7H), 7.64 (dd, J=5.29 Hz, J$_2$=8.68 Hz, 2H), 7.82 (s, 1H); $^{13}$C NMR (125 MHz, DMSO) δ 34.71, 116.59, 116.76, 122.52, 123.70, 127.17, 127.71, 127.78, 129.06, 129.08, 129.77, 129.79, 140.03, 141.25, 146.56, 161.37, 163.32.

While the preferred embodiments of the invention have been described above, it will be recognized and understood that various modifications may be made therein, and the appended claims are intended to cover all such modifications which may fall within the spirit and scope of the invention.

TABLE 1

| ORGANISM | n | ORGANISM | ATCC |
| --- | --- | --- | --- |
| A. baumanii | 5 | E. faecalis | 29212 |
| B. cepacia | 7 | S. aureus | 29213 |
| C. amalonaticus | 5 | Ps. aeruginosa | 27853 |
| C. freundii | 5 | E. coli | 25922 |
| C. koseril | 5 | K. pneumoniae | 13883 |
| E. aerogenes | 5 | A. anitratus | 19606 |
| E. cloacae | 5 | E. cloacae | 23355 |
| E. coli | 5 | P. mirabilis | 29245 |
| K. oxytoca | 5 | P. rettgeri | CAP |
| K. pneumoniae | 5 | Pr. stuartii | 33672 |
| M. morganii | 5 | B. cepacia | 25416 |
| P. mirabilis | 5 | S. liquefaciens | 27592 |
| P. retgerri | 3 | S. epidermidis | 14990 |
| P. stuartii | 5 | S. simulans | 27848 |
| P. vulgaris | 5 | S. warneri | 27836 |
| Ps. aeruginosa | 5 | S. saprophyticus | 15305 |
| S. liquifaciens | 4 | S. maltophilia | 13637 |
| S. maltophilia | 5 | P. vulgaris | 49132 |
| S. marcescens | 4 | K. oxytoca | 49131 |
| | | MRSA | 33591 |
| | | S. marcescens | 8100 |
| | | E. faecium | 35667 |
| | | E. aerogenes | 13048 |

TABLE 2

| Compound | Range |
|---|---|
| 111 | 0.5-256 |
| 112 | 0.5-256 |
| 113 | 0.25-128 |
| 114 | 0.5-256 |
| 115 | 0.25-16 |
| 116 | 0.12-32 |
| 121 | 0.5-128 |
| 123 | 0.5-8 |
| 124 | 1-64 |
| 125 | 0.5-16 |

TABLE 2-continued

| Compound | Range |
|---|---|
| 131 | 0.5-32 |
| 132 | 0.5-16 |
| 133 | 0.5-16 |
| 141 | 0.5-16 |
| 142 | 0.5-16 |
| 143 | 0.25-8 |
| 144 | 0.5-8 |
| 145 | 0.25-4 |

TABLE 3A

| ORGANISM | ATCC | DNM-111 | DNM-112 | DNM-113 | DNM-114 | DNM-115 | DNM-116 | DNM-121 | DNM-123 | DNM-124 |
|---|---|---|---|---|---|---|---|---|---|---|
| E. faecalis |  | 8 | 8 | 8 | 8 | 8 | 8 | 8 | 8 | >64 |
| E. faecalis |  | 8 | 8 | 8 | 8 | 8 | 8 | 8 | 8 | >64 |
| E. faecalis |  | 8 | 8 | 8 | 8 | 8 | 8 | 8 | 8 | >64 |
| E. faecalis | 29212 | 8 | 8 | 8 | 8 | 8 | 8 | 8 | 8 | >64 |
| E. faecalis | 29212 | 8 | 8 | 8 | 8 | 8 | 8 | 8 | 8 | >64 |
| E. faecalis | 29212 | 8 | 8 | 8 | 8 | 8 | 8 | 8 | 8 | >64 |
| S. aureus | 29213 | 128 | 16 | 32 | 128 | >16 | 32 | 64 | >8 | >64 |
| S. aureus | 29213 | 128 | 16 | 32 | 128 | >16 | >32 | 32 | >8 | >64 |
| S. aureus | 29213 | 128 | 16 | 32 | 128 | >16 | >32 | 64 | >8 | >64 |
| Ps. aeruginosa | 27853 | 128 | >256 | 8 | 128 | 8 | 16 | 64 | 8 | >64 |
| Ps. aeruginosa | 27853 | 128 | >256 | 8 | 128 | 8 | 16 | 64 | 8 | >64 |
| Ps. aeruginosa | 27853 | 64 | >256 | 8 | 64 | 8 | 16 | 64 | 8 | >64 |
| E. coli | 25922 | 128 | >256 | 8 | 128 | 8 | 16 | 64 | 8 | >64 |
| E. coli | 25922 | 128 | >256 | 8 | 128 | 8 | 8 | 64 | 8 | >64 |
| E. coli | 25922 | 64 | >256 | 8 | 128 | 8 | 16 | 64 | 8 | >64 |
| K. pneumoniae | 13883 | 128 | >256 | 8 | 128 | 8 | 16 | 64 | 8 | >64 |
| A. anitratus | 19606 | 64 | >256 | 8 | 64 | 8 | 16 | 64 | <=0.5 | 64 |
| E. cloacae | 23355 | 128 | >256 | 8 | 128 | >16 | 16 | 64 | 8 | >64 |
| P. mirabilis | 29245 | 128 | >256 | 16 | 128 | 16 | 32 | 64 | >8 | >64 |
| P. rettgeri |  | 128 | >256 | 8 | 128 | 16 | 32 | 64 | >8 | >64 |
| Pr. stuartii | 33672 | 256 | >256 | 16 | 128 | >16 | 32 | 64 | >8 | >64 |
| B. cepacia | 25416 | 64 | >256 | 8 | 64 | 8 | 16 | 64 | <=0.5 | 64 |
| S. liquefaciens | 27592 | 128 | >256 | 8 | 128 | 8 | 16 | 64 | 8 | >64 |
| S. epidermidis | 14990 | 128 | 16 | 8 | 64 | 8 | 16 | 64 | 4 | 64 |
| S. simulans | 27848 | 256 | 8 | 32 | 256 | >16 | >32 | 64 | >8 | >64 |
| S. warneri | 27836 | 256 | 64 | 16 | 128 | >16 | 32 | 64 | >8 | >64 |
| S. saprophyticus | 15305 | 128 | 64 | 8 | 128 | 8 | 16 | 64 | >8 | >64 |
| S. maltophilia | 13637 | 64 | >256 | 8 | 64 | 8 | 16 | 64 | <=0.5 | 64 |
| P. vulgaris | 49132 | 128 | >256 | 16 | 128 | 16 | 32 | 64 | >8 | >64 |
| K. oxytoca | 49131 | 128 | >256 | 8 | 128 | 8 | 16 | 64 | 8 | >64 |
| MRSA | 33591 | 128 | 16 | 64 | 256 | >16 | >32 | 64 | >8 | >64 |
| S. marcescens | 8100 | 128 | >256 | 8 | 128 | 8 | 16 | 64 | 8 | >64 |
| E. faecium | 35667 | 8 | 8 | 8 | 8 | 8 | 8 | 8 | 8 | >64 |
| E. aerogenes | 13048 | 128 | >256 | 8 | 128 | 8 | 16 | 64 | 8 | >64 |

TABLE 3B

| ORGANISM | ATCC | DNM-125 | DNM-131 | DNM-132 | DNM-133 | DNM-141 | DNM-142 | DNM-143 | DNM-144 | DNM-145 | DMSO |
|---|---|---|---|---|---|---|---|---|---|---|---|
| E. faecalis |  |  |  |  |  |  |  |  |  |  |  |
| E. faecalis |  | >16 | 32 | >16 | >16 | >16 | >16 | >8 | >8 | >4 | >64 |
| E. faecalis |  | >16 | >32 | >16 | >16 | >16 | >16 | >8 | >8 | >4 | >64 |
| E. faecalis | 29212 | >16 | >32 | >16 | >16 | >16 | >16 | >8 | >8 | >4 | 64 |
| E. faecalis | 29212 | >16 | >32 | >16 | >16 | >16 | >16 | >8 | >8 | >4 | >64 |
| E. faecalis | 29212 | >16 | >32 | >16 | >16 | >16 | >16 | >8 | >8 | >4 | >64 |
| S. aureus | 29213 |  |  |  |  |  |  |  |  |  |  |
| S. aureus | 29213 | >16 | 32 | >16 | >16 | >16 | >16 | >8 | >8 | >4 | >64 |
| S. aureus | 29213 | >16 | >32 | >16 | >16 | >16 | >16 | >8 | >8 | >4 | >64 |
| Ps. aeruginosa | 27853 |  |  |  |  |  |  |  |  |  |  |
| Ps. aeruginosa | 27853 | >16 | >32 | >16 | >16 | >16 | >16 | >8 | >8 | >4 | >64 |
| Ps. aeruginosa | 27853 | >16 | >32 | >16 | >16 | >16 | >16 | >8 | >8 | >4 | >64 |
| E. coli | 25922 |  |  |  |  |  |  |  |  |  |  |
| E. coli | 25922 | >16 | >32 | >16 | >16 | >16 | >16 | >8 | >8 | >4 | 64 |
| E. coli | 25922 | >16 | >32 | >16 | >16 | >16 | >16 | >8 | >8 | >4 | >64 |
| K. pneumoniae | 13883 | >16 | >32 | >16 | >16 | >16 | >16 | >8 | >8 | >4 | 32 |
| A. anitratus | 19606 | >16 | >32 | >16 | >16 | >16 | >16 | >8 | >8 | >4 | 64 |
| E. cloacae | 23355 | >16 | >32 | >16 | >16 | >16 | >16 | >8 | >8 | >4 | 64 |
| P. mirabilis | 29245 | >16 | >32 | >16 | >16 | >16 | >16 | >8 | >8 | >4 | >64 |

TABLE 3B-continued

| ORGANISM | ATCC | DNM-125 | DNM-131 | DNM-132 | DNM-133 | DNM-141 | DNM-142 | DNM-143 | DNM-144 | DNM-145 | DMSO |
|---|---|---|---|---|---|---|---|---|---|---|---|
| P. rettgeri | | >16 | >32 | >16 | >16 | >16 | >16 | >8 | >8 | >4 | >64 |
| Pr. stuartii | 33672 | >16 | >32 | >16 | >16 | >16 | >16 | >8 | >8 | >4 | 64 |
| B. cepacia | 25416 | >16 | >32 | >16 | >16 | >16 | >16 | >8 | >8 | >4 | >64 |
| S. liquefaciens | 27592 | >16 | >32 | >16 | >16 | >16 | >16 | >8 | >8 | >4 | 64 |
| S. epidermidis | 14990 | >16 | >32 | >16 | >16 | >16 | >16 | >8 | >8 | >4 | 32 |
| S. simulans | 27848 | >16 | >32 | >16 | >16 | >16 | >16 | >8 | >8 | >4 | >64 |
| S. warneri | 27836 | >16 | >32 | >16 | >16 | >16 | >16 | >8 | >8 | >4 | >64 |
| S. saprophyticus | 15305 | >16 | >32 | >16 | >16 | >16 | >16 | >8 | >8 | >4 | >64 |
| S. maltophilia | 13637 | >16 | >32 | >16 | >16 | >16 | >16 | >8 | >8 | >4 | 64 |
| P. vulgaris | 49132 | >16 | >32 | >16 | >16 | >16 | >16 | >8 | >8 | >4 | 64 |
| K. oxytoca | 49131 | >16 | >32 | >16 | >16 | >16 | >16 | >8 | >8 | >4 | >64 |
| MRSA | 33591 | >16 | >32 | >16 | >16 | >16 | >16 | >8 | >8 | >4 | >64 |
| S. marcescens | 8100 | >16 | >32 | >16 | >16 | >16 | >16 | >8 | >8 | >4 | 64 |
| E. faecium | 35667 | >16 | >32 | >16 | >16 | >16 | >16 | >8 | >8 | >4 | >64 |
| E. aerogenes | 13048 | >16 | >32 | >16 | >16 | >16 | >16 | >8 | >8 | >4 | >64 |

TABLE 4A

| ORGANISM | DNM-111 | DNM-112 | DNM-113 | DNM-114 | DNM-115 | DNM-116 | DNM-121 | DNM-123 | DNM-124 |
|---|---|---|---|---|---|---|---|---|---|
| E. COLI | 128 | >256 | 8 | 128 | 8 | 16 | 64 | 8 | >64 |
| E. COLI | 64 | >256 | 8 | 128 | 8 | 16 | 64 | >8 | >64 |
| PS. AER | 128 | 8 | 64 | 8 | 16 | 64 | 8 | 8 | 64 |
| PS. AER | 128 | >256 | 8 | 128 | 8 | 16 | 64 | 8 | >64 |
| E. COLI | 128 | >256 | 8 | 128 | 8 | 16 | 64 | >8 | >64 |
| C. AMALONATICUS | 128 | >256 | 8 | 128 | >16 | 16 | 64 | 8 | >64 |
| P. VULGARIS | 128 | >256 | 8 | 128 | >16 | 16 | 64 | >8 | >64 |
| E. COLI | 32 | >256 | 8 | 128 | >16 | 16 | 64 | >8 | >64 |
| E. COLI | 128 | >256 | 16 | 128 | >16 | 32 | 64 | >8 | >64 |
| S. MARCESCENS | 128 | >256 | 8 | 128 | 8 | 16 | 64 | 8 | >64 |
| E. AEROGENES | 128 | >256 | 8 | 128 | 8 | 16 | 64 | 8 | >64 |
| K. OXYTOCA | 128 | >256 | 8 | 128 | >16 | 16 | 64 | >8 | >64 |
| P. MIRABILIS | 128 | >256 | 16 | 128 | >16 | 16 | 64 | >8 | >64 |
| K. PNEUMONIAE | 128 | >256 | 16 | 128 | >16 | 16 | 64 | >8 | >64 |
| C. KOSERI | 128 | >256 | 8 | 128 | 8 | 16 | 64 | 8 | >64 |
| K. PNEUMONIAE | 128 | >256 | 16 | 128 | >16 | 16 | 64 | >8 | >64 |
| K. PNEUMONIAE | 128 | >256 | 8 | 128 | >16 | 16 | 64 | >8 | >64 |
| P. STUARTII | 256 | >256 | 16 | 128 | >16 | 16 | 64 | >8 | >64 |
| P. MIRABILIS | 128 | >256 | 8 | 128 | >16 | 16 | 64 | >8 | >64 |
| S. MALTOPHILIA | 64 | >256 | 8 | 64 | 8 | 16 | 64 | 8 | >64 |
| K. PNEUMONIAE | 128 | >256 | 8 | 128 | 8 | 16 | 64 | 8 | >64 |
| K. PNEUMONIAE | 128 | >256 | 8 | 128 | >16 | 16 | 64 | >8 | >64 |
| P. VULGARIS | 128 | >256 | 8 | 128 | 8 | 16 | 64 | 8 | >64 |
| P. MIRABILIS | 128 | >256 | 8 | 128 | >16 | 16 | 64 | >8 | >64 |
| M. MORGANII | 128 | >256 | 8 | 128 | >16 | 16 | 64 | >8 | >64 |
| C. FREUNDII | 128 | >256 | 8 | 128 | >16 | 16 | 64 | 8 | >64 |
| B. CEPACIA | 128 | >256 | 8 | 64 | 8 | 16 | 64 | 8 | 64 |
| P. STUARTII | 128 | >256 | 8 | 64 | 8 | 16 | 64 | 4 | >64 |
| E. AEROGENES | 128 | >256 | 8 | 128 | >16 | 16 | 64 | >8 | >64 |
| A. BAUMANII | 128 | >256 | 8 | 32 | 8 | 16 | 64 | <=0.5 | 64 |
| S. MARCESCENS | 128 | >256 | 8 | 128 | 8 | 16 | 64 | 8 | >64 |
| A. BAUMANII | 64 | >256 | 8 | 64 | 8 | 16 | 64 | <=0.5 | 64 |
| C. AMALONATICUS | 128 | >256 | 16 | 128 | >16 | 16 | 64 | >8 | >64 |
| P. MIRABILIS | 128 | >256 | 8 | 128 | 8 | 16 | 64 | 8 | >64 |
| P. MIRABILIS | 128 | >256 | 8 | 128 | 8 | 16 | 64 | 8 | >64 |
| S. MALTOPHILIA | 128 | >256 | 8 | 64 | 8 | 16 | 64 | <=0.5 | >64 |
| S. MARCESCENS | 128 | >256 | 8 | 128 | 8 | 16 | 64 | 8 | >64 |
| M. MORGANII | 128 | >256 | 8 | 128 | 8 | 16 | 64 | 8 | >64 |
| P. STUARTII | 128 | >256 | 8 | 64 | 8 | 16 | 64 | <=0.5 | 64 |
| C. KOSERI | 128 | >256 | 8 | 128 | 8 | 16 | 64 | >8 | >64 |
| P. VULGARIS | 128 | >256 | 8 | 128 | 8 | 16 | 64 | >8 | >64 |
| A. BAUMANII | 64 | >256 | 8 | 64 | 8 | 16 | 64 | <=0.5 | 64 |
| PS. AER | 128 | >256 | 8 | 128 | >16 | 16 | 64 | >8 | >64 |
| P. VULGARIS | 128 | >256 | 8 | 128 | >16 | 16 | 64 | >8 | >64 |
| E. AEROGENES | 128 | >256 | 8 | 128 | 8 | 16 | 64 | 8 | >64 |
| C. KOSERI | 128 | >256 | 8 | 128 | 8 | 16 | 64 | 8 | >64 |
| K. OXYTOCA | 128 | >256 | 8 | 128 | 8 | 16 | 64 | 8 | >64 |
| E. AEROGENES | 128 | >256 | 8 | 128 | 8 | 16 | 64 | 8 | >64 |
| C. AMALONATICUS | 128 | >256 | 8 | 128 | 8 | 16 | 64 | 8 | >64 |
| P. STUARTII | 256 | >256 | 8 | 128 | >16 | 16 | 64 | >8 | >64 |
| P. STUARTII | 128 | >256 | 8 | 128 | 8 | 16 | 64 | 8 | >64 |
| K. OXYTOCA | 128 | >256 | 16 | 128 | >16 | 16 | 64 | >8 | >64 |

TABLE 4A-continued

| ORGANISM | DNM-111 | DNM-112 | DNM-113 | DNM-114 | DNM-115 | DNM-116 | DNM-121 | DNM-123 | DNM-124 |
|---|---|---|---|---|---|---|---|---|---|
| P. RETTGERI | 128 | >256 | 8 | 128 | >16 | 16 | 64 | >8 | >64 |
| A. BAUMANII | 128 | >256 | 8 | 128 | 8 | 16 | 64 | 8 | >64 |
| S. MARCESCENS | 128 | >256 | 8 | 128 | >16 | 16 | 64 | >8 | >64 |
| PS. AER | 128 | >256 | 8 | 128 | 8 | 16 | 64 | 8 | >64 |
| K. OXYTOCA | 128 | >256 | 16 | 128 | >16 | 16 | 64 | >8 | >64 |
| C. AMALONATICUS | 128 | >256 | 8 | 128 | >16 | 16 | 64 | 8 | >64 |
| S. LIQUEFACIENS | 128 | >256 | 8 | 128 | 8 | 16 | 64 | 8 | >64 |
| P. RETTGERI | 128 | >256 | 8 | 128 | 8 | 16 | 64 | 8 | >64 |
| E. CLOACAE | 128 | >256 | 8 | 128 | >16 | 16 | 64 | >8 | >64 |
| E. CLOACAE | 128 | >256 | 16 | 128 | >16 | 16 | 64 | >8 | >64 |
| E. CLOACAE | 128 | >256 | 16 | 128 | >16 | 16 | 64 | >8 | >64 |
| S. MALTOPHILIA | 128 | >256 | 8 | 128 | 8 | 16 | 64 | 8 | >64 |
| K. OXYTOCA | 128 | >256 | 8 | 128 | 8 | 16 | 64 | 8 | >64 |
| C. FREUNDII | 128 | >256 | 5 | 128 | 8 | 16 | 64 | 8 | >64 |
| A. BAUMANII | 64 | >256 | 8 | 64 | 8 | 16 | 64 | <=0.5 | 64 |
| C. FREUNDII | 128 | >256 | 8 | 128 | >16 | 16 | 64 | 8 | >64 |
| C. FREUNDII | 128 | >256 | 8 | 128 | 8 | 16 | 64 | 8 | >64 |
| E. AEROGENES | 128 | >256 | 8 | 128 | >16 | 16 | 64 | 8 | >64 |
| C. FREUNDII | 128 | >256 | 8 | 128 | >16 | 16 | 64 | 8 | >64 |
| S. LIQUEFACIENS | 128 | >256 | 8 | 128 | 8 | 16 | 64 | 8 | >64 |
| S. LIQUEFACIENS | 128 | >256 | 8 | 128 | 8 | 16 | 64 | 8 | >64 |
| E. CLOACAE | 128 | >256 | 8 | 128 | >16 | 16 | 64 | >8 | >64 |
| C. KOSERI | 128 | >256 | 8 | 128 | 8 | 16 | 64 | 8 | >64 |
| C. KOSERI | 128 | >256 | 8 | 128 | >16 | 16 | 64 | >8 | >64 |
| E. CLOACAE | 128 | >256 | 8 | 128 | >16 | 16 | 64 | 8 | >64 |
| P. VULGARIS | 128 | >256 | 16 | 128 | >16 | 32 | 64 | >8 | >64 |
| M. MORGANII | 128 | >256 | 8 | 128 | 8 | 16 | 64 | 8 | >64 |
| PS. AER | 128 | >256 | 8 | 128 | 8 | 16 | 64 | 8 | >64 |
| M. MORGANII | 128 | >256 | 8 | 128 | 8 | 16 | 64 | 8 | >64 |
| C. AMALONATICUS | 128 | >256 | 8 | 128 | 8 | 16 | 64 | >8 | >64 |
| S. LIQUEFACIENS | 128 | >256 | 8 | 128 | >16 | 16 | 64 | >8 | >64 |
| S. MALTOPHILIA | 128 | >256 | 8 | 128 | 8 | 16 | 64 | 8 | >64 |
| S. MALTOPHILIA | 128 | >256 | 8 | 128 | 8 | 16 | 64 | >8 | >64 |
| P. RETTGERI | 256 | >256 | 16 | 128 | >16 | 16 | 64 | >8 | >64 |
| B. CEPACIA | 64 | >256 | 8 | 64 | 8 | 16 | 64 | <=0.5 | >64 |
| B. CEPACIA | 64 | >256 | 8 | 64 | 8 | 16 | 64 | <=0.5 | 64 |
| B. CEPACIA | 64 | >256 | 8 | 64 | 8 | 16 | 64 | <=0.5 | >64 |
| B. CEPACIA | 64 | >256 | 8 | 64 | 8 | 16 | 64 | <=0.5 | >64 |
| B. CEPACIA | 64 | >256 | 8 | 64 | 8 | 16 | 64 | <=0.5 | >64 |
| B. CEPACIA | 64 | >256 | 8 | 64 | 8 | 16 | 64 | <=0.5 | >64 |

TABLE 4B

| ORGANISM | DNM-125 | DNM-131 | DNM-132 | DNM-133 | DNM-141 | DNM-142 | DNM-143 | DNM-144 | DNM-145 | DMSO |
|---|---|---|---|---|---|---|---|---|---|---|
| E. COLI | >16 | >32 | >16 | >16 | >16 | >16 | >8 | >8 | >4 | >64 |
| E. COLI | >16 | >32 | >16 | >16 | >16 | >16 | >8 | >8 | >4 | >64 |
| PS. AER | >16 | >32 | >16 | >16 | >16 | >16 | >8 | >8 | >4 | 64 |
| PS. AER | >16 | >32 | >16 | >16 | >16 | >16 | >8 | >8 | >4 | >64 |
| E. COLI | >16 | >32 | >16 | >16 | >16 | >16 | >8 | >8 | >4 | >64 |
| C. AMALONATICUS | >16 | >32 | >16 | >16 | >16 | >16 | >8 | >8 | >4 | 64 |
| P. VULGARIS | >16 | >32 | >16 | >16 | >16 | >16 | >8 | >8 | >4 | 64 |
| E. COLI | >16 | >32 | >16 | >16 | >16 | >16 | >8 | >8 | >4 | >64 |
| E. COLI | >16 | >32 | >16 | >16 | >16 | >16 | >8 | >8 | >4 | >64 |
| S. MARCESCENS | >16 | >32 | >16 | >16 | >16 | >16 | >8 | >8 | >4 | 64 |
| E. AEROGENES | >16 | >32 | >16 | >16 | >16 | >16 | >8 | >8 | >4 | 64 |
| K. OXYTOCA | >16 | >32 | >16 | >16 | >16 | >16 | >8 | >8 | >4 | >64 |
| P. MIRABILIS | >16 | >32 | >16 | >16 | >16 | >16 | >8 | >8 | >4 | >64 |
| K. PNEUMONIAE | >16 | >32 | >16 | >16 | >16 | >16 | >8 | >8 | >4 | >64 |
| C. KOSERI | >16 | >32 | >16 | >16 | >16 | >16 | >8 | >8 | >4 | 64 |
| K. PNEUMONIAE | >16 | >32 | >16 | >16 | >16 | >16 | >8 | >8 | >4 | >64 |
| K. PNEUMONIAE | >16 | >32 | >16 | >16 | >16 | >16 | >8 | >8 | >4 | >64 |
| P. STUARTII | >16 | >32 | >16 | >16 | >16 | >16 | >8 | >8 | >4 | >64 |
| P. MIRABILIS | >16 | >32 | >16 | >16 | >16 | >16 | >8 | >8 | >4 | >64 |
| S. MALTOPHILIA | >16 | >32 | >16 | >16 | >16 | >16 | >8 | >8 | >4 | >64 |
| K. PNEUMONIAE | >16 | >32 | >16 | >16 | >16 | >16 | >8 | >8 | >4 | 64 |
| K. PNEUMONIAE | >16 | >32 | >16 | >16 | >16 | >16 | >8 | >8 | >4 | >64 |
| P. VULGARIS | >16 | >32 | >16 | >16 | >16 | >16 | >8 | >8 | >4 | >64 |
| P. MIRABILIS | >16 | >32 | >16 | >16 | >16 | >16 | >8 | >8 | >4 | >64 |
| M. MORGANII | >16 | >32 | >16 | >16 | >16 | >16 | >8 | >8 | >4 | >64 |
| C. FREUNDII | >16 | >32 | >16 | >16 | >16 | >16 | >8 | >8 | >4 | >64 |
| B. CEPACIA | >16 | >32 | >16 | >16 | >16 | >16 | >8 | >8 | >4 | 64 |

TABLE 4B-continued

| ORGANISM | DNM-125 | DNM-131 | DNM-132 | DNM-133 | DNM-141 | DNM-142 | DNM-143 | DNM-144 | DNM-145 | DMSO |
|---|---|---|---|---|---|---|---|---|---|---|
| P. STUARTII | >16 | >32 | >16 | >16 | >16 | >16 | >8 | >8 | >4 | 64 |
| E. AEROGENES | >16 | >32 | >16 | >16 | >16 | >16 | >8 | >8 | >4 | >64 |
| A. BAUMANII | >16 | >32 | >16 | >16 | >16 | >16 | >8 | >8 | >4 | 32 |
| S. MARCESCENS | >16 | >32 | >16 | >16 | >16 | >16 | >8 | >8 | >4 | >64 |
| A. BAUMANII | >16 | >32 | >16 | >16 | >16 | >16 | >8 | >8 | >4 | 32 |
| C. AMALONATICUS | >16 | >32 | >16 | >16 | >16 | >16 | >8 | >8 | >4 | >64 |
| P. MIRABILIS | >16 | >32 | >16 | >16 | >16 | >16 | >8 | >8 | >4 | 64 |
| P. MIRABILIS | >16 | >32 | >16 | >16 | >16 | >16 | >8 | >8 | >4 | 64 |
| S. MALTOPHILIA | >16 | >32 | >16 | >16 | >16 | >16 | >8 | >8 | >4 | 64 |
| S. MARCESCENS | >16 | >32 | >16 | >16 | >16 | >16 | >8 | >8 | >4 | >64 |
| M. MORGANII | >16 | >32 | >16 | >16 | >16 | >16 | >8 | >8 | >4 | >64 |
| P. STUARTII | >16 | >32 | >16 | >16 | >16 | >16 | >8 | >8 | >4 | 32 |
| C. KOSERI | >16 | >32 | >16 | >16 | >16 | >16 | >8 | >8 | >4 | >64 |
| P. VULGARIS | >16 | >32 | >16 | >16 | >16 | >16 | >8 | >8 | >4 | 64 |
| A. BAUMANII | >16 | >32 | >16 | >16 | >16 | >16 | >8 | >8 | >4 | 64 |
| PS. AER | >16 | >32 | >16 | >16 | >16 | >16 | >8 | >8 | >4 | >64 |
| P. VULGARIS | >16 | >32 | >16 | >16 | >16 | >16 | >8 | >8 | >4 | >64 |
| E. AEROGENES | >16 | >32 | >16 | >16 | >16 | >16 | >8 | >8 | >4 | >64 |
| C. KOSERI | >16 | >32 | >16 | >16 | >16 | >16 | >8 | >8 | >4 | >64 |
| K. OXYTOCA | >16 | >32 | >16 | >16 | >16 | >16 | >8 | >8 | >4 | >64 |
| E. AEROGENES | >16 | >32 | >16 | >16 | >16 | >16 | >8 | >8 | >4 | >64 |
| C. AMALONATICUS | >16 | >32 | >16 | >16 | >16 | >16 | >8 | >8 | >4 | >64 |
| P. STUARTII | >16 | >32 | >16 | >16 | >16 | >16 | >8 | >8 | >4 | >64 |
| P. STUARTII | >16 | >32 | >16 | >16 | >16 | >16 | >8 | >8 | >4 | 64 |
| K. OXYTOCA | >16 | >32 | >16 | >16 | >16 | >16 | >8 | >8 | >4 | >64 |
| P. RETTGERI | >16 | >32 | >16 | >16 | >16 | >16 | >8 | >8 | >4 | >64 |
| A. BAUMANII | >16 | >32 | >16 | >16 | >16 | >16 | >8 | >8 | >4 | >64 |
| S. MARCESCENS | >16 | >32 | >16 | >16 | >16 | >16 | >8 | >8 | >4 | >64 |
| PS. AER | >16 | >32 | >16 | >16 | >16 | >16 | >8 | >8 | >4 | >64 |
| K. OXYTOCA | >16 | >32 | >16 | >16 | >16 | >16 | >8 | >8 | >4 | 64 |
| C. AMALONATICUS | >16 | >32 | >16 | >16 | >16 | >16 | >8 | >8 | >4 | >64 |
| S. LIQUEFACIENS | >16 | >32 | >16 | >16 | >16 | >16 | >8 | >8 | >4 | 64 |
| P. RETTGERI | >16 | >32 | >16 | >16 | >16 | >16 | >8 | >8 | >4 | 64 |
| E. CLOACAE | >16 | >32 | >16 | >16 | >16 | >16 | >8 | >8 | >4 | >64 |
| E. CLOACAE | >16 | >32 | >16 | >16 | >16 | >16 | >8 | >8 | >4 | >64 |
| E. CLOACAE | >16 | >32 | >16 | >16 | >16 | >16 | >8 | >8 | >4 | >64 |
| S. MALTOPHILIA | >16 | >32 | >16 | >16 | >16 | >16 | >8 | >8 | >4 | 64 |
| K. OXYTOCA | >16 | >32 | >16 | >16 | >16 | >16 | >8 | >8 | >4 | 64 |
| C. FREUNDII | >16 | >32 | >16 | >16 | >16 | >16 | >8 | >8 | >4 | 64 |
| A. BAUMANII | >16 | >32 | >16 | >16 | >16 | >16 | >8 | >8 | >4 | 64 |
| C. FREUNDII | >16 | >32 | >16 | >16 | >16 | >16 | >8 | >8 | >4 | 64 |
| C. FREUNDII | >16 | >32 | >16 | >16 | >16 | >16 | >8 | >8 | >4 | 64 |
| E. AEROGENES | >16 | >32 | >16 | >16 | >16 | >16 | >8 | >8 | >4 | 64 |
| C. FREUNDII | >16 | >32 | >16 | >16 | >16 | >16 | >8 | >8 | >4 | 64 |
| S. LIQUEFACIENS | >16 | >32 | >16 | >16 | >16 | >16 | >8 | >8 | >4 | 64 |
| S. LIQUEFACIENS | >16 | >32 | >16 | >16 | >16 | >16 | >8 | >8 | >4 | 64 |
| E. CLOACAE | >16 | >32 | >16 | >16 | >16 | >16 | >8 | >8 | >4 | 64 |
| C. KOSERI | >16 | >32 | >16 | >16 | >16 | >16 | >8 | >8 | >4 | 64 |
| C. KOSERI | >16 | >32 | >16 | >16 | >16 | >16 | >8 | >8 | >4 | >64 |
| E. CLOACAE | >16 | >32 | >16 | >16 | >16 | >16 | >8 | >8 | >4 | >64 |
| P. VULGARIS | >16 | >32 | >16 | >16 | >16 | >16 | >8 | >8 | >4 | >64 |
| M. MORGANII | >16 | >32 | >16 | >16 | >16 | >16 | >8 | >8 | >4 | >64 |
| PS. AER | >16 | >32 | >16 | >16 | >16 | >16 | >8 | >8 | >4 | >64 |
| M. MORGANII | >16 | >32 | >16 | >16 | >16 | >16 | >8 | >8 | >4 | 64 |
| C. AMALONATICUS | >16 | >32 | >16 | >16 | >16 | >16 | >8 | >8 | >4 | >64 |
| S. LIQUEFACIENS | >16 | >32 | >16 | >16 | >16 | >16 | >8 | >8 | >4 | >64 |
| S. MALTOPHILIA | >16 | >32 | >16 | >16 | >16 | >16 | >8 | >8 | >4 | >64 |
| S. MALTOPHILIA | >16 | >32 | >16 | >16 | >16 | >16 | >8 | >8 | >4 | 64 |
| P. RETTGERI | >16 | >32 | >16 | >16 | >16 | >16 | >8 | >8 | >4 | >64 |
| B. CEPACIA | >16 | >32 | >16 | >16 | >16 | >16 | >8 | >8 | >4 | 64 |
| B. CEPACIA | >16 | >32 | >16 | >16 | >16 | >16 | >8 | >8 | >4 | 64 |
| B. CEPACIA | >16 | >32 | >16 | >16 | >16 | >16 | >8 | >8 | >4 | 64 |
| B. CEPACIA | >16 | >32 | >16 | >16 | >16 | >16 | >8 | >8 | >4 | 64 |
| B. CEPACIA | >16 | >32 | >16 | >16 | >16 | >16 | >8 | >8 | >4 | 64 |
| B. CEPACIA | >16 | >32 | >16 | >16 | >16 | >16 | >8 | >8 | >4 | 64 |

The invention claimed is:

1. A method of inhibiting growth of a bacterium selected from the group consisting of *Escherichia coli*, *Enterococcus faecalis* and *Staphylococcus aureus* to treat a bacterial infection caused by said bacterium, said method comprising administering to an individual in need of such treatment, an effective amount of a purified compound having the structure:

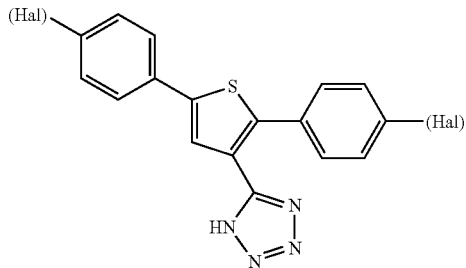

wherein '(Hal)' is any halogen, or a pharmaceutically acceptable salt thereof.

2. The method according to claim 1 wherein the halogen is selected from the group consisting of fluorine, chlorine and bromine.

3. The method according to claim 1 wherein the bacterial infection is caused by *Staphylococcus aureus*.

4. The method according to claim 1 wherein the infection is selected from the group consisting of gasteroenteritis, meningitis, pneumonia, septicaemia, urinary tract infections, gonorrhea, peptic ulcers and nosocomial infections.

5. The method according to claim 1 wherein the infection is a nosocomial infection.

6. The method according to claim 1 wherein the bacterial infection is caused by *Escherichia coli*.

7. The method according to claim 1 wherein the bacterial infection is caused by *Enterococcus faecalis*.

8. The method according to claim 1 wherein the bacterial infection is caused by *Enterococcus faecalis* or *Escherichia coli*.

9. The method according to claim 1 wherein the bacterial infection is caused by *Enterococcus faecalis* or *Staphylococcus aureus*.

10. The method according to claim 1 wherein the bacterial infection is caused by *Staphylococcus aureus* or *Escherichia coli*.

* * * * *